(12) United States Patent
Matschiner et al.

(10) Patent No.: US 9,221,885 B2
(45) Date of Patent: Dec. 29, 2015

(54) MUTEINS OF HUMAN LIPOCALIN 2 WITH AFFINITY FOR CTLA-4

(75) Inventors: Gabriele Matschiner, Munich (DE); Andreas Hohlbaum, Paunzhausen (DE); Arne Skerra, Freising-Weihenstephan (DE)

(73) Assignee: Pieris AG, Freising-Weihenstephan (DE)

( * ) Notice: Subject to any disclaimer, the term of this patent is extended or adjusted under 35 U.S.C. 154(b) by 268 days.

(21) Appl. No.: 13/991,226

(22) PCT Filed: Dec. 2, 2011

(86) PCT No.: PCT/EP2011/071650
§ 371 (c)(1),
(2), (4) Date: Aug. 16, 2013

(87) PCT Pub. No.: WO2012/072806
PCT Pub. Date: Jun. 7, 2012

(65) Prior Publication Data
US 2014/0051645 A1 Feb. 20, 2014

Related U.S. Application Data

(60) Provisional application No. 61/419,072, filed on Dec. 2, 2010.

(30) Foreign Application Priority Data

Dec. 2, 2010 (EP) ..................... 10193401

(51) Int. Cl.
| | | |
|---|---|---|
| *C07K 14/435* | (2006.01) | |
| *C07K 14/705* | (2006.01) | |
| *G01N 33/53* | (2006.01) | |
| *C07K 14/47* | (2006.01) | |
| *C12N 5/10* | (2006.01) | |
| *G01N 33/574* | (2006.01) | |

(52) U.S. Cl.
CPC .............. *C07K 14/435* (2013.01); *C07K 14/47* (2013.01); *C07K 14/705* (2013.01); *C12N 5/10* (2013.01); *G01N 33/57407* (2013.01); *G01N 33/57492* (2013.01); *G01N 2333/70521* (2013.01)

(58) Field of Classification Search
None
See application file for complete search history.

(56) References Cited

U.S. PATENT DOCUMENTS

| | | | |
|---|---|---|---|
| 5,728,553 A | 3/1998 | Goodey et al. | |
| 6,177,074 B1 | 1/2001 | Glue et al. | |
| 6,337,316 B1 | 1/2002 | El Tayar et al. | |
| 6,403,564 B1 | 6/2002 | Ganguly et al. | |
| 6,500,930 B2 | 12/2002 | Adamson | |
| 6,620,413 B1 | 9/2003 | De Sauvage et al. | |
| 6,682,736 B1 | 1/2004 | Hanson et al. | |
| 6,696,245 B2 | 2/2004 | Winter et al. | |
| 7,250,297 B1 | 7/2007 | Beste et al. | |
| 7,892,827 B2 * | 2/2011 | Matschiner et al. | 435/325 |
| 2002/0086014 A1 | 7/2002 | Korman et al. | |
| 2003/0069395 A1 | 4/2003 | Sato et al. | |

FOREIGN PATENT DOCUMENTS

| | | |
|---|---|---|
| EP | 0 330 451 A2 | 8/1989 |
| EP | 0 361 991 A2 | 4/1990 |
| WO | WO 95/33770 A1 | 12/1995 |
| WO | WO 99/16873 A1 | 4/1999 |
| WO | WO 99/64016 A1 | 12/1999 |
| WO | WO 00/75308 A1 | 12/2000 |
| WO | WO 01/14424 A2 | 3/2001 |
| WO | WO 03/029462 A1 | 4/2003 |
| WO | WO 03/029463 A2 | 4/2003 |
| WO | WO 03/029471 A1 | 4/2003 |
| WO | WO 2005/019254 A1 | 3/2005 |
| WO | WO 2005/019255 A1 | 3/2005 |
| WO | WO 2005/019256 A2 | 3/2005 |
| WO | WO 2006/056464 A2 | 6/2006 |
| WO | WO 2007/038619 A2 | 4/2007 |

OTHER PUBLICATIONS

Wells, Biochemistry, 1990 vol. 29, pp. 8509-8517.*
Bork, Genome Research, 2000, vol. 10, pp. 398-400.*
Skolnick et al., Trends in Biotech, 2000, vol. 18, No. 1, pp. 34-39.*
Doerks et al., Trends in Genetics, 1998, vol. 14, pp. 248-250.*
Tokuriki and Tawflik, (Current Opinion in Structural Biology, 2009, vol. 19, pp. 596-604.*
Wang et al. (Nuc. Acids Res. 27: 4609-4618, 1999; p. 4617.*
Kaufman et al (Blood 94: 3178-3184, 1999.*
Altschul et al., "Gapped BLAST and PSI-BLAST: a new generation of protein database search programs," Nucl. Acids Res., 1997, 25(17):3389-3402.
Altuvia et al., "Ranking Potential Binding Peptides to MHC Molecules by a Computational Threading Approach," J. Mol. Biol., 1995, 249:244-250.
Amstutz et al., "In vitro display technologies: novel developments and applications," Curr. Opin. Biotechnol., 2001, 12:400-405.
Attia et al., "Autoimmunity Correlates with Tumor Regression in Patients with Metastatic Melanoma Treated with Anti-Cycotoxic T-Lymphocyte Antigen-4," Journal of Clinical Oncology, Sep. 1, 2005, 23(25):6043-6053.
Bachmann, Barbara J., "Linkage Map of *Escherichia coli* K-12, Edition 8," Microbiol. Rev., Jun. 1990, 54(2):130-197.

(Continued)

*Primary Examiner* — Bridget E Bunner
*Assistant Examiner* — Fozia Hamud
(74) *Attorney, Agent, or Firm* — Foley & Lardner LLP

(57) ABSTRACT

The present invention relates to novel, specific-binding therapeutic and/or diagnostic proteins directed against Cytotoxic T-Lymphocyte Antigen 4 (CTLA-4) also known as CD152, which proteins preferably are muteins of a lipocalin protein, more preferably of lipocalin 2 (Lcn2 or NGAL). The invention also relates to nucleic acid molecules encoding such proteins and to methods for generation and use of such proteins and nucleic acid molecules. Accordingly, the invention also is directed to pharmaceutical and/or diagnostic compositions comprising such lipocalin proteins, including uses of these proteins.

18 Claims, 6 Drawing Sheets

(56) References Cited

OTHER PUBLICATIONS

Balzano et al., "CTLA-4 and CD28: Similar Proteins, Neighbouring Genes," Int. J. Cancer, 1992, Suppl. 7:28-32.
Beste et al., "Small antibody-like proteins with prescribed ligand specificities derived from the lipocalin fold," Proc. Natl. Acad. Sci. USA, Mar. 1999, 96:1898-1903.
Bittker et al., "Nucleic acid evolution and minimization by nonhomologous random recombination," Nat. Biotechnol., Oct. 2002, 20:1024-1029.
Bos et al., "OctoDEX™—Controlled Release of Pharmaceutical Proteins from Hydrogels," Business Briefing: Pharmatech, 2003:1-6.
Bruckdorfer et al., "From Production of Peptides in Milligram Amounts for Research to Multi-Tons Quantities for Drugs of the Future," Curr. Pharm. Biotechnol., 2004, 5:29-43.
Brumano et al., "Thermodynamics of Unfolding of β-Trypsin at pH 2.8," Arch. Biochem. Biophys., Oct. 1, 2000, 382(1):57-62.
Bullock et al., "XL1-Blue: A High Efficiency Plasmid Transforming recA *Escherichia coli* Strain with Beta-Galactosidase Selection," Biotechniques, 1987, 5(4):376-378.
Chambers et al., "CTLA-4-Mediated Inhibition in Regulation of T Cell Responses: Mechanisms and Manipulation in Tumor Immunotherapy," Annu. Rev. Immunol., 2001, 19:565-594.
Chambers et al., "Thymocyte development is normal in CTLA-4-deficient mice," Proc. Natl. Acad. Sci. USA., Aug. 1997, 94(17):9296-9301.
Chikuma et al., "CTLA-4: Acting at the Synapse," Mol. Interv., Jul. 2002, 2(4):205-208.
Cohen et al., "Stability of yeast iso-1-ferricytochrome c as a function of pH and temperature," Protein Sci., 1994, 3(8):1253-1260.
Dennis et al., "Albumin Binding as a General Strategy for Improving the Pharmacokinetics of Proteins," J. Biol. Chem., Sep. 20, 2002, 277(38):35035-35043.
Egen et al., "CTLA-4: new insights into its biological function and use in tumor immunotherapy," Nat. Immunol., Jul. 2002, 3(7):611-618.
Fuertges et al., :The Clinical Efficacy of Poly(Ethylene Glycol)-Modified Proteins,: J. Control. Release, 1990, 11:139-148.
Gaillard et al., "Diphtheria toxin receptor-targeted brain drug delivery," International Congress Series., 2005, 1277:185-198.
Gaillard et al., "Targeted delivery across the blood-brain barrier," Expert Opin Drug Deliv., 2005, 2(2):299-309.
Hodi et al., "Biologic activity of cytotoxic T lymphocyte-associated antigen 4 antibody blockade in previously vaccinated metastatic melanoma and ovarian carcinoma patients," Proc. Natl. Acad. Sci. USA, Apr. 15, 2003, 100(8):4712-4717.
Holliger et al., "'Diabodies': Small bivalent and bispecific antibody fragments," PNAS USA, Jul. 1993, 90:6444-6448.
Ill et al., "Design and construction of a hybrid immunoglobulin domain with properties of both heavy and light chain variable regions," Protein Engineering, 1997, 10(8):949-957.
Kim et al., "High-Affinity Recognition of Lanthanide(III) Chelate Complexes by a Reprogrammed Human Lipocalin 2," J. Am. Chem. Soc., 2009, 131:3565-3576.
Könic et al., "Use of an albumin-binding domain for the selective immobilization of recombinant capture antibody fragments on ELISA plates," J. Immunol. Methods, 1998, 218:73-83.
Lute et al., "Human CTLA4 knock-in mice unravel the quantitative link between tumor immunity and autoimmunity induced by anti-CTLA-4 antibodies," Blood, Nov. 1, 2005, 106(9): 3127-3133.
Martin et al., "The affinity-selection of a minibody polypeptide inhibitor of human interleukin-6," The EMBO Journal, 1994, 13(22):5303-5309.
Mateo et al., "Removal of Amphipathic Epitopes from Genetically Engineered Antibodies: Production of Modified Immunoglobulins with Reduced Immunogenicity," Hybridoma, 2000, 19(6):463-471.

McCoy et al., "Protective Immunity to Nematode Infection is Induced by CTLA-4 Blockade," J. Exp. Med., Jul. 21, 1997, 186(2):183-187.
Meidan et al., "Emerging Technologies in Transdermal Therapeutics," American Journal of Therapeutics, 2004, 11:312-316.
Murakami et al., "Random insertion and deletion of arbitrary No. Of bases for codon-based random mutation of DNAs," Nat. Biotechnol., Jan. 2002, 20:76-81.
Murata et al., "Expression of the Costimulatory Molecule BB-1, the Ligands CTLA-4 and CD28, and their mRNA in Inflammatory Myopathies," Am. J. Pathol., Aug. 1999, 155(2):453-460.
Murphy et al., "Blockade of CTLA-4 Enhances Host Resistance to the Intracellular Pathogen, *Leishmania donovani*," J. Immunol., 1998, 161:4153-4160.
Osborn et al., "Pharmacokinetic and Pharmacodynamic Studies of a Human Serum Albumin-Interferon-α Fusion Protein in Cynomolgus Monkeys," J. Pharmacol. Exp. Ther., 2002, 303(2):540-548.
Phan et al., "Cancer regression and autoimmunity induced by cytotoxic T lymphocyte-associated antigen 4 blockade in patients with metastatic melanoma," Proc. Natl. Acad. Sci. USA, Jul. 8, 2003, 100(14):8372-8377.
Pini et al., "Phage Display and Colony Filter Screening for High-Throughput Selection of Antibody Libraries," Comb. Chem. High Throughput Screen., 2002, 5:503-510.
Sanderson et al., "Autoimmunity in a Phase I Trial of a Fully Human Anti-Cytotoxic T-Lymphocyte Antigen-4 Monoclonal Antibody with Multiple Melanoma Peptides and Montanide ISA 51 for Patients with Resected Stases III and IV Melanoma," J. Clin. Oncol. Feb. 1, 2005 23(4):741-750.
Schiweck et al., "Fermenter Production of an Artificial Fab Fragment, Rationally Designed for the Antigen Cystatin, and Its Optimized Crystallization Through Constant Domain Shuffling," Proteins: Structure, Function and Genetics, 1995, 23:561-565.
Schlehuber et al., "Duocalins, engineered ligand-binding proteins with dual specificity derived from the lipocalin fold," Biol. Chem., Sep. 2001, 382:1335-1342.
Schlehuber et al., "A Novel Type of Receptor Protein, Based on the Lipocalin Scaffold, with Specificity for Digoxigenin," J. Mol. Biol., 2000, 297:1105-1120.
Schmidt et al., "Molecular Interaction Between the Strep-tag Affinity Peptide and its Cognate Target, Streptavidin," J. Mol. Biol., 1996, 255:753-766.
Schoenfeld et al., "An engineered lipocalin specific for CTLA-4 reveals a combining site with structural and conformational features similar to antibodies," PNAS, May 19, 2009, 106(20:8198-8203.
Silverman et al., "Multivalent avimer proteins evolved by exon shuffling of a family of human receptor domains," Nature Biotechnology, Dec. 2005, 23(12):1556-1561.
Skerra et al., "Use of the *Strep*-Tag and Streptavidin for Detection and Purification of Recombinant Proteins," Methods in Enzymology, 2000, vol. 326, pp. 271-304.
Skerra, Arne, "'Anticalins': a new class of engineered ligand-binding proteins with antibody-like properties," Reviews in Mol. Biotechnol., 2001, 74:257-275.
Skerra, Arne, "Lipocalins as a scaffold," Biochimica et Biophysica Acta, 2000, 1482:337-350.
Tivol et al., "Loss of CTLA-4 Leads to Massive Lymphoproliferation and Fatal Multiorgan Tissue Destruction, Revealing a Critical Negative Regulatory Role of CTLA-4," Immunity, Nov. 1995, 3(5):541-547.
Traunecker et al., "Bispecific single chain molecules (Janusins) target cytotoxic lymphocytes on HIV infected cells," The EMBO Journal, 1991, 10(12):3655-3659.
Traunecker et al., "Janusin: New Molecular Design for Bispecific Reagents," Int. J. Cancer, 1992, Supplement 7, 51-52.
Vajo et al., "Genetically Engineered Insulin Analogs: Diabetes in the New Millenium," Pharmacol. Rev., 2000, 52(1):1-9.
Venturi et al., "High Level Production of Functional Antibody Fab Fragments in an Oxidizing Bacterial Cytoplasm," J. Mol. Biol., 2002, 315:1-8.

(56) References Cited

OTHER PUBLICATIONS

Waterhouse et al., "Lymphoproliferative Disorders with Early Lethality in Mice Deficient in CTLA-4," Science, Nov. 10, 1995, 270(5238):985-988.

Wilson et al., "The use of mRNA display to select high-affinity protein-binding peptides," Proc. Natl. Acad. Sci. USA, Mar. 27, 2001, 98(7):3750-3755.

Yanisch-Perron et al., "Improved M13 phage cloning vectors and host strains: nucleotide sequences of the M13mp18 and pUC19 vectors," Gene, 1985, 33:103-119.

Zaccolo et al., "An Approach to Random Mutagenesis of DNA Using Mixtures of Triphosphate Derivatives of Nucleoside Analogues," J. Mol. Biol., 1996, 255:589-603.

\* cited by examiner

FIGURE 1

Replacement Drawing 2/6

| SEQ ID NO | Mutein | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|---|---|---|---|---|---|---|---|---|---|---|
| 20 | hNGAL | Q | D | S | T | S | D | L | - | P | A | P | P | L | S | K | V | P | L | Q | Q | N | F | Q | D | N | Q | F | H | G | K |
| 1 25 | hNGALM1 | Q | D | S | T | S | D | L | - | P | A | P | P | L | S | K | V | P | L | Q | Q | N | F | Q | D | N | Q | F | H | G | K |
| 42 30 | hNGALM2 | Q | D | S | T | S | D | L | - | P | A | P | P | L | S | K | V | P | L | Q | Q | N | F | Q | D | N | Q | F | H | G | K |
| 43 31 | hNGALM3 | Q | D | S | T | S | D | L | - | P | A | P | P | L | S | K | V | P | L | Q | Q | N | F | Q | D | N | Q | F | H | G | K |
| 44 32 | hNGALM4 | Q | D | S | T | S | D | L | - | P | A | P | P | L | S | K | V | P | L | Q | Q | N | F | Q | D | N | Q | F | H | G | K |
| 45 33 | hNGALM5 | Q | D | S | T | S | D | L | - | P | A | P | P | L | S | K | V | P | L | Q | Q | N | F | Q | D | N | Q | F | H | G | K |
| 46 34 | hNGALM6 | Q | D | S | T | S | D | L | - | P | A | P | P | L | S | K | V | P | L | Q | Q | N | F | Q | D | N | Q | F | H | G | K |
| 47 35 | hNGALM7 | Q | D | S | T | S | D | L | - | P | A | P | P | L | S | K | V | P | L | Q | Q | N | F | Q | D | N | Q | F | H | G | K |

| SEQ ID NO | Mutein | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 |
|---|---|---|---|---|---|---|---|---|---|---|---|---|---|---|---|---|---|---|---|---|---|---|---|---|---|---|---|---|---|---|---|
| 20 | hNGAL | W | Y | V | V | G | L | A | G | N | A | - | L | R | E | D | K | D | P | Q | K | M | Y | A | T | - | Y | E | L | K | E |
| 1 25 | hNGALM1 | W | Y | V | V | G | L | A | G | N | R | - | L | R | D | D | Q | H | P | M | H | M | Y | A | T | - | Y | E | L | K | G |
| 42 30 | hNGALM2 | W | Y | V | V | G | L | A | G | N | R | - | L | R | D | D | Q | H | P | M | D | M | Y | A | T | - | Y | E | L | K | G |
| 43 31 | hNGALM3 | W | Y | V | V | G | L | A | G | N | R | L | L | R | D | D | Q | H | P | M | L | M | Y | A | T | - | Y | E | L | K | G |
| 44 32 | hNGALM4 | W | Y | V | V | G | L | A | G | N | R | - | L | R | D | D | Q | H | P | M | P | M | Y | A | T | - | Y | E | L | K | G |
| 45 33 | hNGALM5 | W | Y | V | V | G | L | A | G | N | R | - | L | R | D | D | Q | H | P | M | H | M | Y | A | T | - | Y | E | L | K | G |
| 46 34 | hNGALM6 | W | Y | V | V | G | L | A | G | N | R | - | L | R | D | D | Q | H | P | M | P | M | Y | A | T | - | Y | E | L | K | G |
| 47 35 | hNGALM7 | W | Y | V | V | G | L | A | G | N | R | - | L | R | L | D | Q | H | P | M | P | M | Y | A | T | - | Y | E | L | K | G |

| SEQ ID NO | Mutein | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 | 89 | 90 |
|---|---|---|---|---|---|---|---|---|---|---|---|---|---|---|---|---|---|---|---|---|---|---|---|---|---|---|---|---|---|---|---|
| 20 | hNGAL | D | K | S | Y | N | V | T | S | V | L | F | R | K | K | K | C | D | Y | W | K | R | T | F | V | P | G | S | Q | P | G |
| 1 25 | hNGALM1 | D | K | S | Y | N | V | T | S | V | - | S | S | H | K | K | C | L | Y | P | - | A | T | F | V | P | G | S | Q | P | G |
| 42 30 | hNGALM2 | D | K | S | Y | N | V | T | S | V | - | S | S | H | K | K | C | L | Y | P | - | A | T | F | V | P | G | S | Q | P | G |
| 43 31 | hNGALM3 | D | K | S | Y | N | V | T | S | V | - | S | S | H | K | K | C | L | Y | P | - | A | T | F | V | P | G | S | Q | P | G |
| 44 32 | hNGALM4 | D | K | S | Y | N | V | T | S | V | - | S | S | H | K | K | C | L | Y | P | - | A | T | F | V | P | G | S | Q | P | G |
| 45 33 | hNGALM5 | D | K | S | Y | N | V | T | S | V | - | S | S | H | K | K | C | L | Y | P | - | A | T | F | V | P | G | S | Q | P | G |
| 46 34 | hNGALM6 | D | K | S | Y | N | V | T | S | V | - | S | S | H | K | K | C | L | Y | P | - | A | T | F | V | P | G | S | Q | P | G |
| 47 35 | hNGALM7 | D | K | S | Y | N | V | T | S | V | - | S | S | H | K | K | C | L | Y | P | - | A | T | F | V | P | G | S | Q | P | G |

MUTEINS OF HUMAN LIPOCALIN 2 WITH AFFINITY FOR CTLA-4

CROSS-REFERENCE TO RELATED APPLICATIONS

This application is the U.S. National Phase of PCT/EP2011/071650, filed Dec. 2, 2011, which was published in English on Jun. 7, 2012, as WO 21012/072806, and claims benefit of the U.S. Provisional Application No. 61/419,072 and European Application EP 10193401.6, both filed Dec. 2, 2010.

The instant application contains a Sequence Listing which has been submitted in ASCII format via EFS-WEB and is hereby incorporated by reference in its entirety. Said ASCII copy, created on Jul. 22, 2015, is named 029029-0148_SL.txt and is 51,950 bytes.

BACKGROUND

CTLA-4 is a member of the immunoglobulin superfamily, which is expressed on the surface of Helper T cells and transmits an inhibitory signal to T cells. CTLA-4 is similar to the T-cell costimulatory protein CD28, and both molecules bind to CD80 and CD86 on antigen-presenting cells. CTLA4 transmits an inhibitory signal to T cells, whereas CD28 transmits a stimulatory signal. Intracellular CTLA-4 is also found in regulatory T cells and may be important to their function. T cell activation through the T cell receptor and CD28 leads to increased expression of CTLA-4, an inhibitory receptor for B7 molecules (i.e. CD80 and CD86). Multiphoton microscopy studies observing T-cell motility in intact lymph nodes gave evidence for the so called 'reverse-stop signaling model'. In this model CTLA 4 reverse the classic TCR-induced 'stop signal' needed for firm contact between T cells and antigen-presenting cells (APCs).

The CTLA-4 protein contains an extracellular V domain, a transmembrane domain, and a cytoplasmic tail. Alternate splice variants, encoding different isoforms, have been characterized. The membrane-bound isoform functions as a homodimer interconnected by a disulfide bond, while the soluble isoform functions as a monomer. The intracellular domain is similar to that of CD28, in that it has no intrinsic catalytic activity and contains one YVKM motif able to bind PI3K, PP2A and SHP-2 and one proline-rich motif able to bind SH3 containing proteins. The first role of CTLA-4 in inhibiting T cell responses seem to be directly via SHP-2 and PP2A dephosphorylation of TCR-proximal signalling proteins such as CD3 and LAT. CTLA-4 can also affect signalling indirectly via competing with CD28 for CD80/86 binding. CTLA-4 can also bind PI3K, although the importance and results of this interaction are uncertain.

CTLA-4 deficient mice develop a massive and lethal lymphoproliferative disease that is more severe than similar phenotypes observed in lpr mice, gld mice, mice with a T cell specific defect in TGFβ signal transduction or targeted deletion of the inhibitory molecule PD-1 (Chambers et al., Annu. Rev. Immunol. (2001), 19: 565-94). Absence of CTLA-4 results in an activated phenotype of peripheral T cells (Waterhouse et al., Science (1995) 10; 270 (5238): 985-8, Tivol et al., Immunity (1995) 3(5):541-7) whereas thymocyte development appears to be normal (Chambers et al., Proc. Natl. Acad. Sci. USA. (1997) 94(17):9296-301). From these observations it was concluded that CTLA-4 is necessary to regulate peripheral T cell tolerance and homeostasis of $CD4^+$ and $CD8^+$ T cells as polyclonal expansion of both populations occurs. The absence of CTLA-4 is most evident during the secondary responses in $CTLA-4^{-/-}$ TCR-transgenic models (Chambers C A et al Proc. Natl. Acad. Sci. USA. (1999) 96(15): 8603-8).

Several molecular mechanisms by which CTLA-4 inhibition occurs have been proposed including direct effects on phosphorylation levels, indirect effects due to competition with CD28 for ligand, sequestration of signalling molecules or disruption of signalling complexes (Chambers et al., Annu Rev Immunol. 2001; 19:565-94, Egen et al., Nat. Immunol. (2002) 3(7):611-8, Chikuma and Bluestone, Mol. Interv. 2002 2(4):205-8). Although the identity of the phosphatases involved are still debated, decreased phosphorylation of proximal TCR signalling molecules like CD3 ζ, EKR and JUN-N-terminal kinase have been observed when CTLA-4 cross-linking was used experimentally as CTLA-4 agonist. CTLA-4 might function at least in part by competing with CD28 for B7 ligands and thereby attenuating co-stimulatory signals indirectly particularly when B7 levels are low. Direct signalling through the tail of CTLA-4 appears to be necessary when B 7 levels are high which is further supported by the fact that a tailless CTLA-4 mutant on the cell surface of transgenic T cells in CTLA-4-/- mice delayed but did not prevent T cell activation and lymphoproliferation. The third model proposes that CTLA-4 physically disturbs the assembly or organization of molecules in the immunologic synapse. Formation of stable CTLA-4/B7 lattices due to the possible interaction of one CTLA-4 molecule with two B7 dimers as suggested by crystal structures may disturb the organized assembly of key components involved in the generation of TCR/CD28 signals.

CTLA-4 blockade with monoclonal antibodies or antibody fragments has been shown to lead to the rejection of a number of immunogenic transplantable tumor cell lines including colorectal carcinoma, renal carcinoma, lymphoma and fibrosarcoma cell lines (see for example, U.S. Pat. No. 6,682,736, US patent application 2002/0086014 or International patent application WO 01/14424). Less immunogenic tumor cell lines required concurrent combination therapy with a tumor vaccine, low dose of chemotherapy or surgical resection. The anti-tumor response elicited by CTLA-4 blockade is directed also towards normal tissue-derived proteins as autoimmune reactions were observed in mouse tumor models (B 16 melanoma, TRAMP tumor cell) and clinical trials. Recent phase I and II studies with human monoclonal antibodies are encouraging and the concurrent development of autoimmune reactions appears to be clinically manageable and might even correlate with therapeutic efficacy (Phan et al., Proc. Natl. Acad. Sci. USA (2003), 100: 8372-77, Sanderson et al. (2005), J. Clin. Oncol. 23: 741-50, Attia et al. (2005), J. Clin. Oncol. 23: 6043-53). On the other hand, recent results support the notion that enhanced tumor immunity through CTLA-4 blockade does not necessarily have to be linked with increased autoimmunity (Hodi et al., Proc. Natl. Acad. Sci USA (2003), 100: 4712-17, Lute et al., Blood (2005), 106(9): 3127-33). In addition to the application in cancer therapy, the use of CTLA-4 binding immunoglobulins for the treatment of infectious diseases and or auto-immune diseases is subject of intensive research.

However, antibodies and fragments thereof may not be suitable for all potential applications. One limiting factor may be their rather large molecular size, which is the case not only for intact antibodies but also for their antigen-binding fragments such as Fab fragments.

For this reason, alternatives to CTLA-4 blocking antibodies have been considered soon after the therapeutic potential of these antibodies emerged. International patent application WO 90/33770 is generally directed to ligands for T cell surface molecules, especially CTLA-4, which induces antigen specific apoptosis of activated T cells. Isolated peptides containing CTLA-4 fragments, constituting the epitope for such binding, are also disclosed and claimed. U.S. Pat. No. 6,337,316 discloses peptidometics capable of inhibiting CD28 and/or CTLA-4 interaction with CD80 (B7-1) and CD86 (B7-2) and having the core amino acid sequence Leu-Met-Tyr-Pro-Pro-Tyr-Tyr (SEQ ID NO: 36). An alternative to CTLA-4 blocking antibodies are recombinant lipocalins which bind CTLA-4 (see WO2006056464 and Schönfeld et al. (2009), Proc. Natl. Acad. Sci. USA 106(20): 8198-8203).

Despite these approaches, it would still be desirable to have further alternatives, yet even improved molecules that bind CTLA-4, for example for blocking the CTLA-4 interaction, and can be used in pharmaceutical and/or diagnostical applications as described above. It would also be desirable to have a compound that has an improved efficacy. Accordingly, it is an object of the present invention to provide such compounds.

DESCRIPTION OF FIGURES

FIG. 1 illustrates the PCR assembly strategy for the simultaneous random mutagenesis of the 10 amino acid positions 44, 50, 79, 81, 104, 125, 127, 128, 130, and 134 (underlined and numbered) in the amino acid sequence of the CTLA-4 specific Lcn2 mutein hNGALMI (SEQ ID NO: 1) which serves as a template. These 10 positions were divided into four sequence subsets. For randomization of the amino acids in each subset an oligodeoxynucleotide was synthesized (SEQ ID NO: 2, SEQ ID NO: 3, SEQ ID NO: 4, SEQ ID NO: 5) wherein NNS mixtures of the nucleotides were employed at the mutated codons. N means a mixture of all four bases A, C, G, and T while S means a mixture of only the two bases C and G: hence such a triplet encodes all 20 natural amino acids as well as the amber stop codon TAG, which is translated as glutamine in the *E coli* supE-strains XL1-blue (Bullock et al., BioTechniques 5 (1987), 376-378) or TG1 (Sambrook et al., Molecular Cloning, A Laboratory Manual (1989), Cold Spring Harbor Press) that were used for phagemid production and gene expression. At five of the overall 10 mutated amino acid positions (79, 81, 127, 130, and 134) the genetical code was restricted in a way to allow not all 20 natural amino acids but only a certain subset to occur. In detail, at position 79 the triplet HCT codes either for threonine, proline or serine, at position 81 the triplet GSA codes either for alanine or serine, at position 127 the triplet RRS codes either for glycine, asparagine, lysine, serine, glutamate, aspartate, or arginine, at position 130 the triplet KHC codes either for alanine, aspartate, valine, serine, tyrosine, or phenylalanine, and at position 134 the triplet KCT codes either for alanine, or serine. According to this restricted triplet codes, H means a mixture of only the three bases A, C, or T, R means a mixture of only the two bases A or G, and K means a mixture of only the two bases G or T. One additional oligodeoxynucleotides (SEQ ID NO: 6) with fixed nucleotide sequences corresponding to the non-coding strand (written below the DNA double strand sequence in 3'-5' direction) and tilling the gap between the aforementioned oligodeoxynucleotides was also used in the assembly reaction. Two shorter flanking oligodeoxynucleotides (SEQ ID NO: 7 and SEQ ID NO: 8), which were added in excess and carried biotin groups, served as primers for the PCR amplification of the assembled, entirely synthetic gene fragment. The two flanking primers each encompassed a BstX1 restriction site (CCANNNNNNTGG (SEQ ID NO: 21)), giving rise to mutually non-compatible overhangs upon enzyme digestion. This special arrangement of restriction sites enabled a particularly efficient ligation and cloning of the synthetic gene. Substitution of the amino acid Gln28 to His with respect to the original Lcn2 sequence was necessary to introduce the first BstXI site, while the second one naturally occurs in the cDNA of Lcn2. Furthermore, the unpaired residue Cys87 was replaced by Ser during the gene assembly. After assembly PCR the resulting gene fragment was inserted into a vector providing the missing parts of the Lcn2 structural gene. This illustration also depicts two short primers (SEQ ID NO: 18 and SEQ ID NO: 19) upstream and downstream, respectively, of the cassette flanked by the two BstXI restriction sites, which served for double stranded DNA sequencing. FIG. 1 discloses SEQ ID NOS 7, 28, 29, 25, 2, 4, 26, 6, 27, and 8, top to bottom, left to right, respectively, in order of appearance. Figure also discloses Strep-Tag™ as SEQ ID NO: 38.

FIGS. 2A-2B depicts an alignment of certain amino acid sequences of CTLA4-specific, NGAL-based lipocalin muteins in comparison with the polypeptide sequence of hNGALMI (SEQ ID NO: 1) which served as a basis for affinity maturation. The NGAL-derived, CTLA4-binding muteins (SEQ ID NOs: 1 and 12-17) comprise residues 1 to 178, meaning they have the length of the mature wildtype proteins. Residues 179 to 188 are the sequence of a streptavidin binding tag, Strep-Tag™, used in the isolation of generated muteins. Generally, when reference is made herein to SEQ ID NOs: 1, 12, 13, 14, 15, 16 or 17 preferably a lipocalin mutein without the Strep-Tag™ is meant. Also depicted is the human NGAL wild type sequence (SEQ ID NO. 20). Alignment discloses full-length sequences including Strep-Tag™ as SEQ ID NOS 25 and 30-35, respectively, in order of appearance. Figure also discloses Strep-Tag™ as SEQ ID NO: 38.

FIG. 3 shows circular dichroism spectra of purified CTLA4-specific lipocalin mutein hNGALM4 (SEQ ID NO: 14) displaying the transition from folded to unfolded state. The unfolded protein fraction f(u) was plotted as a function of temperature T to determine the melting temperature of each lipocalin mutein.

FIG. 4 depicts the results of a cell-based competition assay of affinity matured Lcn2 muteins blocking human B7.1 binding to a human CTLA4-transfected CHO cell line.

FIG. 5 depicts in comparision the specific in vivo activity of a CTLA4-specific lipocalin mutein hNGALM4 (SEQ ID NO: 14) in the murine syngenic CSA1M tumor model.

SUMMARY OF THE INVENTION

One embodiment of the current invention relates to a lipocalin mutein that is capable of binding Cytotoxic T-Lymphocyte Antigen 4 (CTLA-4), also known as CD152, with an affinity measured by a $K_D$ of about 1 nM or lower. More preferably, the lipocalins can have an affinity measured by a $K_D$ of about 0.8 nM or 0.6 nM or lower, i.e., in the picomolar range. In another embodiment, the lipocalin mutein is capable of competing with human B7.1 for binding to human CTLA-4 in a competition assay preferably with an EC50 value of about 60 nM, 50 nM, 15 nM or 10 nM, or lower.

In another embodiment, the invention relates to a lipocalin mutein comprising at one or more positions corresponding to position 44, 50, 79, 81, 98, 104, 125, 127, 128, 130 and/or 134 of the linear polypeptide sequence of SEQ ID NO:1 a substitution.

In particular embodiments, the mutein of the invention comprises at least 1, 2, 3, 4, 5, 6, 7, 8, 9, 10, or 11 substitution(s) (or even more substitutions such as 12, 13, 14, 15, 16, 17, 18, 19 or 20) at a sequence position corresponding to sequence position 44, 50, 79, 81, 98, 104, 125, 127, 128, 130 and/or 134 of the linear polypeptide sequence of SEQ ID NO:1.

Figure 3:
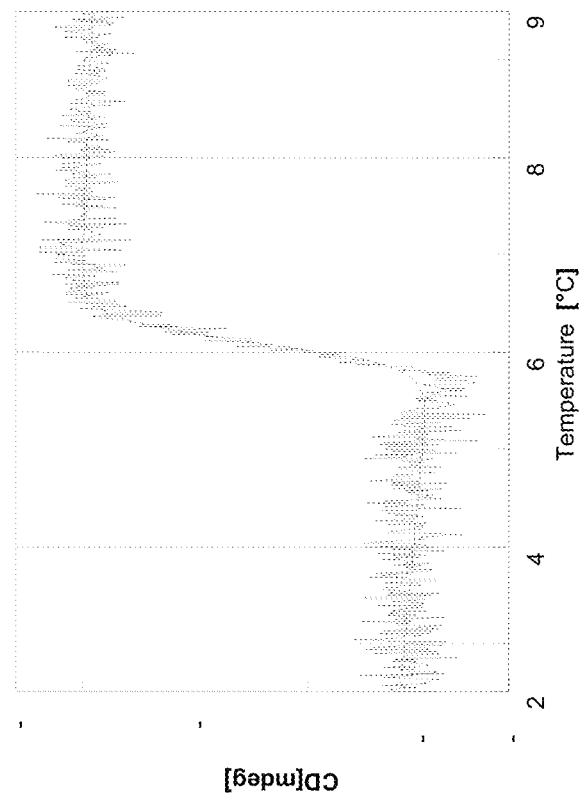

Similarly, the invention relates to a polypeptide comprising SEQ ID NO: 1, wherein said polypeptide comprises 1, 2, 3, 4, 5, 6, 7, 8, 9, 10, or 11 (or even more substitutions such as 12, 13, 14, 15, 16, 17, 18, 19 or 20) mutated amino acid residues at the sequence positions 44, 50, 79, 81, 98, 104, 125, 127, 128, 130 and/or 134. Said polypeptide is preferably an anticalin which preferably binds CTLA-4, in particular human CTLA-4.

In further particular embodiments, a lipocalin mutein according to the current invention comprises an amino acid sequence selected from the group consisting of SEQ ID NOs: 1 and 12-17. In another embodiment, the mutein has at least 70% identity to the sequence of a wild-type human lipocalin, including human Lipocalin 2 (hNGAL). Preferably, said mutein comprises 1, 2, 3, 4, 5, 6, 7, 8, 9, 10, or 11 mutated amino acid residues at the sequence positions 44, 50, 79, 81, 98, 104, 125, 127, 128, 130 and/or 134 of the linear polypeptide sequence of NGAL (SEQ ID NO: 1).

In another embodiment, the mutein of the current invention is conjugated to a compound selected from the group consisting of an organic molecule, an enzyme label, a radioactive label, a colored label, a fluorescent label, a chromogenic label, a luminescent label, a hapten, digoxigenin, biotin, a cytostatic agent, a toxins, a metal complex, a metal, and colloidal gold. The mutein can be fused at its N-terminus and/or its C-terminus to a fusion partner which is a protein, a protein domain, or a peptide.

In another embodiment, the mutein is conjugated to a compound that extends the serum half-life of the mutein. More preferably, the mutein is conjugated to a compound selected from the group consisting of a polyalkylene glycol molecule, a hydroethylstarch, an Fc part of an immunoglobulin, a CH3 domain of an immunoglobulin, a CH4 domain of an immunoglobulin, an albumin binding peptide, and an albumin binding protein.

In another embodiment, the mutein of the current invention is an antagonist of CTLA-4.

In another embodiment, the current invention relates to a nucleic acid molecule comprising a nucleotide sequence encoding a mutein of the current invention.

In yet another embodiment, the invention encompasses a host cell containing said nucleic acid molecule.

In another embodiment, the lipocalin mutein of the current invention is selected from the group consisting of muteins of retinol-binding protein (RBP), bilin-binding protein (BBP), apolipoprotein D (APO D), neutrophil gelatinase associated lipocalin (NGAL), tear lipocalin (TLPC), α2-microglobulin-related protein (A2m), 24p3/uterocalin (24p3), von Ebners gland protein 1 (VEGP 1), von Ebners gland protein 2 (VEGP 2), and Major allergen Can f1 precursor (ALL-1). In related embodiments, the lipocalin mutein is selected from the group consisting of human neutrophil gelatinase associated lipocalin (hNGAL), human tear lipocalin (hTLPC), human apolipoprotein D (APO D) and the bilin-binding protein of *Pieris brassicae*.

The invention also includes a method of treating cancer, preferably lung cancer, bone cancer, pancreatic cancer, skin cancer, cancer of the head or neck, cutaneous or intraocular malignant melanoma, uterine cancer, ovarian cancer, rectal cancer, cancer of the anal region, stomach cancer, colon cancer, breast cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemias, solid tumors of childhood, lymphocytic lymphoma, cancer of the bladder, cancer of the kidney or ureter, renal cell carcinoma, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, t-cell lymphoma, cutaneous T cell lymphoma (CTCL), and combinations of said cancers, the method comprising administering a pharmaceutical composition containing a mutein as described herein to a subject in need thereof.

DETAILED DESCRIPTION OF THE INVENTION

In one aspect, the present invention relates to novel, specific-binding proteins directed against or specific for CTLA-4. Proteins of the invention may be used for therapeutic and/or diagnostic purposes. A protein of the invention includes particularly a lipocalin mutein, also designated herein as "mutein of a lipocalin" or "anticalin". More preferably, a protein of the invention is a hNGAL mutein as described herein. As used herein, a protein of the invention "specifically binds" a target (here, CTLA-4), if it is able to discriminate between that target and one or more reference targets, since binding specificity is not an absolute, but a relative property. "Specific binding" can be determined, for example, in accordance with Western blots, ELISA-, RIA-, ECL-, IRMA-tests, FACS, IHC and peptide scans.

Likewise, in another aspect, the invention relates to a lipocalin mutein, wherein said mutein comprises at one or more positions corresponding to position 44, 50, 79, 81, 98, 104, 125, 127, 128, 130 and/or 134 of the linear polypeptide sequence of SEQ ID NO: 1 a substitution, preferably a substitution as described herein.

In an alternative aspect, the invention relates to a polypeptide comprising the amino acid sequence shown in SEQ ID NO: 1, wherein said amino acid sequence shown in SEQ ID NO: 1 comprises at 1, 2, 3, 4, 5, 6, 7, 8, 9, 10, or 11 (or even more substitutions such as 12, 13, 14, 15, 16, 17, 18, 19 or 20) amino acid positions corresponding to positions 44, 50, 79, 81, 98, 104, 125, 127, 128, 130 and/or 134 of the linear polypeptide sequence of SEQ ID NO: 1 a substitution, preferably a substitution as described herein. The polypeptide of said alternative aspect is preferably an anticalin which preferably binds CTLA-4, in particular human CTLA-4.

Similarly, the invention relates to a lipocalin mutein derived from NGAL having a cylindrical β-pleated sheet supersecondary structural region comprising eight β-strands connected pair-wise by four loops at one end to define thereby a binding pocket, wherein at least one amino acid of each of at least three of said four loops has been mutated and wherein said lipocalin is effective to bind CTLA-4 as given nonnatural target with detectable affinity. Advantageously, the lipocalin mutein comprises at 1, 2, 3, 4, 5, 6, 7, 8, 9, 10, or 11 amino acid position(s) corresponding to the amino acid at position 44, 50, 79, 81, 98, 104, 125, 127, 128, 130 and/or 134 of the linear polypeptide sequence of SEQ ID NO: 1 a substitution, preferably a substitution as described herein.

The term "position" when used in accordance with the invention means the position of either an amino acid within an amino acid sequence depicted herein or the position of a nucleotide within a nucleic acid sequence depicted herein. The term "corresponding" as used herein also includes that a position is not only determined by the number of the preceding nucleotides/amino acids. Accordingly, the position of a given amino acid in accordance with the invention which may be substituted may very due to deletion or addition of amino acids elsewhere in a (mutant or wild-type) lipocalin. Similarly, the position of a given nucleotide in accordance with the present invention which may be substituted may vary due to deletions or additional nucleotides elsewhere in a mutein or wild type lipocalin 5'-untranslated region (UTR) including the promoter and/or any other regulatory sequences or gene (including exons and introns).

Thus, under a "corresponding position" in accordance with the invention it is preferably to be understood that nucleotides/amino acids may differ in the indicated number but may still have similar neighboring nucleotides/amino acids. Said nucleotides/amino acids which may be exchanged, deleted or added are also comprised by the term "corresponding position".

Specifically, in order to determine whether a nucleotide residue or amino acid residue of the amino acid sequence of a lipocalin different from a NGAL lipocalin mutein of the invention corresponds to a certain position in the nucleotide sequence or the amino acid sequence of a NGAL lipocalin mutein as described, in particular any of SEQ ID NOs: 1 and 12-17 or that having one or more amino acid substitutions at position 44, 50, 79, 81, 98, 104, 125, 127, 128, 130 and/or 134 of the linear polypeptide sequence of SEQ ID NO: 1, a skilled artisan can use means and methods well-known in the art, e.g., alignments, either manually or by using computer programs such as BLAST2.0, which stands for Basic Local Alignment Search Tool or ClustalW or any other suitable program which is suitable to generate sequence alignments. Accordingly, a lipocalin mutein of any of SEQ ID Nos: 1 and 12-17 or that having one or more amino acid substitutions at position 44, 50, 79, 81, 98, 104, 125, 127, 128, 130 and/or 134 of the linear polypeptide sequence of SEQ ID NO: 1 can serve as "subject sequence" or "reference sequence", while the amino acid sequence of a lipocalin different from any of the NGAL muteins described herein serves as "query sequence".

Given the above, a skilled artisan is thus readily in a position to determine which amino acid position mutated in Lcn2 as described herein corresponds to an amino acid of a scaffold other than Lcn2, preferably such as one of those described herein. Specifically, a skilled artisan can align the amino acid sequence of a mutein as described herein, in particular a NGAL mutein (or anticalin) of the invention with the amino acid sequence of a different lipocalin to determine which amino acid(s) of said mutein correspond(s) to the respective amino acid(s) of the amino acid sequence of said different lipocalin. More specifically, a skilled artisan can thus determine which amino acid of the amino acid sequence of said different lipocalin corresponds to the amino acid at position(s) 44, 50, 79, 81, 98, 104, 125, 127, 128, 130 and/or 134 of the linear polypeptide sequence of SEQ ID NO: 1.

Proteins of the invention, which are directed against or specific for CTLA-4, include any number of specific-binding protein muteins that are based on a defined protein scaffold. As used herein, a "mutein," a "mutated" entity (whether protein or nucleic acid) or "mutant" refers to the exchange, deletion, or insertion of one or more nucleotides or amino acids, respectively, compared to the naturally occurring (wild-type) nucleic acid or protein "reference" scaffold. Preferably, the number of nucleotides or amino acids, respectively, that is exchanged, deleted or inserted is 1, 2, 3, 4, 5, 6, 7, 8, 9, 10, 11, 12, 13, 14, 15, 16, 17, 18, 19, 20 or more such as 25, 30, 35, 40, 45 or 50, with 1, 2, 3, 4, 5, 6, 7, 8, 9, 10, or 11 being preferred and 9, 10 or 11 being even more preferred.

However, it is preferred that a lipocalin mutein of the invention is still capable of binding CTLA-4, in particular human CTLA-4.

A protein of the invention can be a mutein of a lipocalin, preferably a lipocalin selected from the group consisting of retinol-binding protein (RBP), bilin-binding protein (BBP), apolipoprotein D (APO D), neutrophil gelatinase associated lipocalin (NGAL), tear lipocalin (TLPC), $\alpha_2$-microglobulin-related protein (A2m), 24p3/uterocalin (24p3), von Ebners gland protein 1 (VEGP 1), von Ebners gland protein 2 (VEGP 2), and Major allergen Can f1 precursor (ALL-1), with NGAL being a preferred lipocalin. As used herein, a "lipocalin" is defined as monomeric protein of approximately 18-20 kDA in weight, having a cylindrical β-pleated sheet supersecondary structural region comprising a plurality of (preferably eight) β-strands connected pair-wise by a plurality of (preferably four) loops at one end to define thereby a binding pocket. It is the diversity of the loops in the otherwise rigid lipocalin scaffold that gives rise to a variety of different binding modes among the lipocalin family members, each capable of accommodating targets of different size, shape, and chemical character (reviewed, e.g., in Flower, D. R. (1996), supra; Flower, D. R. et al. (2000), supra, or Skerra, A. (2000) *Biochim. Biophys. Acta* 1482, 337-350). Indeed, the lipocalin family of proteins have naturally evolved to bind a wide spectrum of ligands, sharing unusually low levels of overall sequence conservation (often with sequence identities of less than 20%) yet retaining a highly conserved overall folding pattern. The correspondence between positions in various lipocalins is well known to one of skill in the art. See, for example, U.S. Pat. No. 7,250,297.

In a preferred embodiment, a protein of the invention is a mutein of Lipocalin 2 (Lcn 2; also known as human neutrophil gelatinase-associated lipocalin, hNGAL, or as sideroca-lin). The term "human neutrophil gelatinase-associated lipocalin" or "hNGAL" or "lipocalin 2" or "Lcn2" as used herein refers to the mature hNGAL with the SWISS-PROT/UniProt Data Bank Accession Number P80188 (Isoform 1). The amino acid sequence shown in SWISS-PROT/UniProt Data Bank Accession Number P80188 may be used as a preferred "reference sequence".

Most preferred, the amino acid sequence shown in SEQ ID NO: 1 (of the Sequence Listing) is used as a "reference sequence". SEQ ID NO: 1 shows a lipocalin mutein that is capable of binding to CTLA-4, in particular human CTLA-4. The mutein shown in SEQ ID NO: 1 was further affinity matured as described in the appended Examples, resulting in lipocalin muteins that bind CTLA-4, in particular human CTLA-4 with an improved affinity. These affinity matured lipocalin muteins are shown in SEQ ID NOs: 12-17. Some of the properties of these affinity matured lipocalin muteins are illustrated in Tables 1-3 (see Examples) and FIG. 4.

The amino acid sequence shown in SEQ ID NO: 1 differs from the Lcn2 wild type sequence (SEQ ID NO: 20) at positions 40, 44, 46, 47, 49, 50, 60, 70, 71, 72, 73, 77, 79, 81, 101, 102, 103, 114, 118, 120, 125, 126, 127, 128, 130, 132, 134, 137 and 145. Accordingly, the lipocalin muteins of the invention that are obtainable by, for example, affinity maturation from the mutein shown in SEQ ID NO: 1, also differ from the wild type Lcn2 (NGAL) amino acid sequence (SEQ ID NO: 20). In particular, said affinity matured lipocalin muteins (shown in SEQ ID NOs: 12-17) differ at positions 40, 44, 46, 47, 49, 50, 60, 70, 71, 72, 73, 77, 79, 81, 98 (only the mutein shown in SEQ ID NO:17), 101, 102, 103, 104 (all, except for the mutein shown in SEQ ID NO: 17), 114, 118, 120, 125, 126, 127 (all, except for the mutein shown in SEQ ID NO:

16), 128, 130, 132, 134, 137 and 145 from the wild type NGAL sequence (SEQ ID NO: 20).

SEQ ID NO:20 shows the mature hNGAL. The terms "reference sequence" and "wild type sequence" (of NGAL) are used interchangeably herein. The mature form of this protein has amino acids 21 to 198 (numbered as 1-178 in the Sequence Listing) of the complete sequence, since a signal peptide of amino acids 1-20 (MPLGLLWLGL ALLGAL-HAQA (SEQ ID NO: 22)) is cleaved off. The protein further has a disulfide bond formed between the amino acid residues at positions 76 and 175 of the mature protein.

Accordingly, also preferred, but less preferred than the most preferred reference sequence SEQ ID NO: 1, the wild type sequence of NGAL shown in SEQ ID NO: 20 could be used as an alternative "reference sequence".

Hence, it is envisaged that the invention relates to a lipocalin which comprises, in addition to one or more substitutions at positions corresponding to positions 44, 50, 79, 81, 98, 104, 125, 127, 128, 130 and/or 134 of the linear polypeptide sequence of hNGAL (SEQ ID NO: 20) or of the linear polypeptide sequence of SEQ ID NO: 1, at one or more positions corresponding to positions 40, 46, 47, 49, 60, 70, 71, 72, 73, 77, 101, 102, 103, 114, 118, 120, 126, 132, 137 and/or 145 of the linear polypeptide sequence of hNGAL (SEQ ID NO: 20) a substitution. More preferably, the latter one or more positions correspond to positions (within one or more so-called loop regions of a lipocalin) 40, 46, 47, 49, 70, 71, 72, 73, 77, 101, 102, 103, 126, 132 and/or 137 of the linear polypeptide sequence of hNGAL (SEQ ID NO: 20)

Similarly, it is envisaged that the invention relates to a lipocalin mutein comprising at one or more positions corresponding to positions 40, 44, 46, 47, 49, 50, 60, 70, 71, 72, 73, 77, 79, 81, 98, 101, 102, 103, 104, 114, 118, 120, 125, 126, 127, 128, 130, 132, 134, 137 and/or 145 of SEQ ID NO: 20 a substitution.

More preferably, the invention relates to a lipocalin mutein comprising at one or more positions (within one or more so-called loop regions of a lipocalin) which correspond to positions 40, 44, 46, 47, 49, 50, 70, 71, 72, 73, 77, 79, 81, 98, 101, 102, 103, 104, 125, 126, 127, 128, 130, 132, 134 and/or 137 of SEQ ID) NO: 20 a substitution.

Generally, when referred to herein a "mutein of a lipocalin" or "lipocalin mutein", in particular a "mutein of Lipocalin 2" or "Lipocalin 2 mutein" of the invention can also be designated as "anticalin". Accordingly, these terms can be equally used herein. Preferably, an anticalin of the invention is different from its naturally occurring counterpart lipocalin and/or from the anticalin shown in SEQ ID NO: 1 in that it differs in at least one amino acid from its naturally occurring counterpart lipocalin and/or from the anticalin shown in SEQ ID NO: 1, respectively. The difference might be an amino acid substitution, deletion and/or addition, with a substitution being preferred. Preferably, an anticalin of the invention differs in at least 1, 2, 3, 4, 5, 6, 7, 8, 9, 10, or 11 or even more amino acid position(s) (such as 12, 13, 14, 15, 16, 17, 18, 19 or 20), preferably it differs at the amino acid positions as described herein. The difference preferably manifests as amino acid substitution.

In this context, the inventors identified a specific group of Lipocalin 2 muteins with mutations at specific positions which show detectable affinity as well as specificity for CTLA-4. Suitable amino acid positions for mutation include sequence positions 44, 50, 79, 81, 98, 104, 125, 127, 128, 130 and/or 134 of the linear polypeptide sequence of SEQ ID NO: 1. The present invention also relates to nucleic acids encoding these proteins.

Other protein scaffolds that can be engineered in accordance with the present invention to provide protein muteins that bind CTLA-4 with detectable affinity include: an EGF-like domain, a Kringle-domain, a fibronectin type I domain, a fibronectin type II domain, a fibronectin type III domain, a PAN domain, a G1a domain, a SRCR domain, a Kunitz/Bovine pancreatic trypsin Inhibitor domain, tendamistat, a Kazal-type serine protease inhibitor domain, a Trefoil (P-type) domain, a von Willebrand factor type C domain, an Anaphylatoxin-like domain, a CUB domain, a thyroglobulin type I repeat, LDL-receptor class A domain, a Sushi domain, a Link domain, a Thrombospondin type I domain, an immunoglobulin domain or a an immunoglobulin-like domain (for example, domain antibodies or camel heavy chain antibodies), a C-type lectin domain, a MAM domain, a von Willebrand factor type A domain, a Somatomedin B domain, a WAP-type four disulfide core domain, a F5/8 type C domain, a Hemopexin domain, an SH2 domain, an SH3 domain, a Laminin-type EGF-like domain, a C2 domain, "Kappabodies" (Ill. et al. "Design and construction of a hybrid immunoglobulin domain with properties of both heavy and light chain variable regions" Protein Eng 10:949-57 (1997)), "Minibodies" (Martin et al. "The affinity-selection of a minibody polypeptide inhibitor of human interleukin-6" EMBO J. 13:5303-9 (1994)), "Diabodies" (Holliger et al. "Diabodies': small bivalent and bispecific antibody fragments" PNAS USA 90:6444-6448 (1993)), "Janusins" (Traunecker et al. "Bispecific single chain molecules (Janusins) target cytotoxic lymphocytes on HIV infected cells" EMBO J. 10:3655-3659 (1991) and Traunecker et al. "Janusin: new molecular design for bispecific reagents" Int J Cancer Suppl 7:51-52 (1992), a nanobody, an adnectin, a tetranectin, a microbody, an affilin, an affibody an ankyrin, a crystallin, a knottin, ubiquitin, a zinc-finger protein, an autofluorescent protein, an ankyrin or ankyrin repeat protein or a leucine-rich repeat protein, an avimer (Silverman, Lu Q, Bakker A, To W, Duguay A, Alba B M, Smith R, Rivas A, Li P, Le H, Whitehorn E, Moore K W, Swimmer C, Perlroth V, Vogt M, Kolkman J, Stemmer W P 2005, Nat Biotech, December; 23(12):1556-61, E-Publication in Nat. Biotech. 2005 Nov. 20 edition); as well as multivalent avimer proteins evolved by exon shuffling of a family of human receptor domains as also described in Silverman J, Lu Q, Bakker A, To W, Duguay A, Alba B M, Smith R, Rivas A, Li P, Le H, Whitehorn E, Moore K W, Swimmer C, Perlroth V, Vogt M, Kolkman J, Stemmer W P, Nat Biotech, December; 23(12):1556-61, E-Publication in Nat. Biotechnology. 2005 Nov. 20 edition).

A protein of the invention may include the wild type (natural) amino acid sequence of the "parental" protein scaffold (such as a lipocalin) outside the mutated amino acid sequence positions; alternatively, a lipocalin mutein may also contain amino acid mutations outside the sequence positions subjected to mutagenesis that do not interfere with the binding activity and the folding of the mutein. Such mutations can be accomplished on a DNA level using established standard methods (Sambrook, J. et al. (2001) *Molecular Cloning: A Laboratory Manual*, 3rd Ed., Cold Spring Harbor Laboratory Press, Cold Spring Harbor, N.Y.). Possible alterations of the amino acid sequence are insertions or deletions as well as amino acid substitutions.

Such substitutions may be conservative, i.e. an amino acid residue is replaced with a chemically similar amino acid residue. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan. One the other hand, it is also possible to introduce non-conservative alterations in the amino acid sequence. In addition, instead of replacing single amino acid residues, it is also possible to either insert or delete one or more continuous amino acids of the primary structure of a parental protein scaffold, where these deletions or insertion result in a stable folded/functional mutein, which can be readily tested by the skilled worker.

The skilled worker will appreciate methods useful to prepare protein muteins contemplated by the present invention but whose protein or nucleic acid sequences are not explicitly disclosed herein. As an overview, such modifications of the amino acid sequence include, e.g., directed mutagenesis of single amino acid positions in order to simplify subcloning of a mutated lipocalin gene or its parts by incorporating cleavage sites for certain restriction enzymes. In addition, these mutations can also be incorporated to further improve the affinity of a lipocalin mutein for a given target. Furthermore, mutations can be introduced to modulate certain characteristics of the mutein such as to improve folding stability, serum stability, protein resistance or water solubility or to reduce aggregation tendency, if necessary. For example, naturally occurring cysteine residues may be mutated to other amino acids to prevent disulphide bridge formation.

Accordingly, the invention also includes functional variants of proteins disclosed herein, which have a threshold sequence identity or sequence homology to a reference protein. By "identity" or "sequence identity" is meant a property of sequences that measures their similarity or relationship. The term "sequence identity" or "identity" as used in the present invention means the percentage of pair-wise identical residues—following (homologous) alignment of a sequence of a polypeptide of the invention with a sequence in question—with respect to the number of residues in the longer of these two sequences. Percent identity is determined by dividing the number of identical residues by the total number of residues and multiplying the product by 100. The term "homology" is used herein in its usual meaning and includes identical amino acids as well as amino acids which are regarded to be conservative substitutions (for example, exchange of a glutamate residue by an aspartate residue) at equivalent positions in the linear amino acid sequence of two proteins.

The percentage of sequence homology or sequence identity can, for example, be determined herein using the program BLASTP, version blastp 2.2.5 (Nov. 16, 2002; cf. Altschul, S. F. et al. (1997) *Nucl. Acids Res.* 25, 3389-3402). In this embodiment the percentage of homology is based on the alignment of the entire polypeptide sequences (matrix: BLOSUM 62; gap costs: 11.1; cutoff value set to $10^{-3}$) including the propeptide sequences, preferably using the wild type protein scaffold as reference in a pairwise comparison. It is calculated as the percentage of numbers of "positives" (homologous amino acids) indicated as result in the BLASTP program output divided by the total number of amino acids selected by the program for the alignment.

It is also possible to deliberately mutate other amino acid sequence positions to cysteine in order to introduce new reactive groups, for example, for the conjugation to other compounds, such as polyethylene glycol (PEG), hydroxyethyl starch (HES), biotin, peptides or proteins, or for the formation of non-naturally occurring disulphide linkages. With respect to a mutein of human Lipocalin 2, exemplary possibilities of such a mutation to introduce a cysteine residue into the amino acid sequence of a lipocalin including human Lipocalin 2 mutein to include the introduction of a cysteine (Cys) residue at least at one of the sequence positions that correspond to sequence positions 14, 21, 60, 84, 88, 116, 141, 145, 143, 146 or 158 of the wild type sequence of hNGAL. In some embodiments where a human Lipocalin 2 mutein of the invention has a sequence in which, in comparison to the sequence of the SWISS-PROT/UniProt Data Bank Accession Number P80188, a cysteine has been replaced by another amino acid residue, the corresponding cysteine may be reintroduced into the sequence. As an illustrative example, a cysteine residue at amino acid position 87 may be introduced in such a case by reverting to a cysteine as originally present in the sequence of SWISS-PROT accession No P80188. The generated thiol moiety at the side of any of the amino acid positions 14, 21, 60, 84, 88, 116, 141, 145, 143, 146 and/or 158 may be used to PEGylate or HESylate the mutein, for example, in order to increase the serum half-life of a respective human Lipocalin 2 mutein.

In some embodiments, a protein according to the invention binds CTLA-4 with a $K_D$ of 100 μM or less, including 5 μM or less, about 500 nM, about 200 nM or less, 100 nM or less, 10 nM or less, 1 nM or less, 0.5 nM or less, 0.3 nM or less, or 0.2 nM or less. A protein of the invention may specifically bind one or more continuous, discontinuous or conformation epitope(s) of the mature, folded bioactive form of CTLA-4.

A protein of the invention preferably binds to CTLA-4 with an affinity by a $K_D$ of about 1 nM or lower. Binding affinities have been found by the present inventors to often be of a $K_D$ of about 1 nM and, in some cases, about 0.8 or 0.6, 0.5, 0.4, 0.3 nM and below. Thus, the lipocalin mutein of the invention are in the picomolar range which is an outstanding property of a binding molecule.

The binding affinity of a protein of the invention (e.g. a mutein of a lipocalin) to a selected target (in the present case, CTLA-4), can be measured (and thereby $K_D$ values of a mutein-ligand complex be determined) by a multitude of methods known to those skilled in the art. Such methods include, but are not limited to, fluorescence titration, competition ELISA, calorimetric methods, such as isothermal titration calorimetry (ITC), and surface plasmon resonance (BIAcore). Such methods are well established in the art and examples thereof are also detailed below.

The amino acid sequence of a protein of the invention may have a high sequence identity to mature human Lipocalin 2 or other lipocalins. In this context, a protein of the invention may have at least 70%, at least 75%, at least 80%, at least 82%, at least 85%, at least 87%, at least 90% identity, including at least 95% identity to a protein selected from the group consisting of the sequence of SEQ ID NOS: 1 and 12-17.

The invention also includes structural homologues of the proteins selected from the group consisting of the sequence of SEQ ID NOS: 1 and 12-17, which have an amino acid sequence homology or sequence identity of more than about 60%, preferably more than 65%, more than 70%, more than 75%, more than 80%, more than 85%, more than 90%, more than 92% and most preferably more than 95% in relation thereto.

The terms "cytotoxic T lymphocyte-associated antigen-4", "CTLA-4", "CTLA4", "CTLA-4 antigen" and "CD152" (see, e.g., Murata (1999) Am. J. Pathol. 155:453-460) are used interchangeably, and include variants, isoforms, species homologs of human CTLA-4, and analogs having at least one common epitope with CTLA-4 (see, e.g., Balzano (1992) Int. J. Cancer Suppl. 7:28-32). Accordingly, lipocalin muteins of the invention may, in certain cases, cross-react with CTLA-4 from species other than human such as cynomolgus monkey or mouse. The amino acid sequence of human CTLA-4 is disclosed at Genbank Accession Number NP_005205. The region of amino acids 1-37 is the leader peptide; 38-161 is the extracellular V-like domain; 162-187 is the transmembrane domain; and 188-223 is the cytoplasmic domain. The nucleotide sequence of human CTLA-4 mRNA is disclosed at NM_005214. Variants of the nucleotide sequence have been reported, including a G to A transition at position 49, a C to T transition at position 272, and an A to G transition at position 439. The amino acid sequence of mouse CTLA-4 is disclosed at Genbank Accession Number NP_033973. The region of amino acids 1-35 is the leader peptide. The term "CTLA-4" includes variants, isoforms, homologs, orthologs and paralogs. For example, lipocalin muteins specific for CTLA-4 may, in certain cases, cross-react with CTLA-4 from species other than human. The term "human CTLA-4" refers to human sequence CTLA-4, such as the complete amino acid sequence of human CTLA-4 having Genbank Accession Number NP_005205. The human CTLA-4 sequence may differ from human CTLA-4 of Genbank Accession Number NP_005205 by having, for example, conserved mutations or mutations in non-conserved regions and the CTLA-4 has substantially the same biological function as the human CTLA-4 of Genbank Accession Number NP_005205. For example, a biological function of human CTLA-4 is having an epitope in the extracellular domain of CTLA-4 that is specifically bound by a lipocalin mutein of the invention or a biological function of human CTLA-4 is modulation of T cell activity. A particular human CTLA-4 sequence will generally be at least 90% identical in amino acids sequence to human CTLA-4 of Genbank Accession Number NP_005205 and contains amino acid residues that identify the amino acid sequence as being human when compared to CTLA-4 amino acid sequences of other species (e.g., murine). In certain cases, a human CTLA-4 may be at least 95%, or even at least 96%, 97%, 98%, or 99% identical in amino acid sequence to CTLA-4 of Genbank Accession Number NP_005205. In certain embodiments, a human CTLA-4 sequence will display no more than 10 amino acid differences from the CTLA-4 of Genbank Accession Number NP_005205. In certain embodiments, the human CTLA-4 may display no more than 5, or even no more than 4, 3, 2, or 1 amino acid difference from the CTLA-4 of Genbank Accession Number NP_005205. Percent identity can be determined as described herein.

In line with the above, a protein of the invention preferably acts as an antagonist of CTLA-4. In some embodiments, a protein of the invention (e.g., a human Lipocalin 2 mutein) may act as an antagonist of CTLA-4 by inhibiting the ability of CTLA-4 to bind to or otherwise interact with its cognate ligand B7.1 (CD80) and/or B7.2 (CD86).

In yet another aspect, the present invention includes various lipocalin muteins, including muteins of human Lipocalin 2 that specifically bind CTLA-4. In this sense, CTLA-4 can be regarded a non-natural ligand of wild type human Lipocalin 2, where "non-natural ligand" refers to a compound that does not bind to wildtype lipocalins, including human Lipocalin 2 under physiological conditions. By engineering wildtype lipocalins such as human Lipocalin 2 with mutations at certain positions, the present inventors have demonstrated that high affinity and high specificity for a non-natural ligand is possible. In one aspect at least at 1, 2, 3, 4, 5, 6, 7, 8, 9, 10, or 11 nucleotide triplet(s) encoding for any of the sequence positions 44, 50, 79, 81, 98, 104, 125, 127, 128, 130 and/or 134 of the linear polypeptide sequence of SEQ ID NO: 1, or other parallel sites on lipocalins, a random mutagenesis can be carried out by allowing substitution at this positions by a subset of nucleotide triplets.

Further, the lipocalins can be used to generate muteins that have a mutated amino acid residue at any one or more, including at least at any two, three, four, five, six, seven, eight, nine, ten, or eleven, of the sequence positions of the sequence positions corresponding to the sequence positions 44, 50, 79, 81, 98, 104, 125, 127, 128, 130 and/or 134 of the linear polypeptide sequence of SEQ ID NO: 1.

A substitution at sequence position 44 may for example be a substitution Glu 44→Asp, Gln, Ser or Leu. A substitution at sequence position 50 may for example be a substitution Lys 50→Asn, Asp, Leu, Pro or Arg. A substitution at sequence position 79 may for example be a substitution Trp 79→Thr, Pro, Ser. A substitution at sequence position 81 may for example be a substitution Arg 81→Ala. A substitution at sequence position 98 may for example be a substitution Lys 98→Arg. A substitution at sequence position 104 may for example be a substitution Thr 104→Trp, Val, Glu, or Thr. A substitution at sequence position 125 may for example be a substitution Lys 125→Leu, His, or Tyr. A substitution at sequence position 127 may for example be a substitution Ser 127→Glu, or Asp. A substitution at sequence position 128 may for example be a substitution Gln 128→Asp, Thr, or Ser. A substitution at sequence position 130 may for example be a substitution Arg 130→Ala, Tyr, or Asp. A substitution at sequence position 134 may for example be a substitution Lys 134→Ala or Ser.

A substitution at sequence position Ala 40 may for example be a substitution Ala 40→R or Y. A substitution at sequence position 46 may for example be a substitution Lys 46→Q or R. A substitution at sequence position 47 may for example be a substitution Asp 47→H or Y. A substitution at sequence position 49 may for example be a substitution Gln 49→M. A substitution at sequence position 60 may for example be a substitution Glu 60→Gly. A substitution at sequence position 70 may for example be a substitution Leu 70→I. A substitution at sequence position 71 may for example be a substitution Phe 71→S or L. A substitution at sequence position 72 may for example be a substitution Arg 72→S, P or D. A substitution at sequence position 73 may for example be a substitution Lys 73→H or T. A substitution at sequence position 77 may for example be a substitution Asp77→E or L. A substitution at sequence position 101 may for example be a substitution Pro 101→G or R. A substitution at sequence position 102 may for example be a substitution Gly 102→D or M. A substitution at sequence position 103 may for example be a substitution Leu 103→K or D. A substitution at sequence position 114 may for example be a substitution Asn 114→Asp. A substitution at sequence position 118 may for example be a substitution His 118→Tyr. A substitution at sequence position 120 may for example be a substitution Met 120→Val. A substitution at sequence position 126 may for example be a substitution Val 126→A. A substitution at sequence position 132 may for example be a substitution Tyr 132→S, F or H. A substitution at sequence position 137 may for example be a substitution Leu→I. A substitution at sequence position 145 may for example be a substitution Thr 145→Ala.

Noteworthy, any of the amino acids that substitutes in a desired lipocalin the corresponding amino acid in the reference sequence can be exchanged by a corresponding conservative amino acid. In particular, conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan.

In one embodiment, a mutein of the invention, which binds to CTLA-4 includes the following amino acid replacements:

(a) Glu 44→Asp; Lys 50→Asn; Trp 79→Thr; Arg 81→Ala; Lys 125→Leu; Ser 127→Glu; Gln 128→Asp; Arg 130→Ala; Lys 134→Ala;
(b) Glu 44→Asp; Lys 50→Asp; Trp 79→Pro; Arg 81→Ala; Thr 104→Trp; Lys 125→His; Ser 127→Asp; Gln 128→Thr; Arg 130→Tyr; Lys 134→Ser;
(c) Glu 44→Gln; Lys 50→Leu; Trp 79→Pro; Arg 81→Ala; Thr 104→Val; Lys 125→His; Ser 127→Asp; Gln 128→Thr; Arg 130→Tyr; Lys 134→Ser;
(d) Glu 44→Asp; Lys 50→Pro; Trp 79→Pro; Arg 81→Ala; Thr 104→Trp; Lys 125→His; Ser 127→Asp; Gln 128→Ser; Arg 130→Tyr; Lys 134→Ser;
(e) Glu 44→Ser; Lys 50→Arg; Trp 79→Thr; Arg 81→Ala; Thr 104→Trp; Lys 125→His; Ser 127→Asp; Gln 128→Thr; Arg 130→Tyr; Lys 134→Ser;
(f) Glu 44→Ser; Lys 50→Pro; Trp 79→Ser; Arg 81→Ala; Thr 104→Glu; Lys 125→Tyr; Gln 128→Asp; Arg 130→Asp; Lys 134→Ser; and
(g) Glu 44→Leu; Lys 50→Pro; Trp 79→Pro; Arg 81→Ala; Lys 98→Arg; Lys 125→His; Ser 127→Asp; Gln 128→Thr; Arg 130→Tyr; Lys 134→Ser.
(h) In addition, the muteins referred to in (a) to (g) may have the amino acid substitutions in comparison to wild type hNGAL (Lcn2) which are apparent from the sequence alignment shown in FIG. 3. These substitutions may be at position 40, 46, 47, 49, 60, 70, 71, 72, 73, 77, 101, 102, 103, 114, 118, 120, 126, 132, 137 and/or 145. For example, when the wild type sequence has at position 40 an Ala residue, then each of the muteins has an Arg residue at the corresponding position.

The numbering is preferably in relation to the linear polypeptide sequence of SEQ ID NO: 20, more preferably in relation to the linear polypeptide sequence of SEQ ID NO: 1. Accordingly, given the teaching of the invention as described above, a skilled artisan can readily determine which amino acids in a lipoprotein correspond to those described above in (a) to (h) in the preferred reference sequence of NGAL (SEQ ID NO: 20) or in the more preferred reference sequence of SEQ ID NO: 1 so as to mutate said amino acids in said lipoprotein.

It is also noted that the complex formation between the respective mutein and its ligand is influenced by many different factors such as the concentrations of the respective binding partners, the presence of competitors, pH and the ionic strength of the buffer system used, and the experimental method used for determination of the dissociation constant $K_D$ (for example fluorescence titration, competition ELISA or surface plasmon resonance, just to name a few) or even the mathematical algorithm which is used for evaluation of the experimental data.

Therefore, it is also clear to the skilled person that the $K_D$ values (dissociation constant of the complex formed between the respective mutein and its target/ligand) may vary within a certain experimental range, depending on the method and experimental setup that is used for determining the affinity of a particular lipocalin mutein for a given ligand. This means that there may be a slight deviation in the measured $K_D$ values or a tolerance range depending, for example, on whether the $K_D$ value was determined by surface plasmon resonance (Biacore), by competition ELISA, or by "direct ELISA."

In one embodiment, the muteins disclosed herein can be linked, either N- or C-terminal to a fusion partner which is preferably a protein, or a protein domain or a peptide. Examples of a fusion partner is an affinity tag such as pentahistidine tag (SEQ ID NO: 37), a hexahistidine tag (SEQ ID NO: 23) or a steptavidin tag (e.g. Streptag®). Thus, the present application encompasses also all explicitly and generic described muteins equipped with such tags.

The term "fragment" as used in the present invention in connection with the feature lipocalin mutein fragment relates to proteins or peptides derived from full-length mature Lcn 2 that are N-terminally and/or C-terminally shortened, i.e. lacking at least one of the N-terminal and/or C-terminal amino acids. Such fragments include preferably at least 10, more preferably 20, most preferably 30 or more consecutive amino acids of the primary sequence of mature Lcn 2 and are usually detectable in an immunoassay of mature Lcn 2. The word "detect" or "detecting" as used herein is understood both on a quantitative and a qualitative level, as well as a combination thereof. It thus includes quantitative, semi-quantitative and qualitative measurements of a molecule of interest. Accordingly, the presence or absence of a molecule such as CTLA-4, e.g. in a sample, as well as its concentration or level may be determined.

Also included in the scope of the present invention are the above muteins, which have been altered with respect to their immunogenicity, to reduce any detected immunogenicity by employing methods known to the skilled worker in the field.

Cytotoxic T-cells recognize peptide antigens on the cell surface of an antigen-presenting cell in association with a class I major histocompatibility complex (MHC) molecule. The ability of the peptides to bind to MHC molecules is allele specific and correlates with their immunogenicity. To reduce the immunogenicity of a given protein, the ability to predict which peptides in a protein have the potential to bind to a given MHC molecule is of great value. Approaches that employ a computational threading approach to identify potential T-cell epitopes have been previously described to predict the binding of a given peptide sequence to MHC class I molecules (Altuvia et al. (1995) *J. Mol. Biol.* 249: 244-250). Such an approach may also be utilized to identify potential T-cell epitopes in the muteins of the invention and to make, depending on its intended use, a selection of a specific mutein on the basis of its predicted immunogenicity. It may be furthermore possible to subject peptide regions that have been predicted to contain T-cell epitopes to additional mutagenesis to reduce or eliminate these T-cell epitopes and thus minimize immunogenicity. The removal of amphipathic epitopes from genetically engineered antibodies has been described (Mateo et al. (2000) *Hybridoma* 19(6):463-471) and may be adapted to the muteins of the present invention. The muteins thus obtained may possess a minimized immunogenicity, which is desirable for their use in therapeutic and diagnostic applications, such as those described below.

For some applications, it is also useful to employ the muteins of the invention in a conjugated form. The conjugation can be carried out using any conventional coupling method known in the art.

The term "organic molecule" or "small organic molecule" as used herein for the non-natural target denotes an organic molecule comprising at least two carbon atoms, but preferably not more than 7 or 12 rotatable carbon bonds, having a molecular weight in the range between 100 and 2000 Dalton, preferably between 100 and 1000 Dalton, and optionally including one or two metal atoms.

In general, it is possible to label a lipocalin mutein described herein with any appropriate chemical substance or enzyme, which directly or indirectly generates a detectable compound or signal in a chemical, physical, optical, or enzymatic reaction. An example for a physical reaction and at the same time optical reaction/marker is the emission of fluorescence upon irradiation. Alkaline phosphatase, horseradish peroxidase or β-galactosidase are examples of enzyme labels (and at the same time optical labels) which catalyze the formation of chromogenic reaction products. In general, all labels commonly used for antibodies (except those exclusively used with the sugar moiety in the Fc part of immunoglobulins) can also be used for conjugation to the muteins of the present invention. The muteins of the invention may also be conjugated with any suitable therapeutically active agent, e.g., for the targeted delivery of such agents to a given cell, tissue or organ or for the selective targeting of cells, e.g., of tumor cells without affecting the surrounding normal cells. Examples of such therapeutically active agents include radionuclides, toxins, small organic molecules, and therapeutic peptides (such as peptides acting as agonists/antagonists of a cell surface receptor or peptides competing for a protein binding site on a given cellular target). Examples of suitable toxins include, but are not limited to pertussis-toxin, diphtheria toxin, ricin, saporin, pseudomonas exotoxin, calicheamicin or a derivative thereof, a taxoid, a maytansinoid, a tubulysin or a dolastatin analogue. The dolastatin analogue may be auristatin E, monomethylauristatin E, auristatin PYE and auristatin PHE. Examples of cytostatic agent include, but are not limited to Cisplatin, Carboplatin, Oxaliplatin, 5-Fluorouracil, Taxotere (Docetaxel), Paclitaxel, Anthracycline (Doxorubicin), Methotrexate, Vinblastin, Vincristine, Vindesine, Vinorelbine, Dacarbazine, Cyclophosphamide, Etoposide, Adriamycine, Camptotecine, Combretatastin A-4 related compounds, sulfonamides, oxadiazolines, benzo[b]thiophenessynthetic spiroketal pyrans, monotetrahydrofuran compounds, curacin and curacin derivatives, methoxyestradiol derivatives and Leucovorin. The lipocalin muteins of the invention may also be conjugated with therapeutically active nucleic acids such as antisense nucleic acid molecules, small interfering RNAs, micro RNAs or ribozymes. Such conjugates can be produced by methods well known in the art.

In one embodiment, the muteins of the invention may also be coupled to a targeting moiety that targets a specific body region in order to deliver the inventive muteins to a desired region or area within the body. One example wherein such modification may be desirable is the crossing of the blood-brain-barrier. In order to cross the blood-brain barrier, the muteins of the invention may be coupled to moieties that facilitate the active transport across this barrier (see Gaillard P J, et al. (2005) *International Congress Series*. 1277, 185-198 or Gaillard P J, et al. (2005) *Expert Opin Drug Deliv*. 2(2), 299-309). Such compounds are for example available under the trade name 2B-Trans™ (to-BBB technologies BV, Leiden, NL). Other exemplary targeting molecules to which the muteins of the present invention may be coupled include antibodies, antibody fragments or lipocalin muteins with affinity for a desired target molecule. The target molecule of the targeting moieties may, for example, be a cell-surface antigen. Cell-surface antigens may be specific for a cell or tissue type, such as, for example, cancer cells. Illustrative examples of such cell surface proteins are HER-2 or proteoglycans such as NEU-2.

As indicated above, a mutein of the invention may in some embodiments be conjugated to a compound that extends the serum half-life of the mutein (in this regard see also PCT publication WO 2006/56464 where such conjugation strategies are described with references to muteins of human neutrophil gelatinase-associated lipocalin with binding affinity for CTLA-4). The compound that extends the serum half-life may be a polyalkylene glycol molecule, such as polyethylene (PEG) or an activated derivative thereof; hydroxyethyl starch, fatty acid molecules, such as palmitic acid (Vajo & Duckworth (2000) *Pharmacol. Rev.* 52, 1-9), an Fc part of an immunoglobulin, a $C_H3$ domain of an immunoglobulin, a $C_H4$ domain of an immunoglobulin, albumin or a fragment thereof, an albumin binding peptide, an albumin binding protein, transferrin, or the tag Pro-Ala-Ser, to name only a few. The albumin binding protein may be a bacterial albumin binding protein, an antibody, an antibody fragment including domain antibodies (see U.S. Pat. No. 6,696,245, for example), or a lipocalin mutein with binding activity for albumin. Accordingly, suitable conjugation compounds for extending the half-life of a lipocalin mutein of the invention include albumin (Osborn et al. (2002) *J. Pharmacol. Exp. Ther.* 303, 540-548), or an albumin binding protein, for example, a bacterial albumin binding domain, such as the one of streptococcal protein G (Kñig, T. and Skerra, A. (1998) *J. Immunol. Methods* 218, 73-83). Other examples of albumin binding peptides that can be used as conjugation partner are, for instance, those having a Cys-$Xaa_1$-$Xaa_2$-$Xaa_3$-$Xaa_4$-Cys consensus sequence, wherein $Xaa_1$ is Asp, Asn, Ser, Thr, or Trp; $Xaa_2$ is Asn, Gln, His, Ile, Leu, or Lys; $Xaa_3$ is Ala, Asp, Phe, Trp, or Tyr; and $Xaa_4$ is Asp, Gly, Leu, Phe, Ser, or Thr as described in US patent application 2003/0069395 or Dennis et al. (Dennis et al. (2002) *J. Biol. Chem.* 277, 35035-35043).

In other embodiments, albumin itself or a biological active fragment of albumin can be used as compound of a lipocalin mutein of the invention that extends the serum half-life of the mutein. The term "albumin" includes all mammal albumins such as human serum albumin or bovine serum albumin or rat albumin. The albumin or fragment thereof can be recombinantly produced as described in U.S. Pat. No. 5,728,553 or European patent applications EP 0 330 451 and EP 0 361 991. Recombinant human albumin (Recombumin®) for use as a protein stabilizer is for example available from Novozymes Delta Ltd. (Nottingham, UK).

If the albumin-binding protein is an antibody fragment it may be a domain antibody. Domain Antibodies (dAbs) are engineered to allow precise control over biophysical properties and in vivo half-life to create the optimal safety and efficacy product profile. Domain Antibodies are for example commercially available from Domantis Ltd. (Cambridge, UK and MA, USA).

Using transferrin as a moiety to extend the serum half-life of the muteins of the invention, the muteins can be genetically fused to the N or C terminus, or both, of non-glycosylated transferrin. Non-glycosylated transferrin has a half-life of 14-17 days, and a transferrin fusion protein will similarly have an extended half-life. The transferrin carrier also provides high bioavailability, biodistribution and circulating stability. This technology is commercially available from BioRexis (BioRexis Pharmaceutical Corporation, PA, USA). Recombinant human transferrin (DeltaFerrin™) for use as a protein stabilizer is also commercially available from Novozymes Delta Ltd. (Nottingham, UK).

If an Fc part of an immunoglobulin is used for the purpose to prolong the serum half-life of the muteins of the invention, the SynFusion™ technology, commercially available from Syntonix Pharmaceuticals, Inc (MA, USA), may be used. The use of this Fc-fusion technology allows the creation of longer-acting biopharmaceuticals and may for example comprise two copies of the mutein linked to the Fc region of an antibody to improve pharmacokinetics, solubility, and production efficiency.

Yet another alternative to prolong the half-life of a mutein of the invention is to fuse the N- or C-terminus of a mutein of the invention to long, unstructured, flexible glycine-rich sequences (for example poly-glycine with about 20 to 80 consecutive glycine residues). This approach disclosed in WO 2007/038619, for example, has also been term "rPEG" (recombinant PEG).

If polyalkylene glycol is used as compound that extends the half-life of the mutein, the polyalkylene glycol can be substituted or unsubstituted. It can also be an activated polyalkylene derivative. Examples of suitable compounds are polyethylene glycol (PEG) molecules as described in WO 99/64016, in U.S. Pat. No. 6,177,074 or in U.S. Pat. No. 6,403,564 in relation to interferon, or as described for other proteins such as PEG-modified asparaginase, PEG-adenosine deaminase (PEG-ADA) or PEG-superoxide dismutase (see for example, Fuertges et al. (1990) "The Clinical Efficacy of Poly(Ethylene Glycol)-Modified Proteins" *J. Control. Release* 11, 139-148). The molecular weight of such a polymer, preferably polyethylene glycol, may range from about 300 to about 70.000 Dalton, including, for example, polyethylene glycol with a molecular weight of about 10.000, of about 20.000, of about 30.000 or of about 40.000 Dalton. Moreover, e.g. as described in U.S. Pat. No. 6,500,930 or 6,620,413, carbohydrate oligo- and polymers such as starch or hydroxyethyl starch (HES) can be conjugated to a mutein of the invention for the purpose of serum half-life extension.

In another embodiment, in order to provide suitable amino acid side chains for conjugating one of the above compounds to the muteins of the invention artificial amino acids may be introduced by mutagenesis. Generally, such artificial amino acids are designed to be more reactive and thus to facilitate the conjugation to the desired moiety. One example of such an artificial amino acid that may be introduced via an artificial tRNA is para-acetyl-phenylalanine.

For several applications of the muteins disclosed herein, it may be advantageous to use them in the form of fusion proteins. In some embodiments, the inventive mutein is fused at its N-terminus and/or it's C-terminus to a protein, a protein domain or a peptide such as a signal sequence and/or an affinity tag.

For pharmaceutical applications, a mutein of the invention may be fused to a fusion partner that extends the in vivo serum half-life of the mutein (see again PCT publication WO 2006/56464 where suitable fusion partner are described with references to muteins of human neutrophile gelatinase-associated lipocalin with binding affinity for CTLA-4). Similar to the conjugated compounds described above, the fusion partner may be an Fc part of an immunoglobulin, a $C_H3$ domain of an immunoglobulin, a $C_H4$ domain of an immunoglobulin, albumin, an albumin binding peptide or an albumin binding protein, to name only a few. Again, the albumin binding protein may be a bacterial albumin binding protein or a lipocalin mutein with binding activity for albumin. Accordingly, suitable fusion partners for extending the half-life of a lipocalin mutein of the invention include albumin (Osborn, B. L. et al. (2002) supra J. Pharmacol. Exp. Ther. 303, 540-548), or an albumin binding protein, for example, a bacterial albumin binding domain, such as streptococcal protein G (König, T. and Skerra, A. (1998) supra *J. Immunol. Methods* 218, 73-83). The albumin binding peptides described in Dennis et al, supra (2002) or US patent application 2003/0069395 having a Cys-$Xaa_1$-$Xaa_2$-$Xaa_3$-$Xaa_4$-Cys consensus sequence, wherein $Xaa_1$ is Asp, Asn, Ser, Thr, or Trp; $Xaa_2$ is Asn, Gln, His, Ile, Leu, or Lys; $Xaa_3$ is Ala, Asp, Phe, Trp, or Tyr; and $Xaa_4$ is Asp, Gly, Leu, Phe, Ser, or Thr can also be used as fusion partner. It is also possible to use albumin itself or a biological active fragment of albumin as fusion partner of a lipocalin mutein of the invention. The term "albumin" includes all mammal albumins such as human serum albumin or bovine serum albumin or rat serum albumin. The recombinant production of albumin or fragments thereof is well known in the art and for example described in U.S. Pat. No. 5,728,553, European patent application EP 0 330 451 or EP 0 361 991.

The fusion partner may confer new characteristics to the inventive lipocalin mutein such as enzymatic activity or binding affinity for other molecules. Examples of suitable fusion proteins are alkaline phosphatase, horseradish peroxidase, gluthation-5-transferase, the albumin-binding domain of protein G, protein A, antibody fragments, oligomerization domains, lipocalin muteins of same or different binding specificity (which results in the formation of "duocalins," cf. Schlehuber, S., and Skerra, A. (2001), Duocalins, engineered ligand-binding proteins with dual specificity derived from the lipocalin fold (*Biol. Chem.* 382, 1335-1342), or toxins.

In particular, it may be possible to fuse a lipocalin mutein of the invention with a separate enzyme active site such that both "components" of the resulting fusion protein together act on a given therapeutic target. The binding domain of the lipocalin mutein attaches to the disease-causing target, allowing the enzyme domain to abolish the biological function of the target.

Affinity tags such as the Strep-Tag® or Strep-Tag® II (Schmidt, T. G. M. et al. (1996), *J. Mol. Biol.* 255, 753-766), the myc-tag, the FLAG-tag, the His6-tag (SEQ ID NO: 23) or the HA-tag or proteins such as glutathione-S-transferase also allow easy detection and/or purification of recombinant proteins are further examples of preferred fusion partners. Finally, proteins with chromogenic or fluorescent properties such as the green fluorescent protein (GFP) or the yellow fluorescent protein (YFP) are suitable fusion partners for a lipocalin mutein of the invention as well.

The term "fusion protein" as used herein also includes lipocalin muteins according to the invention containing a signal sequence. Signal sequences at the N-terminus of a polypeptide direct this polypeptide to a specific cellular compartment, for example the periplasm of *E. coli* or the endoplasmatic reticulum of eukaryotic cells. A large number of signal sequences is known in the art. A preferred signal sequence for secretion a polypeptide into the periplasm of *E. coli* is the OmpA-signal sequence.

The present invention also relates to nucleic acid molecules (DNA and RNA) comprising nucleotide sequences coding for muteins as described herein. Since the degeneracy of the genetic code permits substitutions of certain codons by other codons specifying the same amino acid, the invention is not limited to a specific nucleic acid encoding a mutein of the invention but includes all nucleic acid molecules comprising nucleotide sequences encoding a functional mutein.

A nucleic acid molecule disclosed in this application may be "operably linked" to a regulatory sequence (or regulatory sequences) to allow expression of this nucleic acid molecule.

A nucleic acid molecule, such as DNA, is referred to as "capable of expressing a nucleic acid molecule" or capable "to allow expression of a nucleotide sequence" if it includes sequence elements which contain information regarding to transcriptional and/or translational regulation, and such sequences are "operably linked" to the nucleotide sequence encoding the polypeptide. An operable linkage is a linkage in which the regulatory sequence elements and the sequence to be expressed are connected in a way that enables gene expression. The precise nature of the regulatory regions necessary for gene expression may vary among species, but in general these regions include a promoter which, in prokaryotes, contains both the promoter per se, i.e. DNA elements directing the initiation of transcription, as well as DNA elements which, when transcribed into RNA, will signal the initiation of translation. Such promoter regions normally include 5' non-coding sequences involved in initiation of transcription and translation, such as the −35/−10 boxes and the Shine-Dalgarno element in prokaryotes or the TATA box, CAAT sequences, and 5'-capping elements in eukaryotes. These regions can also include enhancer or repressor elements as well as translated signal and leader sequences for targeting the native polypeptide to a specific compartment of a host cell.

In addition, the 3' non-coding sequences may contain regulatory elements involved in transcriptional termination, polyadenylation or the like. If, however, these termination sequences are not satisfactory functional in a particular host cell, then they may be substituted with signals functional in that cell.

Therefore, a nucleic acid molecule of the invention can include a regulatory sequence, preferably a promoter sequence. In another preferred embodiment, a nucleic acid molecule of the invention includes a promoter sequence and a transcriptional termination sequence. Suitable prokaryotic promoters are, for example, the tet promoter, the lacUV5 promoter or the T7 promoter. Examples of promoters useful for expression in eukaryotic cells are the SV40 promoter or the CMV promoter.

The nucleic acid molecules of the invention can also be part of a vector or any other kind of cloning vehicle, such as a plasmid, a phagemid, a phage, a baculovirus, a cosmid or an artificial chromosome such as a YAC or BAC.

The DNA molecule encoding lipocalin muteins of the invention, and in particular a cloning vector containing the coding sequence of such a lipocalin mutein can be transformed into a host cell capable of expressing the gene. Transformation can be performed using standard techniques (Sambrook, J. et al. (2001), supra).

Thus, the invention is also directed to a host cell containing a nucleic acid molecule as disclosed herein.

The invention also relates to a method for the production of a mutein of the invention, wherein the mutein, a fragment of the mutein or a fusion protein of the mutein and another polypeptide is produced starting from the nucleic acid coding for the mutein by means of genetic engineering methods. The method can be carried out in vivo, the mutein can for example be produced in a bacterial or eucaryotic host organism and then enriched, purified or isolated from this host organism or its culture. It is also possible to produce a protein in vitro, for example by use of an in vitro translation system. The term "enriched" means that the mutein or a functional fragment thereof constitutes a significantly higher fraction of the total protein present in a sample or solution of interest than in a sample or solution from which it was taken. Enrichment may for instance include the isolation of a certain fraction from a cell extract. This may be obtained by standard techniques such as centrifugation. Examples of other means of enrichment are filtration or dialysis, which may for instance be directed at the removal of undesired molecules below a certain molecular weight, or a precipitation using organic solvents or ammonium sulphate. Purification may for instance include a chromatographic technique, for example gel filtration, ion exchange chromatography, affinity purification, hydrophobic interaction chromatography or hydrophobic charge induction chromatography. Another example for purification is an electrophoretic technique, such as preparative capillary electrophoresis. Isolation may include the combination of similar methods. As used herein, "substantially pure" or "substantially purified" means a compound or species that is the predominant species present (i.e., on a molar basis it is more abundant than any other individual species in the composition). In some embodiments, a substantially purified composition is a composition in which the species includes at least about 50 percent (on a molar basis) of all molecular or, as applicable, all macromolecular species present. In certain embodiments, a substantially pure composition will have more than about 80%, about 85%, about 90%, about 95%, or about 99% of all molecular or, as applicable, all macromolar species present in the composition.

When producing the mutein in vivo, a nucleic acid encoding a mutein of the invention is introduced into a suitable bacterial or eukaryotic host organism by means of recombinant DNA technology (as already outlined above). For this purpose, the host cell is first transformed with a cloning vector comprising a nucleic acid molecule encoding a mutein of the invention using established standard methods (Sambrook, J. et al. (1989), supra). The host cell is then cultured under conditions, which allow expression of the heterologous DNA and thus the synthesis of the corresponding polypeptide. Subsequently, the polypeptide is recovered either from the cell or from the cultivation medium.

In one aspect, the present invention relates to a method for the generation of a mutein which binds CTLA-4, comprising:

subjecting a nucleic acid molecule encoding a lipocalin to mutagenesis, resulting in one or more mutein nucleic acid molecule(s).

The method can further include:

expressing the one more mutein nucleic acid molecule(s) obtained in (a) in a suitable expression system, bringing the plurality of muteins into contact with at least a fragment (including a soluble form) or a mature form of CTLA-4, and enriching the one or more mutein(s) having a detectable binding affinity for a given target by means of selection and/or isolation.

The term "mutagenesis" as used herein means that the experimental conditions are chosen such that the amino acid naturally occurring at a given sequence position of the lipocalin, including Lcn 2 (hNGAL; Swiss-Prot data bank entry P80188) can be substituted by at least one amino acid that is not present at this specific position in the respective natural polypeptide sequence. The term "mutagenesis" also includes the (additional) modification of the length of sequence segments by deletion or insertion of one or more amino acids. Thus, it is within the scope of the invention that, for example, one amino acid at a chosen sequence position is replaced by a stretch of three random mutations, leading to an insertion of two amino acid residues compared to the length of the respective segment of the wild type protein. Such an insertion of deletion may be introduced independently from each other in any of the peptide segments that can be subjected to mutagenesis in the invention. In one exemplary embodiment of the invention, an insertion of several mutations may be introduced into the loop AB of the chosen lipocalin scaffold (cf. International Patent Application WO 2005/019256 which is incorporated by reference its entirety herein). The term "random mutagenesis" means that no predetermined single amino acid (mutation) is present at a certain sequence position but that at least two amino acids can be incorporated with a certain probability at a predefined sequence position during mutagenesis.

In one non-limiting approach, the coding sequence of human Lipocalin 2 can be used as a starting point for the mutagenesis of the peptide segments selected in the present invention. Alternatively, the lipocalin mutein of SEQ ID NO: 1 may be used. For the mutagenesis of the recited amino acid positions, the person skilled in the art has at his disposal the various established standard methods for site-directed mutagenesis (Sambrook, J. et al. (2001), supra). A commonly used technique is the introduction of mutations by means of PCR (polymerase chain reaction) using mixtures of synthetic oligonucleotides, which bear a degenerate base composition at the desired sequence positions. Other similar techniques are well known to those of skill in the art.

The nucleic acid molecules defined above can be connected by ligation with the missing 5'- and 3'-sequences of a nucleic acid encoding a lipocalin polypeptide and/or the vector, and can be cloned in a known host organism. A multitude of established procedures are available for ligation and cloning (Sambrook, J. et al. (2001), supra). For example, recognition sequences for restriction endonucleases also present in the sequence of the cloning vector can be engineered into the sequence of the synthetic oligonucleotides. Thus, after amplification of the respective PCR product and enzymatic cleavage the resulting fragment can be easily cloned using the corresponding recognition sequences.

Longer sequence segments within the gene coding for the protein selected for mutagenesis can also be subjected to random mutagenesis via known methods, for example by use of the polymerase chain reaction under conditions of increased error rate, by chemical mutagenesis or by using bacterial mutator strains. Such methods can also be used for further optimization of the target affinity or specificity of a lipocalin mutein. Mutations possibly occurring outside the segments of experimental mutagenesis are often tolerated or can even prove to be advantageous, for example if they contribute to an improved folding efficiency or folding stability of the lipocalin mutein.

In a further embodiment, the method includes subjecting the nucleic acid molecule to mutagenesis at nucleotide triplets coding for at least any 1, 2, 3, 4, 5, 6, 7, 8, 9, 10, or 11 (or even more such as 12, 13, 14, 15, 16, 17, 18, 19 or 20) of the sequence positions corresponding to the sequence positions 44, 50, 79, 81, 98, 104, 125, 127, 128, 130 and/or 134 of the linear polypeptide sequence of the lipocalin NGAL (SEQ ID NO: 20), more preferably of the linear polypeptide sequence of SEQ ID NO: 1. Such a nucleic acid may subjected to mutagenesis and introduced into a suitable bacterial or eukaryotic host organism by using recombinant DNA technology. Obtaining a nucleic acid library of a lipocalin can be carried out using any suitable technique that is known in the art for generating lipocalin muteins with antibody-like properties, i.e. muteins that have affinity towards a given target. Examples of such combinatorial methods are described in detail in the international patent applications WO 99/16873, WO 00/75308, WO 03/029471, WO 03/029462, WO 03/029463, WO 2005/019254, WO 2005/019255, WO 2005/019256, or WO 2006/56464 for instance. The content of each of these patent applications is incorporated by reference herein in their entirety. After expression of the nucleic acid sequences that were subjected to mutagenesis in an appropriate host, the clones carrying the genetic information for the plurality of respective lipocalin muteins, which bind a given target can be selected from the library obtained. Well known techniques can be employed for the selection of these clones, such as phage display (reviewed in Kay, B. K. et al. (1996) supra; Lowman, H. B. (1997) supra or Rodi, D. J., and Makowski, L. (1999) supra), colony screening (reviewed in Pini, A. et al. (2002) *Comb. Chem. High Throughput Screen.* 5, 503-510), ribosome display (reviewed in Amstutz, P. et al. (2001) *Curr. Opin. Biotechnol.* 12, 400-405) or mRNA display as reported in Wilson, D. S. et al. (2001) *Proc. Natl. Acad. Sci. USA* 98, 3750-3755 or the methods specifically described in WO 99/16873, WO 00/75308, WO 03/029471, WO 03/029462, WO 03/029463, WO 2005/019254, WO 2005/019255, WO 2005/019256, or WO 2006/56464.

In accordance with this disclosure, another embodiment of the above methods comprises:

(i) providing at least a fragment of CTLA-4 as a given target/ligand for example, contacting the plurality of muteins with said target/ligand in order to allow formation of complexes between said ligand and muteins having binding affinity for said target/ligand, and (ii) removing muteins having no or no substantial binding affinity.

In one embodiment of the methods of the invention, the selection binding affinity is carried out under competitive conditions. Competitive conditions as used herein means that selection of muteins encompasses at least one step in which the muteins and the fragment of CTLA-4 are brought in contact in the presence of an additional ligand, which competes with binding of the muteins to the target (CTLA-4). Alternatively, the additional ligand competes with binding of the muteins by complexing an epitope distinct from the binding site of the muteins to the target by allosteric effects. Accordingly, any fragment (including soluble fragment), precursor or mature form of CTLA-4 can be used in the generation of muteins of the invention.

A further embodiment of the methods of the invention involves operably fusing a nucleic acid coding for the plurality of muteins of the invention and resulting from mutagenesis at the 3' end with a gene coding for the coat protein pIII of a filamentous bacteriophage of the M13-family or for a fragment of this coat protein, in order to select at least one mutein for the binding of a given ligand.

The fusion protein may include additional components such as an affinity tag, which allows the immobilization, detection and/or purification of the fusion protein or its parts. Furthermore, a stop codon can be located between the sequence regions encoding the lipocalin or its muteins and the phage capsid gene or fragments thereof, wherein the stop codon, preferably an amber stop codon, is at least partially translated into an amino acid during translation in a suitable suppressor strain.

For example, the phasemid vector pTLPC27, now also called pTlc27 that is described here can be used for the preparation of a phagemid library encoding muteins of the invention. The inventive nucleic acid molecules coding for muteins of the invention can be inserted into the vector using the two BstXI restriction sites. After ligation a suitable host strain such as *E. coli* XL1-Blue is transformed with the resulting nucleic acid mixture to yield a large number of independent clones. A respective vector can be generated for the preparation of a hyperphagemid library, if desired.

Once a mutein with affinity to a given target has been selected, it is additionally possible to subject such a mutein to another mutagenesis in order to subsequently select variants of even higher affinity or variants with improved properties such as higher thermostability, improved serum stability, thermodynamic stability, improved solubility, improved monomeric behavior, improved resistance against thermal denaturation, chemical denaturation, proteolysis, or detergents etc. This further mutagenesis, which in case of aiming at higher affinity can be considered as in vitro "affinity maturation," can be achieved by site specific mutation based on rational design or a random mutation. Another possible approach for obtaining a higher affinity or improved properties is the use of error-prone PCR, which results in point mutations over a selected range of sequence positions of the lipocalin mutein. The error-prone PCR can be carried out in accordance with any known protocol such as the one described by Zaccolo et al. (1996) *J. Mol. Biol.* 255, 589-603. Other methods of random mutagenesis that are suitable for such purposes include random insertion/deletion (RID) mutagenesis as described by Murakami et al. (2002) *Nat. Biotechnol.* 20, 76-81 or nonhomologous random recombination (NRR) as described by Bittker et al. (2002) *Nat. Biotechnol.* 20, 1024-1029. If desired, affinity maturation can also be carried out according to the procedure described in WO 00/75308 or Schlehuber et al. (2000) *J. Mol. Biol.* 297, 1105-1120, where muteins of the bilin-binding protein having high affinity to digoxigenin were obtained. A further approach for improving the affinity is to carry out positional saturation mutagenesis. In this approach "small" nucleic acid libraries can be created in which amino acid exchanges/mutations are only introduced at single positions within any of the four loop segments. These libraries are then directly subjected to a selection step (affinity screening) without further rounds of panning. This approach allows the identification of residues that contribute to improved binding of the desired target and allows identification of "hot spots" that are important for the binding.

In one embodiment, the above method for modifying a mutein further includes introducing a Cys residue at least one of any of the sequence positions that correspond to sequence positions 14, 21, 60, 84, 88, 116, 141, 145, 143, 146 or 158 of the wild type sequence of human Lipocalin 2 and coupling a moiety that is able to modify the serum half time of said mutein via the thiol group of a Cys residue introduced at least one of any of the sequence positions that correspond to sequence positions 14, 21, 60, 84, 88, 116, 141, 145, 143, 146 or 158 of the wild type sequence of hNGAL. The moiety that is able to modify the serum half time of said mutein may be selected from the group consisting of a polyalkylene glycol molecule and hydroxyethylstarch.

Where a protein of the invention is a human Lipocalin 2 mutein of the invention, the naturally occurring disulfide bond between Cys 76 and Cys 175 may be removed. Accordingly, such muteins (or any other human Lipocalin 2 mutein that does not include an intramolecular disulfide bond) can be produced in a cell compartment having a reducing redox milieu, for example, in the cytoplasma of Gram-negative bacteria.

In case a lipocalin mutein of the invention includes intramolecular disulfide bonds, it may be preferred to direct the nascent polypeptide to a cell compartment having an oxidizing redox milieu using an appropriate signal sequence. Such an oxidizing environment may be provided by the periplasm of Gram-negative bacteria such as *E. coli*, in the extracellular milieu of Gram-positive bacteria or in the lumen of the endoplasmatic reticulum of eukaryotic cells and usually favors the formation of structural disulfide bonds.

It is, however, also possible to produce a mutein of the invention in the cytosol of a host cell, preferably *E. coli*. In this case, the polypeptide can either be directly obtained in a soluble and folded state or recovered in form of inclusion bodies, followed by renaturation in vitro. A further option is the use of specific host strains having an oxidizing intracellular milieu, which may thus allow the formation of disulfide bonds in the cytosol (Venturi et al. (2002) *J. Mol. Biol.* 315, 1-8).

However, a mutein of the invention may not necessarily be generated or produced only by use of genetic engineering. Rather, a lipocalin mutein can also be obtained by chemical synthesis such as Merrifield solid phase polypeptide synthesis or by in vitro transcription and translation. It is for example possible that promising mutations are identified using molecular modeling and then to synthesize the wanted (designed) polypeptide in vitro and investigate the binding activity for a given target. Methods for the solid phase and/or solution phase synthesis of proteins are well known in the art (reviewed, e.g., in Lloyd-Williams et al. (1997) *Chemical Approaches to the Synthesis of Peptides and Proteins*. CRC Press, Boca Raton, Fields, GB, and Colowick (1997) *Solid-Phase Peptide Synthesis*. Academic Press, San Diego, or Bruckdorfer et al. (2004) *Curr. Pharm. Biotechnol.* 5, 29-43).

In another embodiment, the muteins of the invention may be produced by in vitro transcription/translation employing well-established methods known to those skilled in the art.

The invention also relates to a pharmaceutical composition that includes at least one inventive mutein referred to in the claims or a fusion protein or conjugates thereof and, optionally, a pharmaceutically acceptable excipient.

The lipocalin muteins according to the invention can be administered via any parenteral or non-parenteral (e.g. enteral) route that is therapeutically effective for proteinaceous drugs. Parenteral application methods include, for example, intracutaneous, subcutaneous, intramuscular or intravenous injection and infusion techniques, e.g. in the form of injection solutions, infusion solutions or tinctures, as well as aerosol installation and inhalation, e.g. in the form of aerosol mixtures, sprays or powders. Non-parenteral delivery modes are, for instance, orally, e.g. in the form of pills, tablets, capsules, solutions or suspensions, or rectally, e.g. in the form of suppositories. The muteins of the invention can be administered systemically or topically in formulations containing conventional non-toxic pharmaceutically acceptable excipients or carriers, additives and vehicles as desired.

In one embodiment of the present invention the pharmaceutical is administered parenterally to a vertebrate animal, including a mammal, and in particular to a human. Corresponding administration methods include, but are not limited to, for example, intracutaneous, subcutaneous, intramuscular or intravenous injection and infusion techniques, e.g. in the form of injection solutions, infusion solutions or tinctures as well as aerosol installation and inhalation, e.g. in the form of aerosol mixtures, sprays or powders. A combination of intravenous and subcutaneous infusion and/or injection might be most convenient in case of compounds with a relatively short serum half life. The pharmaceutical composition may be an aqueous solution, an oil-in water emulsion or a water-in-oil emulsion.

In this regard it is noted that transdermal delivery technologies, e.g. iontophoresis, sonophoresis or microneedle-enhanced delivery, as described in Meidan and Michniak (2004) *Am. J. Ther.* 11(4), 312-316, can also be used for transdermal delivery of the muteins described herein. Non-parenteral delivery modes are, for instance, oral, e.g. in the form of pills, tablets, capsules, solutions or suspensions, or rectal administration, e.g. in the form of suppositories. The muteins of the invention can be administered systemically or topically in formulations containing a variety of conventional non-toxic pharmaceutically acceptable excipients or carriers, additives, and vehicles.

The dosage of the mutein applied may vary within wide limits to achieve the desired preventive effect or therapeutic response. It will, for instance, depend on the affinity of the compound for a chosen ligand as well as on the half-life of the complex between the mutein and the ligand in vivo. Further, the optimal dosage will depend on the biodistribution of the mutein or its fusion protein or its conjugate, the mode of administration, the severity of the disease/disorder being treated as well as the medical condition of the patient. For example, when used in an ointment for topical applications, a high concentration of a protein of the invention can be used. However, if wanted, the protein may also be given in a sustained release formulation, for example liposomal dispersions or hydrogel-based polymer microspheres, like PolyActive™ or OctoDEX™ (cf. Bos et al., *Business Briefing: Pharmatech* 2003: 1-6).

Accordingly, the muteins of the present invention can be formulated into compositions using pharmaceutically acceptable ingredients as well as established methods of preparation (Gennaro and Gennaro (2000) *Remington: The Science and Practice of Pharmacy*, 20th Ed., Lippincott Williams & Wilkins, Philadelphia, Pa.). To prepare the pharmaceutical compositions, pharmaceutically inert inorganic or organic excipients can be used. To prepare e.g. pills, powders, gelatine capsules or suppositories, for example, lactose, talc, stearic acid and its salts, fats, waxes, solid or liquid polyols, natural and hardened oils can be used. Suitable excipients for the production of solutions, suspensions, emulsions, aerosol mixtures or powders for reconstitution into solutions or aerosol mixtures prior to use include water, alcohols, glycerol, polyols, and suitable mixtures thereof as well as vegetable oils.

The pharmaceutical composition may also contain additives, such as, for example, fillers, binders, wetting agents, glidants, stabilizers, preservatives, emulsifiers, and furthermore solvents or solubilizers or agents for achieving a depot effect. The latter is that fusion proteins may be incorporated into slow or sustained release or targeted delivery systems, such as liposomes and microcapsules.

The formulations can be sterilized by numerous means, including filtration through a bacteria-retaining filter, or by incorporating sterilizing agents in the form of sterile solid compositions which can be dissolved or dispersed in sterile water or other sterile medium just prior to use.

A mutein of the present invention or a fusion protein or a conjugate thereof can be employed in many applications. In general, such a mutein can be used in all applications antibodies are used, except those which specifically rely on the glycosylation of the Fc part.

A lipocalin mutein described herein can be administered to an organism, including a human patient per se, or in a pharmaceutical composition where it may include or be mixed with pharmaceutically active ingredients or suitable carriers or excipient(s). Techniques for formulation and administration of a respective lipocalin mutein composition resemble or are identical to those of low molecular weight compounds well established in the art. Exemplary routes include, but are not limited to, oral, transdermal, and parenteral delivery. A lipocalin mutein or a respective composition may be used to fill a capsule or tube, or may be provided in compressed form as a pellet. The lipocalin mutein or a respective composition may also be used in injectable or sprayable form, for instance as a suspension of a respective lipocalin mutein.

A composition that includes a lipocalin mutein of the invention may for instance be applied onto the skin or onto a wound. Further suitable routes of administration may, for example, include depot, oral, rectal, transmucosal, or intestinal administration; parenteral delivery, including intramuscular, subcutaneous, intravenous, intramedullary injections, as well as intrathecal, direct intraventricular, intraperitoneal, intranasal, or intraocular injections. In some embodiments one may administer a lipocalin mutein or a respective composition in a local rather than systemic manner, for example, via injection.

Pharmaceutical compositions that include a lipocalin mutein of the present invention may be manufactured in a manner that is itself known, e.g., by means of conventional mixing, dissolving, granulating, dragee-making, levigating, emulsifying, encapsulating, entrapping or lyophilizing processes. A pharmaceutical composition for use in accordance with the present invention thus may be formulated in conventional manner using one or more physiologically acceptable carriers including excipients and auxiliaries that facilitate processing of the hydrogel and/or peptide/peptoid into preparations that can be used pharmaceutically. Proper formulation is dependent upon the route of administration chosen.

For injection, the lipocalin mutein or a respective composition may be formulated in aqueous solutions, for instance in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the lipocalin mutein or a respective composition can be formulated readily by combining them with pharmaceutically acceptable carriers well known in the art. Such carriers enable the lipocalin mutein or a respective composition, as well as a pharmaceutically active compound where present, to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatine, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatine, as well as soft, sealed capsules made of gelatine and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the peptides/peptoids may be suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

A lipocalin mutein of the invention may be formulated for parenteral administration by injection, e.g., by intramuscular injections or bolus injection or continuous infusion. Formulations for injection may be presented in unit dosage form, e.g., in ampules or in multi-dose containers, with an added preservative. The respective compositions may take such forms as suspensions, solutions or emulsions in oily or aqueous vehicles, and may contain formulatory agents such as suspending, stabilizing and/or dispersing agents.

A lipocalin mutein of the invention of the invention may also be used to target a compound to a pre-selected site. In one such embodiment, a lipocalin mutein of the invention is used for the targeting of a pharmaceutically active compound to a pre-selected site in an organism or tissue, comprising:

a) conjugating the lipocalin mutein with said compound, and b) delivering the lipocalin mutein/compound complex to the pre-selected site.

For such a purpose the mutein is contacted with the compound of interest in order to allow complex formation. Then the complex comprising the mutein and the compound of interest are delivered to the pre-selected site. This may, for example, be achieved by coupling the mutein to a targeting moiety, such as an antibody, antibody fragment or lipocalin mutein or lipocalin mutein fragment with binding affinity for the selected target.

This use is in particular suitable, but not restricted to, for delivering a drug (selectively) to a pre-selected site in an organism, such as an infected body part, tissue or organ which is supposed to be treated with the drug. Besides formation of a complex between mutein and compound of interest, the mutein can also be reacted with the given compound to yield a conjugate of mutein and compound. Similar to the above complex, such a conjugate may be suitable to deliver the compound to the pre-selected target site. Such a conjugate of mutein and compound may also include a linker that covalently links mutein and compound to each other. Optionally, such a linker is stable in the bloodstream but is cleavable in a cellular environment.

The muteins disclosed herein and its derivatives can thus be used in many fields similar to antibodies or fragments thereof. In addition to their use for binding to a support, allowing the target of a given mutein or a conjugate or a fusion protein of this target to be immobilized or separated, the muteins can be used for labeling with an enzyme, an antibody, a radioactive substance or any other group having biochemical activity or defined binding characteristics. By doing so, their respective targets or conjugates or fusion proteins thereof can be detected or brought in contact with them. For example, muteins of the invention can serve to detect chemical structures by means of established analytical methods (e.g. ELISA or Western Blot) or by microscopy or immunosensorics. Here, the detection signal can either be generated directly by use of a suitable mutein conjugate or fusion protein or indirectly by immunochemical detection of the bound mutein via an antibody.

Numerous possible applications for the inventive muteins also exist in medicine. In addition to their use in diagnostics and drug delivery, a mutant polypeptide of the invention, which binds, for example, tissue- or tumor-specific cellular surface molecules can be generated. Such a mutein may, for example, be employed in conjugated form or as a fusion protein for "tumor imaging" or directly for cancer therapy.

In a further aspect, the present invention also encompasses the use of a mutein according to the invention for the manufacture of a pharmaceutical composition. The pharmaceutical composition may be used as monotherapy or as combination therapy. Accordingly, the invention also relates to a mutein as defined above for the treatment of a disease or disorder associated with an altered, e.g. increased or reduced, level of CTLA-4.

In yet another aspect the invention relates to the use of a mutein according to the invention in diagnosis. The use of a mutein according to the invention is typically for the diagnosis of a disease or disorder associated with an altered level of CTLA-4 as well as a respective method of diagnosis.

Accordingly, the invention also relates to a mutein as defined above for the diagnosis of a disease or disorder associated with an altered, e.g. increased or reduced, level of CTLA-4.

In principle, a CTLA-4 binding compound/mutein of the invention can be used in any therapeutic application in which binding of CTLA-4 to a physiological ligand, for example, B7-1 or B7-2 is involved. Examples of such therapeutic applications include, but are not limited to, the prevention and/or treatment of cancer or the prevention and/treatment of an infectious disease. In such application, an anti-CTLA-4 lipocalin mutein is administered to a mammal, for example, a human, a dog, an ape, a rat, a mouse, in an amount of that is effective in treating said cancer or that infectious disease.

The infectious diseases may be caused by exposure to a particular toxin or pathogen. Similar to its application to tumors as discussed below, CTLA-4 blockade that is mediated by a CTLA-4 binding lipocalin mutein, and surrogate therapeutic endpoint can be used alone, or as an adjuvant, in combination with vaccines, to stimulate the secondary or memory immune response to pathogens, toxins, and self-antigens. CTLA-4 blockade has been shown to be effective in the acute phase of infections of *Nippostrongylus brasiliensis* (McCoy, K. et al. (1997) 186 (2); 183-187) and *Leishmania donovani* (Murphy, M. et al. (1998) J. Immunol. 161: 4153-4160). Examples of pathogens for which this therapeutic approach may be particularly useful include pathogens for which there is currently no effective vaccine, or pathogens for which conventional vaccines are of limited effectiveness. These include, but are not limited to HIV, Hepatitis (A, B, & C), Influenza, Herpes, *Giardia, Malaria, Leishmania, Staphylococcus aureus,* and *Pseudomonas aeruginosa.* CTLA-4 blockade is particularly useful in boosting immunity against established infections by agents such as HIV that present altered antigens over the course of the infections. These epitopes are recognized as foreign at the time of administration of the CTLA-4 binding compound/mutein of the invention, thus provoking a strong T cell response that is not dampened by negative signals through CTLA-4. Some examples of pathogenic viruses causing infections treatable by using CTLA-4 binding lipocalin muteins of the invention include hepatitis (A, B, or C), herpes virus (e.g., VZV, HSV-1, HAV-6, HSV-11, and CMV, Epstein Barr virus), adenovirus, influenza virus, flaviviruses, echovirus, rhinovirus, coxsackie virus, cornovirus, respiratorysyncytial virus, mumps virus, rotavirus, measles virus, rubella virus, parvovirus, vaccina virus, HTLV virus, dengue virus, papillomavirus, molluscum virus, poliovirus, rabies virus, JC virus and arboviral encephalitis virus, to name only a few. Some examples of pathogenic bacteria causing infections treatable by CTLA-4 binding lipocalin muteins include chlamydia, rickettsial bacteria, mycobacteria, staphylococci, streptococci, pneumonococci, meningococci and conococci, *klebsiella, proteus, serratia, pseudomonas, legionella, diphtheria, salmonella,* bacilli, cholera, tetanus, botulism, anthrax, plague, leptospirosis, and Lyme disease bacteria. Some examples of pathogenic fungi causing infections treatable by CTLA-4 binding lipocalin muteins include *Candida (albicans, krusei, glabrata, tropicalis,* etc.) *Cryptococcus neoformans, Aspergillus (fumigatus, niger* etc.), Gefaus Mucorales (*Mucor, Absidia, Rhizophus), Sporothrix schenkii, Blastomyces dermatitidis, Paracoccidioides brasiliensis, Coccidioidesimmitis* and *Histoplasma capsulatum.* Some examples of pathogenic parasites causing infections treatable by CTLA-4 binding muteins include *Entamoeba histolytica, Balantidium coli, Naegleria fowleri, Acanthamoeba* sp., *Giardia lambia, Cryptosporidium* sp., *Pneumocystis carinii, Plasmodium* vivax, Babesia microti, Trypanosoma brucei, Trypanosoma cruzi, Leishmania donovani, Toxoplasma gondi, and Nippostrongylus brasiliensis.

Also, the invention relates to a method of treating a tumor or cancer, the method comprising administering a pharmaceutical composition as described herein containing a mutein of the invention to a subject in need thereof. Likewise, the invention relates to a mutein of the invention for use in treating a tumor or cancer. Similarly, the invention concerns the use of a mutein of the invention for the preparation of a pharmaceutical composition for treating a tumor or cancer. The cancer or tumor to be treated is not particularly limited, and specific examples may include lung cancer, bone cancer, pancreatic cancer, skin cancer, cancer of the head or neck, cutaneous or intraocular malignant melanoma, uterine cancer, ovarian cancer, rectal cancer, cancer of the anal region, stomach cancer, colon cancer, breast cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemias, solid tumors of childhood, lymphocytic lymphoma, cancer of the bladder, cancer of the kidney or ureter, renal cell carcinoma, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, t-cell lymphoma, cutaneous T cell lymphoma (CTCL), and combinations of said cancers.

When applied for the treatment of cancer, the CTLA-4 binding compound or mutein can be administered to a mammal in combination with another pharmaceutically active agent. Examples of such agents include, but are not limited to, a chemotherapeutic or anti-tumor agent, a cancer vaccine, an immunomodulatory agent, an anti-angiogenesis agent, an anti-vascular agent, a signal transduction inhibitor, an anti-proliferative agent, an apoptosis inducer, a chemokine, a cytokine and an inhibitor of a survival pathway. In one presently preferred embodiment, the mutein is administered in combination with an anti-angiogenesis agent. Examples of suitable anti-angiogenesis are a MMP-2 (matrix-metalloproteinase 2) inhibitor, an MMP-9 (matrix-metalloproteinase 9) inhibitor, and a COX-II (cyclooxygenase II) inhibitor, to name only a few.

In another presently preferred embodiment, the CTLA-4 binding mutein is administered in combination with a chemotherapeutic agent. The chemotherapeutic agent may be a mitotic inhibitor, alkylating agent, anti-metabolite, intercalating antibiotic, growth factor inhibitor, cell cycle inhibitor, enzyme, topoisomerase inhibitor, biological response modifier, anti-hormone, angiogenesis inhibitor, or an anti-androgen.

In yet another presently preferred embodiment, the CTLA-4 binding mutein is administered in combination with a signal transduction inhibitor. Examples of suitable signal transduction inhibitors include, but are not limited to, an EGFR (epidermal growth factor receptor) inhibitor, VEGF (vascular endothelial growth factor) inhibitor, and an erbB2 receptor inhibitor. In yet another presently preferred embodiment, the CTLA-4 binding mutein is administered in combination with a cytokine. Illustrative examples of suitable cytokines for use in the present invention include Interleukin-2 (IL-2), Interferon-gamma (IFN-g), granulocyte/macrophage colony-stimulating factor (GM-CSF), Interferon-12 (IL-12), Interferon-18 (IL-18), and SL cytokine precursor (FLT-3L).

It is also encompassed in the present invention to administer to a mammal an amount of a CTLA-4 binding lipocalin mutein in combination with radiation therapy. The amount of the mutein in combination with the radiation therapy is effective in inhibiting abnormal cell growth or treating the hyperproliferative disorder in the mammal.

In another therapeutic application, a CTLA-4 binding mutein is employed for the treatment or prevention of T cell mediated disease or tumor types expressing CTLA-4 in a mammal. For this purpose, a fusion or conjugate of an anti-CTLA-4 mutein as described herein with a toxin can be used. The amount of said fusion or conjugate is chosen such that it is effective in treating said T cell mediated disease or tumor.

Examples of T cell mediated diseases that can be treated in this manner include graft versus host disease, transplant rejection or auto-immune diseases such as multiple sklerosis, lupus erythematosus, myasthenia gravis, rheumatoid arthritis or diabetes mellitus. For the same purpose, polyvalent formulations of CTLA-4 binding muteins that cross-link cell surface CTLA-4 and act as a CTLA-4 agonist might be used instead of a conjugate or fusion of a anti-CTLA-4 lipocalin mutein with a toxin (see, e.g., Krummel and Allison, 1996, J. Exp. Med. 183, 2533-2540, cf. also International patent application WO 01/14424). A polyvalent formulation of CTLA-4 binding muteins that acts as an agonist can be prepared by covalently crosslinking two or more of the muteins using respective cross-linking reagents. Alternatively, CTLA-4 binding muteins can be cross-linked to each other by non-covalent interactions. For this purpose, they can for example, be conjugated to or fused to an oligomerization module such as a leucine zipper, a jun/fos oligomerization module or an immunoglobulin domain (like CH4 as shown). Non-covalent oligomerization and thus formation of a preparation of polyvalent CTLA-4 muteins then occurs via this oligomerization module. In accordance with this approach, a polyvalent CTLA-4 cross-linking lipocalin mutein will transduce a negative signal similar to the signal elicited by the natural ligand and inhibit, reduce or prevent activation, expansion or effector activities of the CTLA-4 expressing T cell. Accordingly, a pharmaceutical composition wherein the at least two CTLA-4 binding muteins are (cross)-linked to each other to form a multimer, for example, a dimer, trimer or higher oligomer is also encompassed in the present invention. As mentioned above, a dimeric fusion protein in which two CTLA-4 binding molecules (which can be formed either by two different CTLA-4 binding muteins or two molecules of the same CTLA-4 binding mutein) are fused to each other can be used in such a pharmaceutical composition.

In still another aspect, the present invention features a diagnostic or analytical kit comprising a mutein according to the present invention.

The subject in need of such a treatment may be a mammal, such as a human, a dog, a mouse, a rat, a pig, an ape such as cynomolgous monkeys to name only a few illustrative examples, with human being preferred.

In still another aspect, the present invention features a method for in vivo imaging in a subject, including administering to said subject a mutein of the invention or a pharmaceutical composition comprising a mutein of the invention. The subject may be defined as above.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein. All publications and patents cited in this disclosure are incorporated by reference in their entirety. To the extent the material incorporated by reference contradicts or is inconsistent with this specification, the specification will supersede any such material.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The invention is further illustrated by the following non-limiting Examples and the attached drawings. However, these Examples should not be construed so as to limit the invention. Rather, they are merely exemplary embodiments.

Unless otherwise indicated, established methods of recombinant gene technology were used, for example, as described in Sambrook et al. (2001), supra.

EXAMPLES

Example 1

Figure 1:
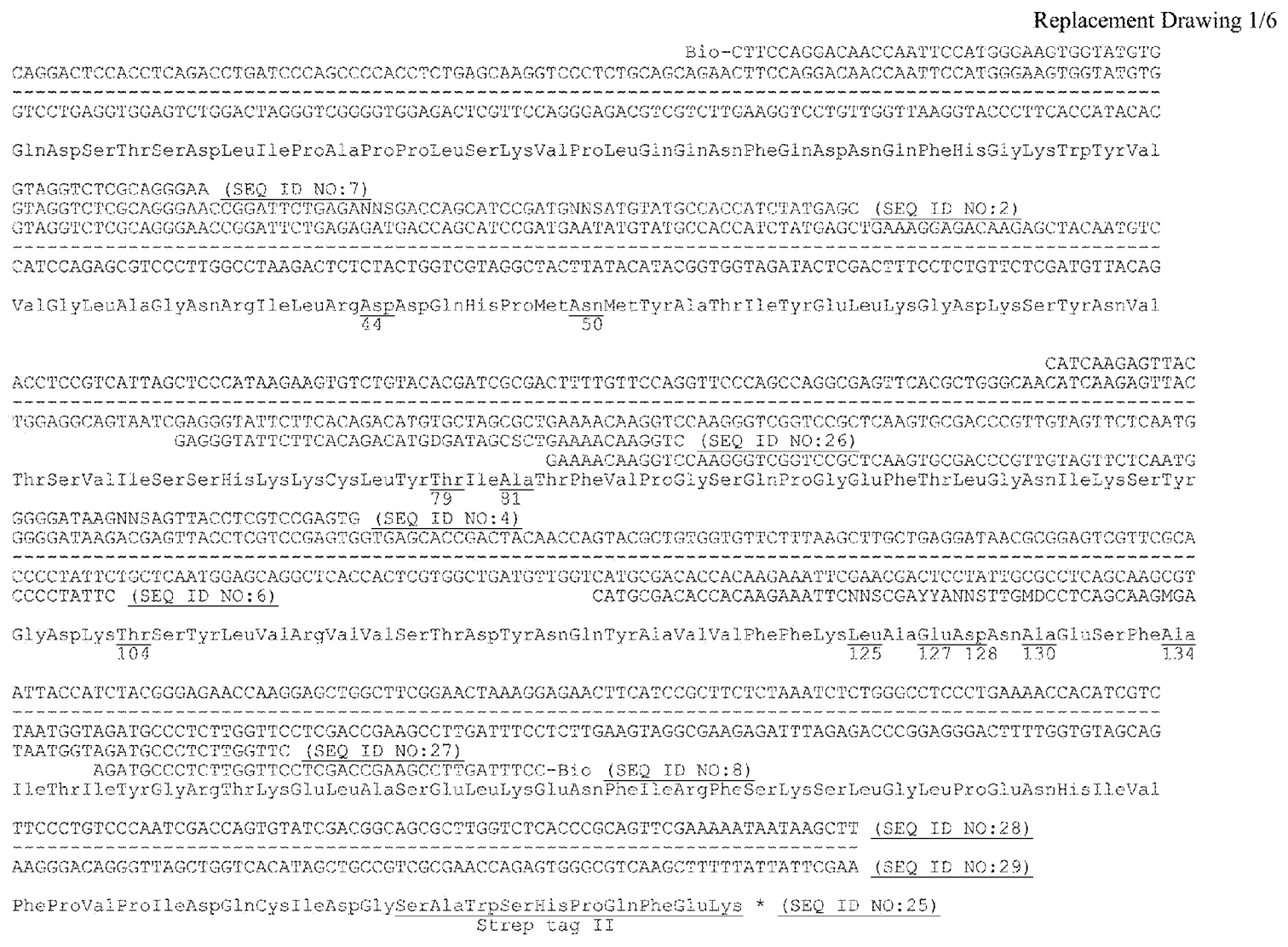

Construction of a Mutant Lcn2 Phage Display Library for the Affinity Maturation of CTLA-4-Specific hNGAL Muteins A mutant genetic library on the basis of a CTLA-4 specific Lcn2 mutein hNGALM1 with the SEQ ID NO: 1 was generated by site-directed randomization of 10 amino acid positions located mainly in the structurally variable loop regions in order to select an affinity matured mutein. Mutagenesis and polymerase chain reaction (PCR) assembly of this region was essentially performed according to a published strategy (Beste et al. (1999) *Proc. Natl. Acad. Sci. USA* 96, 1898-1903; Skerra (2001) *J. Biotechnol.* 74, 257-275), this time using a two pot amplification reaction with the template hNGALM1 and oligodeoxynucleotides (sequences of SEQ ID NO: 2 to SEQ ID NO: 8) as illustrated in FIG. 1. For the first PCR reaction Oligodeoxynucleotides were designed such that the primers with sequences of SEQ ID NO: 2 to SEQ ID NO: 5 carried degenerate codons at the amino acid positions 44, 50, or 79, 81, or 104, or 125, 127, 128, 130, 134, respectively, in order to introduce the combinatorial mutations. In a second PCR reaction a mediating primer with SEQ ID NO: 6 and the two flanking primers with SEQ ID NO: 7 and SEQ ID NO: 8 were used and served for the amplification of the assembled randomized library gene fragment. All PCR steps were performed using Go-Taq DNA polymerase (Promega, Mannheim, Germany) as described (Schlehuber et al. (2000) *J. Mol. Biol.* 297, 1105-1120).

Oligodeoxynucleotides that did not carry degenerate codons were purchased in HPLC grade from Metabion (Munich, Germany). Oligodeoxynucleotides bearing degenerated codons were purchased desalted from the same vendor and further purified by urea PAGE. The resulting DNA library was cut with BstXI (Promega, Mannheim, Germany) and cloned on the phagemid vector phNGAL35 (SEQ ID NO: 9), which is based on the generic expression vector pASK75 (Skerra (1994) *Gene* 151, 131-135) and codes for a fusion protein composed of the OmpA signal peptide, followed by a T7-affinity-tag (T7), the modified mature Lcn2, an amber codon, and the C-terminal fragment of the gene III coat protein of the filamentous bacteriophage M13, i.e. similar as previously described for the bilin-binding protein (Beste et al., supra; Skerra, supra). Electroporation of *E. coli* XL1-Blue (Bullock et al. (1987) *Biotechniques* 5, 376-378) with the ligation mixture of digested PCR product and digested plasmid DNA, yielded a library with a complexity corresponding to $7.7 \times 10^9$ independent transformants.

100 ml of the culture, containing the cells which were transformed with the phasemid vectors on the basis of phNGAL35 coding for the library of the lipocalin muteins as phage pill fusion proteins, were transferred to a sterile Erlenmeyer flask and incubated for one hour at 37° C., 160 rpm in 2YT medium without antibiotic selection pressure. Before infection with VCS-M13 helper phage the culture was diluted in 2YT medium to an OD550 of 0.1 with the corresponding antibiotic added and further grown under identical conditions until an OD550 of 0.6 was reached. After infection with VCS-M13 helper phage (Agilent Technologies, La Jolla, USA) at a multiplicity of infection of approximately 10 the culture was shaken for additional 30 min at 37° C., 100 rpm. Then the incubator temperature was lowered to 26° C. and the shaker speed was increased again to 160 rpm, after 10 min kanamycin (70 µg/ml) was added, followed by induction of gene expression via addition of anhydrotetracycline (ACROS Organics, Geel, Belgium) at 25 µg/l (125 µl of a 200 µg/ml stock solution in dimethylformamide, DMF per liter of culture). Incubation continued for another 12-15 h at 26° C., 160 rpm.

Cells from the complete culture were sedimented by centrifugation (30 min, 18000 g, 4° C.). The supernatant containing the phagemid particles was sterile-filtered (0.45 µm), mixed with ¼ volume 20% w/v PEG 8000, 15% w/v NaCl, and incubated on ice for at least 2 h. After centrifugation (30 min, 18000 g, 4° C.) the precipitated phagemid particles from 1 liter of culture were dissolved in 30 ml of cold BBS/E (200 mM Na-borate, 160 mM NaCl, 1 mM EDTA pH 8.0) containing 50 mM benzamidine (Sigma) and Pefabloc 1 µg/ml (Roth, Karlsruhe, Germany). The solution was incubated on ice for 1 h. After centrifugation of undissolved components (10 min, 43000 g, 4° C.) each supernatant was transferred to a new reaction vessel.

Addition of ¼ volume 20% w/v PEG 8000, 15% w/v NaCl and incubation for 60 min on ice served to reprecipitate the phagemid particles until the phagemids were aliquoted and frozen at −80° C. for storage. For the first selection cycle phagemids were thawed and centrifuged (30 min, 34000 g, 4° C.), the supernatant was removed, and the precipitated phagemid particles were dissolved and combined in a total of 400 μl PBS containing 50 mM benzamidine. After incubation for 30 min on ice the solution was centrifuged (5 min, 18500 g, 4° C.) in order to remove residual aggregates and the supernatant was used directly for the phage display selection.

Example 2

Phagemid Presentation and Selection of NGAL Muteins with Affinity for Extracellular Domain of Dimeric Human CTLA-4

Phagemids obtained from Example 1 were subjected to phage display selection against the recombinant biotinylated extracellular domain of dimeric human CTLA-4 (Schonfeld et al. (2009), *PNAS* 106, 8198-8203).

Phagemid display and selection of CTLA4-specific lipocalin muteins employing magnetic streptavidin beads was essentially carried out as described in Example 27 in International Patent application WO 2005/019256 except the following deviations: Phagemids and target were incubated in solution and the selection stringency was increased either by limiting the target concentration (1.2, 0.2 and 0.04 nM) and incubation time (5, 20 min) for phagemids with the target in order to select faster $k_{on}$ rates or by competition with 12, or 25 nM of an antagonistic CTLA-4 antibody BNI3 (BD Bioscience) at a target concentration of 1 nM. The phagemids were eluted both under acidic and basic conditions.

Phagemid amplification between each panning cycle was performed as described in Schlehuber, S. et al. (*J. Mol. Biol.* (2000), 297, 1105-1120).

Three rounds of selection against biotinylated CTLA4 were carried out in this way employing the preparation of amplified phagemids from the respective previous enrichment cycle with the exception that only about $3 \cdot 10^{11}$ phagemids were utilized beginning with the second enrichment cycle.

Example 3

Identification of CTLA4-Specific Muteins Using High-Throughput ELISA Screening

Screening of the muteins selected according to Example 2 was performed essentially as described in Example 3 of international patent application WO 2006/56464.

Therein, NGAL variants equipped with a T7 detection tag (Novagen) as well as a Strep-tag II affinity tag (IBA) were soluble expressed in a 96 well microtiter plate using the *E. coli* strain TG1/F with phNGAL37 SEQ ID NO: 10. This vector corresponds to phNGAL15 SEQ ID NO: 11 as described in the following example 4 with an N-terminal T7 tag consisting of 11 amino acids (MASMTGGQQMG (SEQ ID NO: 24)). Lipocalin mutein expression was induced overnight at 22° C. at 700 rpm with anhydrotetracycline (0.2 μg/ml) at an $OD_{550}$ of 0.6. Afterwards, cells were lysed (100 mM Na-borate, pH 8.0, 80 mM NaCl, 1 mM EDTA, 0.025% w/v lysozyme) for 1 h under agitation. To minimize non-specific binding in the subsequent ELISA screen, the crude cell lysates were supplemented with 2% w/v BSA and 0.1% v/v Tween 20 and tested in ELISA for binding to human CTLA-4-Fc (Chimerigen).

In a reverse ELISA approach soluble expressed muteins from the crude cell lysate were captured via immobilized T7 mAb (5 μg/ml, Novagen) on wells of black Fluotrac 600 ELISA plates (Greiner; 384 well). Neutravidin, 5 μg/ml, and 3% milk were used as negative control. Plates were blocked with PBST/0.1 containing 2% w/v BSA, and subsequently incubated with limited amounts of soluble human CTLA4-Fc (2 nM, 0.5 nM) for 1 h at room temperature in order to differentiate the muteins by their affinity. Subsequently plates were washed five times and bound target was detected via an goat anti-human Fc monoclonal antibody-HRP conjugate (Jackson ImmunoResearch), diluted 1:5.000 in PBST/0.1. Therefore, QuantaBlu™ (Pierce; 1:2 diluted in PBS/T 0.1%) was used as fluorogenic HRP substrate. After 45 min of signal development at room temperature fluorescence was excited at a wavelength of 320 nm (±12.5 nm) and measured at 430 nm (±17.5 nm) in a GENiosPlus plate reader (Tecan).

Screening of 2880 clones, selected as described in Example 2, led to the identification of more then 660 primary hits indicating the successful isolation of muteins having improved affinity for CTLA-4 compared to hNGALM1 SEQ ID NO: 1 which served as the basis for affinity maturation.

Further differentiation of the primary hits in terms of their target affinity was carried out in the identical reverse ELISA approach as described above but either under target-limiting conditions with CTLA4-Fc (Chimerigen) at concentrations of 1, and 0.1 nM, respectively, or under time-limiting conditions with 10 nM of target and a reduced incubation time of 5 min in order to select for muteins with faster kon rate.

In some cases a competition ELISA was carried out where CTLA4-Fc (2.5 μg/ml) was captured in ELISA plates via an immobilized mouse anti-human IgG Fc Gamma fragment-specific antibody (Jackson ImmunoResearch (5 μg/ml) and incubated for 1 h with a pre-mixture of the mutein extracts and different concentrations of a competitive CTLA4-specific mAb BNI3 (BD Bioscience) at concentrations of 30, 100, and 200 nM, respectively.

Figure 2B:
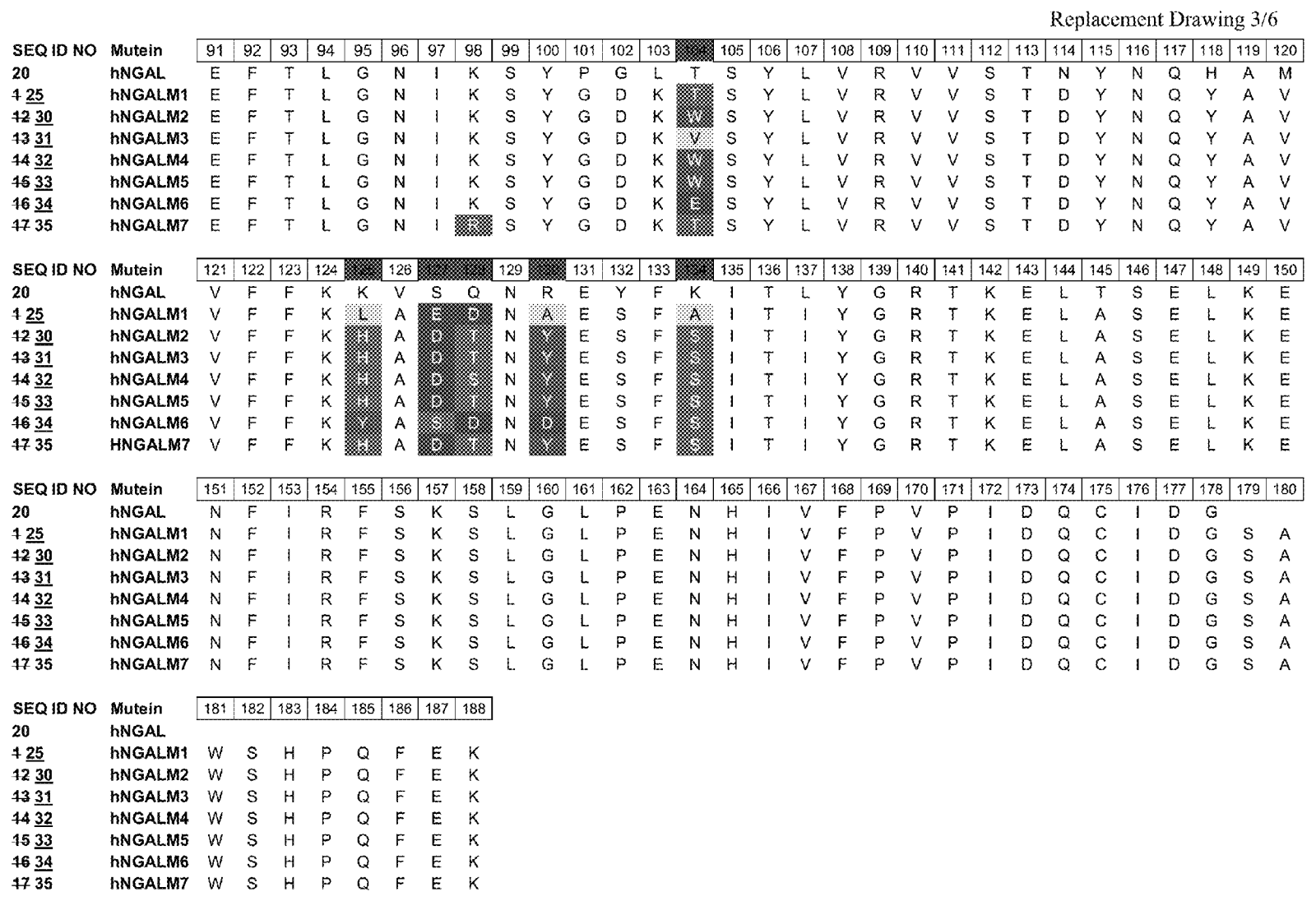

Using these ELISA approaches the muteins with SEQ ID NO: 12, SEQ ID NO: 13, SEQ ID NO: 14, SEQ ID NO: 15, SEQ ID NO: 16, and SEQ ID NO: 17, were identified. The sequences of these muteins are depicted in FIG. 2.

Example 4

Production of CTLA4-Binding Muteins (NGAL)

The recombinant Lcn2 and the human CTLA-4-specific Lcn2 variants were produced by periplasmic secretion in *E. coli* K12 strain JM83 (Yanisch-Perron et al. (1985) *Gene* 33, 103-119), the *E. coli* supE strain TG1-F— (a derivative of *E. coli* K12 TG1 [Kim et al. (2009) J. Am. Chem. Soc. 131, 3565-3576] that was cured from its episome using acridinium orange), or *E. coli* W3110 (Bachmann (1990) Microbiol. Rev. 54, 130-197).

For a small scale soluble protein expression the plasmid phNGAL15 (SEQ ID NO: 11) was used, encoding a fusion of the OmpA signal peptide with the respective mutein and the C-terminal Strep-tag II, whereby the plasmid carries the two non-compatible BstXI restriction sites for unidirectional subcloning of the mutated gene cassette. Growth was allowed to occur in a 2 L shaking flask culture in the presence of LB-Ampicillin medium according to the protocol described in Schlehuber, S. et al. (*J. Mol. Biol.* (2000), 297, 1105-1120).

For larger amounts of protein the periplasmatic production was performed with the same vector expressed in the E. coli strain W3110 via bench top fermenter cultivation in a 1 l or 10 l vessel based on the protocol described in Schiweck, W., and Skerra, A. *Proteins* (1995) 23, 561-565).

The Lcn2 variants were purified from the periplasmic fraction in a single step via streptavidin affinity chromatography (Strep-Tactin™ Superflow, IBA) using a column of appropriate bed volume according to the procedure described by Skerra, A. & Schmidt, T. G. M. (2000) (Use of the Strep-tag and streptavidin for detection and purification of recombinant proteins. *Methods Enzymol.* 326A, 271-304). To achieve higher purity and to remove any aggregated recombinant protein, a gel filtration of the muteins was finally carried out on a Superdex 75 HR 10/30 column (24-ml bed volume, Amersham Pharmacia Biotech, Freiburg, Germany) in the presence of PBS buffer. The monomeric protein fractions were pooled, analysed for purity by SDS-PAGE (Fling and Gregerson (1986) *Anal. Biochem.* 155, 83-88), and used for further biochemical characterization.

Example 5

Measurement of Binding Affinity for CTLA-4 Via Surface Plasmon Resonance on a Biacore T100 Instrument Real time affinity analysis was performed at 25° C. using a Biacore T100 system (GE Healthcare). Anti-human IgG-Fc antibody (Jackson ImmounoResearch Laboratories) was immobilized on a CM5 sensor chip using standard amine coupling chemistry, resulting in a ligand density of 8000 resonance units (RU). The reference channel was left blank (activated with EDC/NHS and subsequently blocked with ethanolamine). hCTLA4-Fc (Chimerigen) or murine CTLA4-Fc (R&D Systems) fusion protein was captured on this surface to a ligand density of approximately 300 RU at a flow rate of 10 μl/min in HBS-EP (Biacore). Subsequently, the Lcn2 muteins (SEQ ID: No 12 to SEQ ID NO: 17) were applied in an appropriate dilution series in HBS-EP at a flow rate of 30 μl/min. Regeneration of the derivatized chip surface was achieved by a combination of first basic (2.5 mM NaOH) and then acidic (10 mM glycine, pH 1.5) buffer, each for 8 and 16 s, respectively. Statistic analysis revealed that on average less than 1 RU protein remained bound after the regeneration step. To correct for buffer effects and baseline drift, double referencing was used throughout. Kinetic data evaluation was performed using the Biacore T100 Evaluation Software (v. 2.0.1) using the Langmuir 1:1 binding model and global fitting.

The values determined for ka and kd for the muteins of the sequences of SEQ ID NO: 12 to SEQ ID NO: 17 are summarized in Table I.

Example 6

Determination of Thermal Denaturation for CTLA4-Specific Lcn2 Muteins by Use of CD Spectroscopy Circular dichroism spectra of the purified CTLA4-specific Lcn2 muteins from affinity maturation as described in Example 2 were measured with a Jasco-810 spectropolarimeter (Jasco, Grofl-Umstadt, Germany) thermostatted with a computer controlled waterbath. Solutions of the lipocalin muteins were concentrated at 100-200 μg/ml in PBS buffer, pH 7.5 and applied in a quartz cuvette with a pathlength of 1 mm that was sealed with a Teflon lid. Thermal unfolding was performed by heating the sample at a constant temperature gradient of 40 k h-1 from 25 to 95° C. Data were collected for each 0.1 K step at a wavelength of 218 nm, where maximal spectral change upon unfolding was observed for Lcn2 muteins beforehand. The sample buffer showed no change in ellipticity with variation in temperature, so no corrections were made. Data from the thermal denaturation experiments were fitted by non-linear least-square regression using Kaleidagraph software and an equation for a two-state model of the unfolding transition as described at Brumano et al. (2000) Arch Biochem Biophys. 382(1), 57-62 and Cohen et al. (1994) Protein Sci. 3(8), 1253-60. Using the parameters from the corresponding curve fit, the unfolded fraction f(u) was plotted as a function of temperature T for illustration (see FIG. 3) and the values for the melting temperature is given in table 2.

TABLE 2

Tm of affinity-matured CTLA4-specific Lcn2 muteins

| Mutein | Tm [° C.] |
|---|---|
| hNGALM2 | 51 |
| hNGALM3 | 57 |
| hNGALM4 | 64 |
| hNGALM5 | 61 |
| hNGALM6 | 66 |
| hNGALM7 | 53 |

Example 7

B7.1 Blocking FACS on Human CTLA4-Transfected CHO Cells

Different concentrations of the Lcn2 muteins or, as a positive control, of the antibody BNI3 (BD Bioscience) were mixed with recombinant biotinylated human B7.1 (Ancell) at 10 nM final concentration and added to 100 000 of the CTLA-4 transfected CHO-K1 cells which were generated

TABLE 1

SPR analysis demonstrates cross-reactivity with KD values in the picomolar range for human CTLA4-Fc and mouse CTLA4 as well.

Figure 4:
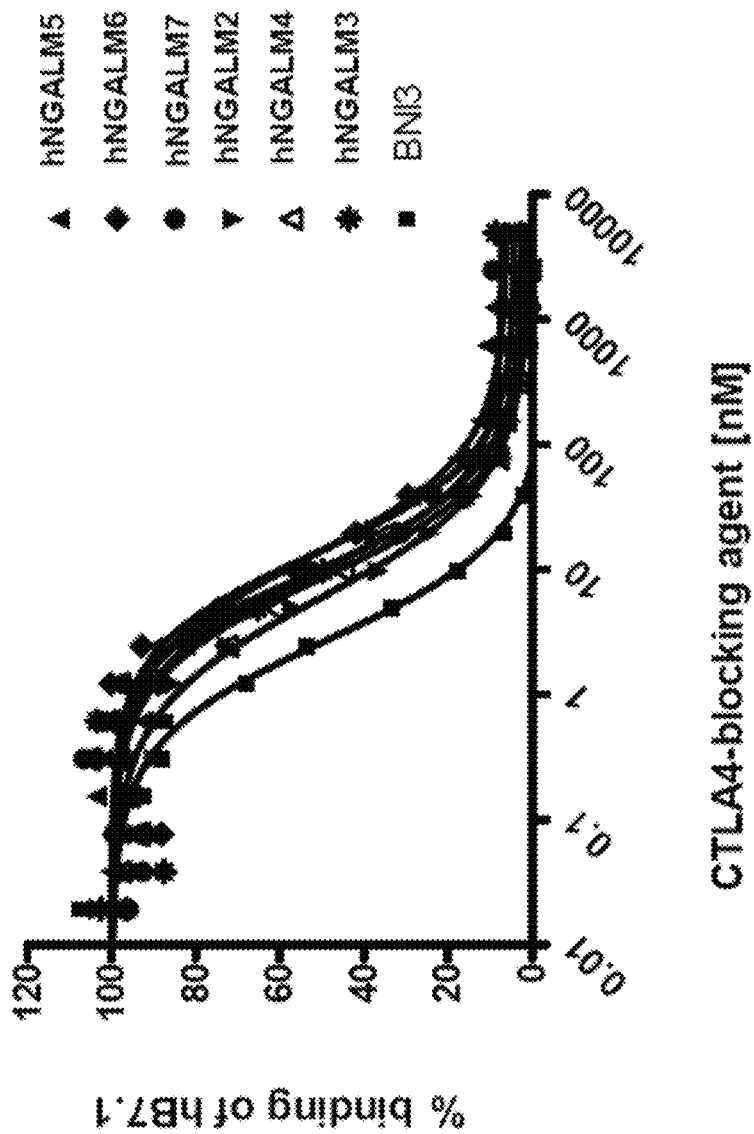

| | human CTLA4 | | | mouse CTLA4 | | |
|---|---|---|---|---|---|---|
| hNGALM2 | 5.65E+05 | 3.88E−04 | 6.86E−10 | 2.98E+05 | 9.07E−04 | 3.05E−09 |
| hNGALM3 | 4.22E+05 | 1.94E−04 | 4.60E−10 | 1.99E+05 | 1.34E−04 | 6.72E−10 |
| hNGALM4 | 5.39E+05 | 1.86E−04 | 3.46E−10 | 2.21E+05 | 1.29E−04 | 5.84E−10 |
| hNGALM5 | 3.80E+05 | 2.81E−04 | 7.40E−10 | 8.13+05 | 2.61E−04 | 3.20E−10 |
| hNGALM7 | 7.84E+05 | 5.17E−04 | 6.59E−10 | 2.61E+05 | 1.08E−04 | 4.13E−10 |
| hNGALM6 | 3.35E+05 | 1.97E−04 | 5.88E−10 | 6.36E+07 | 4.207 | 6.61E−08 | according to the description in example 16 of PCT/EP 2005/ 012640. Samples were incubated at 4° C. for 2 h, washed twice in PBS containing 2% w/v BSA, and detection of bound B7.1 was accomplished by incubation with streptavidin-phycoerythrin for 30 min at 4° C. Mean fluorescence intensities were determined by flow cytometry and fitted to a sigmoidal dose response model using Prism (GraphPad) as depicted in FIG. 4 to determine EC50 values for Lcn2 muteins from sequences of SEQ ID NO: 12 to SEQ ID NO: 17 which are summarized in Table 3. Wild type Lcn2 or isotype control antibody did not lead to measurable inhibition of B7.1 binding to the CTLA-4 expressing CHO cells (data not shown).

TABLE 3

EC50 values of affinity-matured CTLA4-specific Lcn2 muteins in a B7.1 blocking FACS on human CTLA4-transfected CHO cells.

| Mutein | EC50 [nM] |
|---|---|
| hNGALM2 | 6 |
| hNGALM3 | 7.6 |
| hNGALM4 | 9.5 |
| hNGALM5 | 9 |
| hNGALM6 | 10.3 |
| hNGALM7 | 11 |

Example 8

A CTLA4-Specific Mutein Specifically Inhibits Tumour Growth in the Murine Syngenic CSA1 M Tumor Model (p<0.001)

Figure 5:
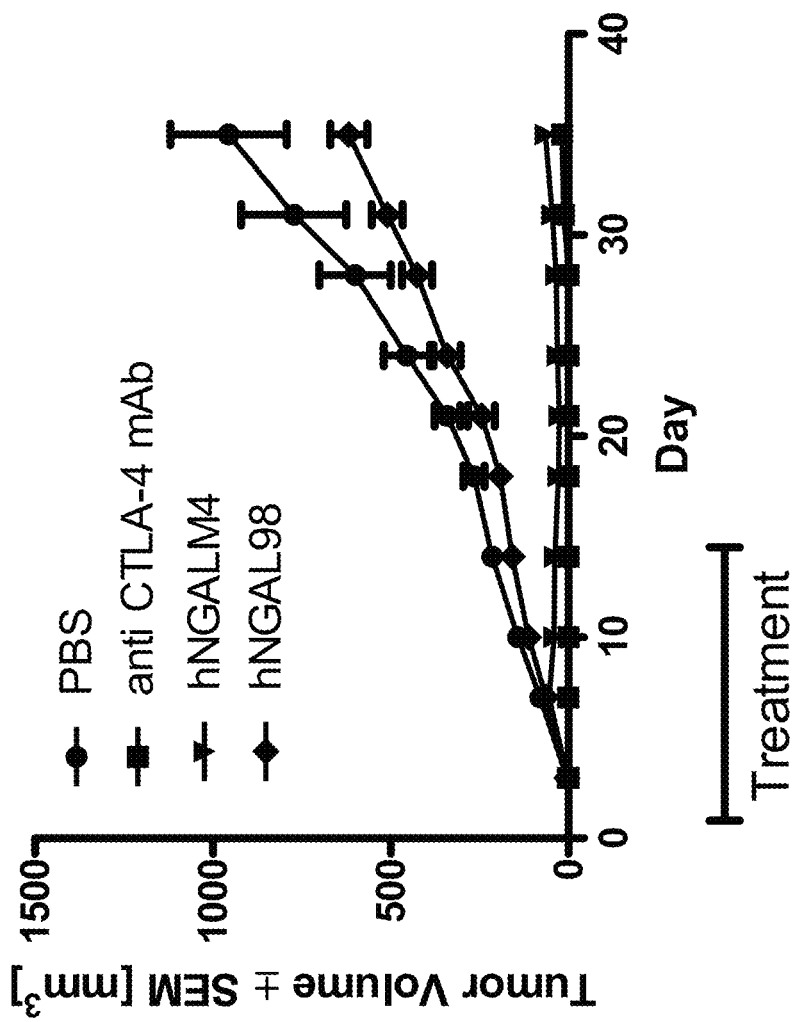

As depicted in FIG. 5, to assess in comparision the specific in vivo activity of a CTLA4-specific mutein hNGALM4 (SEQ ID NO: 14) in the murine syngenic CSA1M tumor model, CSA1M cells was used in a dose that leads to a progressively growing, subcutaneous tumor in 100% of S.C. injected syngeneic Balb/c mice. Treatment of tumor-bearing animals with the positive control antibody and negative isotype control antibody were started on the same day as the tumor challenge. The endpoint for pharmacologic activity was reduction of S.C. tumor growth. CSA1M cells were trypsinized, counted, washed and resuspended in serum-free DMEM medium for subcutaneous (S.C.) injection ($1.0 \times 10^6$ cells per mouse) onto the flank of Balb/c mice. Anticipated growth patterns were observed with positive and negative control groups. hNGALM4 strongly inhibited tumor growth over a 35 day period with tumor growth (p<0.001). No toxicity was observed in mice treated with hNGALM4.

The invention claimed is:

1. A lipocalin mutein capable of binding human Cytotoxic T-Lymphocyte Antigen 4 (CTLA-4) with an affinity by a KD of about 1 nM or lower, wherein the mutein comprises at least 8 mutated amino acid residues at the amino acid sequence positions 44, 50, 79, 81, 98, 104, 125, 127, 128, 130 and/or 134 of the linear polypeptide sequence of human Lipocalin 2 (hNGAL) (SEQ ID NO: 1).

2. The mutein of claim 1, wherein the mutein comprises, with respect to the linear polypeptide sequence of hNGAL, one or more amino acid substitutions selected from the group consisting of: Glu 44→Asp, Gln, Ser, or Leu, Lys 50→Asn, Asp, Leu, Pro, or Arg, Trp 79→Thr, Pro, or Ser, Arg 81→Ala, Lys 98→Arg, Thr 104→Trp, Val, Glu, or Thr, Lys 125→Leu, His, or Tyr, Ser 127→Glu, or Asp, Gln 128→Asp, Thr, or Ser, Arg 130→Ala, Tyr, or Asp, Lys 134→Ala, or Ser.

3. The mutein of claim 1, wherein the amino acid sequence of the mutein comprises, with respect to the linear polypeptide sequence of hNGAL, one of the following sets of amino acid substitutions:

(a) Glu 44→Asp; Lys 50→Asn; Trp 79→Thr; Arg 81→Ala; Lys 125→Leu; Ser 127→Glu; Gln 128→Asp; Arg 130→Ala; Lys 134→Ala;

(b) Glu 44→Asp; Lys 50→Asp; Trp 79→Pro; Arg 81→Ala; Thr 104→Trp; Lys 125→His; Ser 127→Asp; Gln 128→Thr; Arg 130→Tyr; Lys 134→Ser;

(c) Glu 44→Gln; Lys 50→Leu; Trp 79→Pro; Arg 81→Ala; Thr 104→Val; Lys 125→His; Ser 127→Asp; Gln 128→Thr; Arg 130→Tyr; Lys 134→Ser;

(d) Glu 44→Asp; Lys 50→Pro; Trp 79→Pro; Arg 81→Ala; Thr 104→Trp; Lys 125→His; Ser 127→Asp; Gln 128→Ser; Arg 130→Tyr; Lys 134→Ser;

(e) Glu 44→Ser; Lys 50→Arg; Trp 79→Thr; Arg 81→Ala; Thr 104→Trp; Lys 125→His; Ser 127→Asp; Gln 128→Thr; Arg 130→Tyr; Lys 134→Ser;

(f) Glu 44→Ser; Lys 50→Pro; Trp 79→Ser; Arg 81→Ala; Thr 104→Glu; Lys 125→Tyr; Gln 128→Asp; Arg 130→Asp; Lys 134→Ser; and (g) Glu 44→Leu; Lys 50→Pro; Trp 79→Pro; Arg 81→Ala; Lys 98→Arg; Lys 125→His; Ser 127→Asp; Gln 128→Thr; Arg 130→Tyr; Lys 134→Ser.

4. The mutein of claim 1, wherein the mutein is conjugated to a compound selected from the group consisting of an organic molecule, an enzyme label, a radioactive label, a colored label, a fluorescent label, a chromogenic label, a luminescent label, a hapten, digoxigenin, biotin, a cytostatic agent, a toxin, a metal complex, a metal, and colloidal gold.

5. The mutein of claim 1, wherein the mutein is fused at its N-terminus and/or its C-terminus to a fusion partner which is a protein, or a protein domain or a peptide.

6. The mutein of claim 5, wherein the protein domain is a Fc part of an immunoglobulin, a CH3 domain of an immunoglobulin, a CH4 domain of an immunoglobulin, an albumin binding peptide, or an albumin binding protein.

7. The mutein of claim 1, wherein the mutein is conjugated to a compound that extends the serum half-life of the mutein.

8. The mutein of claim 7, wherein the compound that extends the serum half-life is selected from the group consisting of a polyalkylene glycol molecule, hydroethylstarch, a Fc part of an immunoglobulin, a CH3 domain of an immunoglobulin, a CH4 domain of an immunoglobulin, an albumin binding peptide, and an albumin binding protein.

9. A nucleic acid molecule comprising a nucleotide sequence encoding the mutein of claim 1.

10. The nucleic acid molecule of claim 9, wherein the nucleic acid molecule is operably linked to a regulatory sequence to allow expression of said nucleic acid molecule.

11. The nucleic acid molecule of claim 9, wherein the nucleic acid molecule is comprised in a vector or in a phagemid vector.

12. An isolated host cell containing the nucleic acid molecule of claim 9.

13. A method of producing the mutein of claim 1 or a fusion protein of the mutein and another polypeptide, wherein the mutein or the fusion protein is produced in an isolated host cell comprising a nucleic acid coding for the mutein of claim 1 or the fusion protein.

14. The method of claim 13, further comprising isolating the mutein from the isolated host cell or its culture.

15. A pharmaceutical composition comprising the mutein of claim 1 and a pharmaceutically acceptable excipient.

16. A kit comprising the mutein of claim 1 for detecting the presence of CTLA-4.

17. A method of detecting the presence of CTLA-4, comprising the steps of:
(a) contacting the mutein of claim 1 with a test sample suspected to contain CTLA-4, thereby allowing the formation of a complex between the mutein and CTLA-4, and
(b) detecting the complex between the mutein and CTLA-4 by a suitable signal.

18. A lipocalin mutein comprising an amino acid sequence selected from the group consisting of SEQ ID NO: 12-17.

* * * * *

```
                        SEQUENCE LISTING

<160> NUMBER OF SEQ ID NOS: 38

<210> SEQ ID NO 1
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGALM1 mutant polypeptide

<400> SEQUENCE: 1

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asn Met Tyr Ala Thr Ile Tyr Glu Leu Lys Gly Asp Lys Ser Tyr
    50                  55                  60

Asn Val Thr Ser Val Ile Ser Ser His Lys Lys Cys Leu Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asp Tyr Asn Gln Tyr Ala Val Val Phe Phe Lys Leu Ala Glu Asp
        115                 120                 125

Asn Ala Glu Ser Phe Ala Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175
```

Asp Gly

<210> SEQ ID NO 2
<211> LENGTH: 73
<212> TYPE: DNA
<213> ORGANISM: Artificial Sequence
<220> FEATURE:
<223> OTHER INFORMATION: Description of Artificial Sequence: Synthetic
      Primer 73N (SSRO-1 oligonucleotide)
<220> FEATURE:
<221> NAME/KEY: modified_base
<222> LOCATION: (31)..(32)
<223> OTHER INFORMATION: a, c, g, or t
<220> FEATURE:
<221> NAME/KEY: modified_base
<222> LOCATION: (49)..(50)
<223> OTHER INFORMATION: a, c, g, or t

<400> SEQUENCE: 2
gtaggtctcg cagggaaccg gattctgaga nnsgaccagc atccgatgnn satgtatgcc      60
accatctatg agc                                                        73

<210> SEQ ID NO 3
<211> LENGTH: 52
<212> TYPE: DNA
<213> ORGANISM: Artificial Sequence
<220> FEATURE:
<223> OTHER INFORMATION: Description of Artificial Sequence: Synthetic
      Primer 52N (SSRO-2 oligonucleotide)

<400> SEQUENCE: 3
ctgggaacct ggaacaaaag ttscgatagd gtacagacac ttcttatggg ag             52

<210> SEQ ID NO 4
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer 43N (SSRO-3 oligonucleotide)
<220> FEATURE:
<221> NAME/KEY: modified_base
<222> LOCATION: (23)..(24)
<223> OTHER INFORMATION: a, c, g, or t

<400> SEQUENCE: 4
catcaagagt tacgggata agnnsagtta cctcgtccga gtg                        43

<210> SEQ ID NO 5
<211> LENGTH: 76
<212> TYPE: DNA
<213> ORGANISM: Artificial Sequence
<220> FEATURE:
<223> OTHER INFORMATION: Description of Artificial Sequence: Synthetic
      Primer 76N (SSRO-4 oligonucleotide)
<220> FEATURE:
<221> NAME/KEY: modified_base
<222> LOCATION: (44)..(45)
<223> OTHER INFORMATION: a, c, g, or t
<220> FEATURE:
<221> NAME/KEY: modified_base
<222> LOCATION: (53)..(54)
<223> OTHER INFORMATION: a, c, g, or t

<400> SEQUENCE: 5
cttggttctc ccgtagatgg taatagmgaa cgactcgdmg ttsnnayyag csnncttaaa     60
gaacaccaca gcgtac                                                    76

<210> SEQ ID NO 6
<211> LENGTH: 65
<212> TYPE: DNA
<213> ORGANISM: Artificial Sequence
<220> FEATURE:
<223> OTHER INFORMATION: Description of Artificial Sequence: Synthetic
      Primer 65N (SSRO-5 oligonucleotide)

<400> SEQUENCE: 6
cttatccccg taactcttga tgttgcccag cgtgaactcg cctggctggg aacctggaac    60
aaaag                                                                65

<210> SEQ ID NO 7
<211> LENGTH: 54
<212> TYPE: DNA
<213> ORGANISM: Artificial Sequence
<220> FEATURE:
<223> OTHER INFORMATION: Description of Artificial Sequence: Synthetic
      primer NGAL12bio

<400> SEQUENCE: 7
cttccaggac aaccaattcc atgggaagtg gtatgtggta ggtctcgcag ggaa           54

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: Synthetic
      Primer NGAL13bio

<400> SEQUENCE: 8
cctttagttc cgaagccagc tccttggttc tcccgtaga                           39

<210> SEQ ID NO 9
<211> LENGTH: 4978
<212> TYPE: DNA
<213> ORGANISM: Artificial Sequence
<220> FEATURE:
<223> OTHER INFORMATION: Description of Artificial Sequence: Synthetic
      vector construct phNGAL35 polynucleotide

<400> SEQUENCE: 9
ccatcgaatg gccagatgat taattcctaa ttttgttga cactctatca ttgatagagt      60
tattttacca ctccctatca gtgatagaga aagtgaaat gatagttcg acaaaaatct     120 agataacgag ggcaaaaat gaaaagaca gctatcgcga ttgcagtggc tctggctggc     180
ttcgctaccg tagcgcaggc catggcttcc atgaccggtg tcagcagat gggtcaggac     240 tccacctcag acctgatccc agccccacct ctgagcaagg tccctctgca gcagaacttc     300
caggacaacc aattccatgg gaagtggtat gtggtaggtc tcgcagggaa tgcaattctc     360
agagaagaca aagacccgca aaagatgtat gccaccatct atgagctgaa agaagacaag     420
agctacaatg tcacctccgt cctgtttagg aaaaagaagt gtgactactg gatcgcgact     480
tttgttccag gttcccagcc aggcgagttc acgctgggca acattaagag ttaccctgga     540
ttaacgagtt acctcgtccg agtggtgagc accaactaca accagcatgc tatggtgttc     600
ttcaaggcag tttctcaaaa cagggagtac ttcgcgatta ccatctacgg agaaccaagg     660
gagctggctt cggaactaaa ggagaacttc atccgcttct ctaaatctct gggcctccct     720
gaaaaccaca tcgtcttccc tgtcccaatc gaccagtgta tcgacggcag cgctggtggg     780
gcctagactg ttgaaagttg tttagcaaaa ccccatacag aaaattcatt tactaacgtc     840

```
tggaaagacg acaaaacttt agatcgttac gctaactatg agggctgtct gtggaatgct    900
acaggcgttg tagtttgtac tggtgacgaa actcagtgtt acgtacatg ggttcctatt    960 gggcttgcta tccctgaaaa tgagggtggt ggctctgagg gtggcggttc tgagggtggc   1020
ggttctgagg gtggcggtac taaacctcct gagtacggtg atacacctat tccgggctat   1080
acttatatca accctctcga cggcacttat ccgcctggta ctgagcaaaa ccccgctaat   1140
cctaatcctt ctcttgagga gtctcagcct cttaatactt tcatgtttca gaataatagg   1200
ttccgaaata ggcagggggc attaactgtt tatacgggca ctgttactca aggcactgac   1260
cccgttaaaa cttattacca gtacactcct gtatcatcaa agccatgta tgacgcttac    1320 tggaacggta aattcagaga ctgcgctttc cattctggct ttaatgagga tccattcgtt   1380
tgtgaatatc aaggccaatc gtctgacctg cctcaacctc ctgtcaatgc tggcggcggc   1440
tctggtggtg gttctggtgg cggctctgag ggtggtggct ctgagggtgg cggttctgag   1500
ggtggcggct ctgagggagg cggttccggt ggtggctctg gttccggtga ttttgattat   1560
gaaaagatgg caaacgctaa taaggggct atgaccgaaa atgccgatga aaacgcgcta   1620
cagtctgacg ctaaaggcaa acttgattct gtcgctactg attacggtgc tgctatcgat   1680
ggtttcattg gtgacgtttc cggccttgct aatggtaatg gtgctactgg tgattttgct   1740
ggctctaatt cccaaatggc tcaagtcggt gacggtgata attcaccttt aatgaataat   1800
ttccgtcaat atttaccttc cctccctcaa tcggttgaat gtcgcccttt tgtctttggc   1860
gctggtaaac catatgaatt ttctattgat tgtgacaaaa taaacttatt ccgtggtgtc   1920
tttgcgtttc ttttatatgt tgccaccttt atgtatgtat tttctacgtt tgctaacata   1980
ctgcgtaata aggagtctta ataagcttga cctgtgaagt gaaaaatggc gcacattgtg   2040
cgacattttt tttgtctgcc gtttaccgct actgcgtcac ggatctccac gcgccctgta   2100
gcggcgcatt aagcgcggcg ggtgtggtgg ttacgcgcag cgtgaccgct acacttgcca   2160
gcgccctagc gcccgctcct ttcgctttct tcccttcctt tctcgccacg ttcgccggct   2220
ttccccgtca gctctaaat cggggctcc ctttagggtt ccgatttagt gctttacggc    2280
acctcgaccc caaaaaactt gattaggtgt atggttcacg tagtgggcca tcgccctgat   2340
agacggtttt tcgccctttg acgttggagt ccacgttctt taatagtgga ctcttgttcc   2400
aaactggaac aacactcaac cctatctcgg tctattcttt tgatttataa gggattttgc   2460
cgatttcggc ctattggtta aaaaatgagc tgatttaaca aaaatttaac gcgaatttta   2520
acaaaatatt aacgcttaca atttcaggtg gcacttttcg gggaaatgtg cgcggaaccc   2580
ctatttgttt atttttctaa atacattcaa atatgtatcc gctcatgaga caataaccct   2640
gataaatgct tcaataatat tgaaaaagga agagtatgag tattcaacat ttccgtgtcg   2700
cccttattcc cttttttgcg gcattttgcc ttcctgtttt tgctcaccca gaaacgctgg   2760
tgaaagtaaa agatgctgaa gatcagttgg gtgcacgagt gggttacatc gaactggatc   2820
tcaacagcgg taagatcctt gagagttttc gccccgaaga acgttttcca atgatgagca   2880
cttttaaagt tctgctatgt ggcgcggtat tatcccgtat tgacgccggg caagagcaac   2940
tcggtcgccg catacactat tctcagaatg acttggttga gtactcacca gtcacagaaa   3000
agcatcttac ggatggcatg acagtaagag aattatgcag tgctgccata accatgagtg   3060
ataacactgc ggccaactta cttctgacaa cgatcggagg accgaaggag ctaaccgctt   3120
ttttgcacaa catgggggat catgtaactc gccttgatcg ttgggaaccg gagctgaatg   3180
aagccatacc aaacgacgag cgtgacacca cgatgcctgt agcaatggca acaacgttgc   3240
```

```
gcaaactatt aactggcgaa ctacttactc tagcttcccg gcaacaattg atagactgga    3300
tggaggcgga taaagttgca ggaccacttc tgcgctcggc ccttccggct ggctggttta    3360
ttgctgataa atctggagcc ggtgagcgtg gctctcgcgg tatcattgca gcactggggc    3420
cagatggtaa gccctcccgt atcgtagtta tctacacgac ggggagtcag gcaactatgg    3480
atgaacgaaa tagacagatc gctgagatag gtgcctcact gattaagcat tggtaggaat    3540
taatgatgtc tcgtttagat aaaagtaaag tgattaacag cgcattagag ctgcttaatg    3600
aggtcggaat cgaaggttta acaacccgta aactcgccca gaagctaggt gtagagcagc    3660
ctacattgta ttggcatgta aaaaataagc gggctttgct cgacgcctta gccattgaga    3720
tgttagatag gcaccatact cacttttgcc ctttagaagg ggaaagctgg caagattttt    3780
tacgtaataa cgctaaaagt tttagatgtg ctttactaag tcatcgcgat ggagcaaaag    3840
tacatttagg tacacggcct acagaaaaac agtatgaaac tctcgaaaat caattagcct    3900
ttttatgcca acaaggtttt tcactagaga atgcattata tgcactcagc gcagtggggc    3960
attttacttt aggttgcgta ttggaagatc aagagcatca agtcgctaaa gaagaaaggg    4020
aaacacctac tactgatagt atgccgccat tattacgaca agctatcgaa ttatttgatc    4080
accaaggtgc agagccagcc ttcttattcg gccttgaatt gatcatatgc ggattagaaa    4140
aacaacttaa atgtgaaagt gggtcttaaa agcagcataa ccttttttccg tgatggtaac    4200 ttcactagtt taaaggatc taggtgaaga tcctttttga taatctcatg accaaaatcc    4260
cttaacgtga gttttcgttc cactgagcgt cagaccccgt agaaaagatc aaaggatctt    4320
cttgagatcc tttttttctg cgcgtaatct gctgcttgca acaaaaaaa ccaccgctac    4380 cagcggtggt ttgtttgccg gatcaagagc taccaactct ttttccgaag gtaactggct    4440
tcagcagagc gcagatacca aatactgtcc ttctagtgta gccgtagtta ggccaccact    4500
tcaagaactc tgtagcaccg cctacatacc tcgctctgct aatcctgtta ccagtggctg    4560
ctgccagtgg cgataagtcg tgtcttaccg ggttggactc aagacgatag ttaccggata    4620
aggcgcagcg tcgggctga acggggggtt cgtgcacaca gcccagcttg gagcgaacga    4680
cctacaccga actgagatac ctacagcgtg agctatgaga aagcgccacg cttcccgaag    4740
ggagaaaggc ggacaggtat ccggtaagcg gcagggtcgg aacaggagag cgcacgaggg    4800
agcttccagg gggaaacgcc tggtatcttt atagtcctgt cgggtttcgc cacctctgac    4860
ttgagcgtcg atttttgtga tgctcgtcag gggggcggag cctatggaaa aacgccagca    4920
acgcggcctt tttacggttc ctggcctttt gctggccttt tgctcacatg acccgaca     4978

<210> SEQ ID NO 10
<211> LENGTH: 3778
<212> TYPE: DNA
<213> ORGANISM: Artificial Sequence
<220> FEATURE:
<223> OTHER INFORMATION: Description of Artificial Sequence: Synthetic
      vector phNGAL37 polynucleotide

<400> SEQUENCE: 10
ccatcgaatg gccagatgat taattcctaa ttttgttga cactctatca ttgatagagt      60
tattttacca ctccctatca gtgatagaga aaagtgaaat gaatagttcg acaaaaatct    120
agataacgag gcaaaaaat gaaaagaca gctatcgcga ttgcagtggc tctggctggc    180
ttcgctaccg tagcgcaggc catggcttcc atgaccggtg gtcagcagat gggtcaggac    240
tccacctcag acctgatccc agccccacct ctgagcaagg tccctctgca gcagaacttc    300
```

```
caggacaacc aattccatgg gaagtggtat gtggtaggtc tcgcagggaa tgcaattctc    360
agagaagaca aagacccgca aaagatgtat gccaccatct atgagctgaa agaagacaag    420
agctacaatg tcacctccgt cctgtttagg aaaagaagt gtgactactg gatcgcgact    480
tttgttccag gttcccagcc aggcgagttc acgctgggca acattaagag ttaccctgga    540
ttaacgagtt acctcgtccg agtggtgagc accaactaca accagcatgc tatggtgttc    600
ttcaaggcag tttctcaaaa cagggagtac ttcgcgatta ccatctacgg gagaaccaag    660
gagctggctt cggaactaaa ggagaacttc atccgcttct ctaaatctct gggcctccct    720
gaaaaccaca tcgtcttccc tgtcccaatc gaccagtgta tcgacggcag cgcttggtcc    780
cacccgcagt tcgaaaaata taagcttga cctgtgaagt gaaaaatggc gcacattgtg    840
cgacattttt tttgtctgcc gtttaccgct actgcgtcac ggatctccac gcgccctgta    900
gcggcgcatt aagcgcggcg ggtgtggtgg ttacgcgcag cgtgaccgct acacttgcca    960
gcgccctagc gcccgctcct ttcgctttct tcccttcctt tctcgccacg ttcgccggct   1020
ttccccgtca gctctaaat cgggggctcc ctttagggtt ccgatttagt gctttacggc   1080
acctcgaccc caaaaaactt gattagggtg atggttcacg tagtgggcca tcgccctgat   1140
agacggtttt tcgccctttg acgttggagt ccacgttctt aatagtgga ctcttgttcc   1200 aaactggaac aacactcaac cctatctcgg tctattcttt tgatttataa gggattttgc   1260
cgatttcggc ctattggtta aaaaatgagc tgatttaaca aaaatttaac gcgaatttta   1320
acaaaatatt aacgcttaca atttcaggtg gcacttttcg gggaaatgtg cgcggaaccc   1380
ctatttgttt attttttctaa atacattcaa atatgtatcc gctcatgaga caataaccct   1440
gataaatgct tcaataatat tgaaaaagga agagtatgag tattcaacat ttccgtgtcg   1500
cccttattcc cttttttgcg gcattttgcc ttcctgtttt tgctcaccca gaaacgctgg   1560
tgaaagtaaa agatgctgaa gatcagttgg gtgcacgagt gggttacatc gaactggatc   1620
tcaacagcgg taagatcctt gagagttttc gccccgaaga acgttttcca atgatgagca   1680
cttttaaagt tctgctatgt ggcgcggtat tatcccgtat tgacgccggg caagagcaac   1740
tcggtcgccg catacactat tctcagaatg acttggttga gtactcacca gtcacagaaa   1800
agcatcttac ggatggcatg acagtaagag aattatgcag tgctgccata accatgagtg   1860
ataacactgc ggccaactta cttctgacaa cgatcgagg accgaaggag ctaaccgctt   1920
ttttgcacaa catgggggat catgtaactc gccttgatcg ttgggaaccg gagctgaatg   1980
aagccatacc aaacgacgag cgtgacacca cgatgcctgt agcaatggca acaacgttgc   2040
gcaaactatt aactggcgaa ctacttactc tagcttcccg gcaacaattg atagactgga   2100
tggaggcgga taaagttgca ggaccacttc tgcgctcggc ccttccggct ggctggttta   2160
ttgctgataa atctggagcc ggtgagcgtg ctctcgcgg tatcattgca gcactggggc   2220
cagatggtaa gccctcccgt atcgtagtta tctacacgac ggggagtcag gcaactatgg   2280
atgaacgaaa tagacagatc gctgagatag gtgcctcact gattaagcat tggtaggaat   2340
taatgatgtc tcgtttagat aaaagtaaag tgattaacag cgcattagag ctgcttaatg   2400
aggtcggaat cgaaggttta acaacccgta aactcgccca gagctaggt gtagagcagc   2460 ctacattgta ttggcatgta aaaaataagc gggctttgct cgacgcctta gccattgaga   2520
tgttagatag gcaccatact cacttttgcc ctttagaagg ggaaagctgg caagattttt   2580
tacgtaataa cgctaaaagt tttagatgtg ctttactaag tcatcgcgat ggagcaaaag   2640
```

```
tacatttagg tacacggcct acagaaaaac agtatgaaac tctcgaaaat caattagcct    2700
ttttatgcca acaaggtttt tcactagaga atgcattata tgcactcagc gcagtggggc    2760
attttacttt aggttgcgta ttggaagatc aagagcatca agtcgctaaa gaagaaaggg    2820
aaacacctac tactgatagt atgccgccat tattacgaca agctatcgaa ttatttgatc    2880
accaaggtgc agagccagcc ttcttattcg gccttgaatt gatcatatgc ggattagaaa    2940
aacaacttaa atgtgaaagt gggtcttaaa agcagcataa ccttttttccg tgatggtaac    3000
ttcactagtt taaaaggatc taggtgaaga tccttttttga taatctcatg accaaaatcc    3060
cttaacgtga gttttcgttc cactgagcgt cagaccccgt agaaaagatc aaaggatctt    3120
cttgagatcc ttttttttctg cgcgtaatct gctgcttgca acaaaaaaaa ccaccgctac    3180
cagcggtggt ttgtttgccg gatcaagagc taccaactct ttttccgaag gtaactggct    3240
tcagcagagc gcagatacca aatactgtcc ttctagtgta gccgtagtta ggccaccact    3300
tcaagaactc tgtagcaccg cctacatacc tcgctctgct aatcctgtta ccagtggctg    3360
ctgccagtgg cgataagtcg tgtcttaccg ggttggactc aagacgatag ttaccggata    3420
aggcgcagcg gtcgggctga acggggggtt cgtgcacaca gcccagcttg gagcgaacga    3480
cctacaccga actgagatac ctacagcgtg agctatgaga agcgccacg cttcccgaag    3540
ggagaaaggc ggacaggtat ccggtaagcg gcagggtcgg aacaggagag cgcacgaggg    3600
agcttccagg gggaaacgcc tggtatcttt atagtcctgt cgggtttcgc cacctctgac    3660
ttgagcgtcg atttttgtga tgctcgtcag gggggcggag cctatggaaa aacgccagca    3720
acgcggcctt tttacggttc ctggcctttt gctggccttt tgctcacatg acccgaca     3778
```

<210> SEQ ID NO 11
<211> LENGTH: 3745
<212> TYPE: DNA
<213> ORGANISM: Artificial Sequence
<220> FEATURE:
<223> OTHER INFORMATION: Description of Artificial Sequence: Synthetic
vector phNGAL15 polynucleotide

<400> SEQUENCE: 11

```
ccatcgaatg gccagatgat taattcctaa ttttttgttga cactctatca ttgatagagt     60
tattttacca ctccctatca gtgatagaga aaagtgaaat gaatagttcg acaaaaatct    120
agataacgag ggcaaaaaat gaaaagaca gctatcgcga ttgcagtggc tctggctggc    180
ttcgctaccg tagcgcaggc ccaggactcc acctcagacc tgatcccagc cccacctctg    240
agcaaggtcc ctctgcagca gaacttccag gacaaccaat tccatgggaa gtggtatgtg    300
gtaggtctcg cagggaatgc aattctcaga gaagacaaag acccgcaaaa gatgtatgcc    360
accatctatg agctgaaaga agacaagagc tacaatgtca cctccgtcct gtttaggaaa    420
aagaagtgtg actactggat caggactttt gttccaggtt cccagccagg cgagttcacg    480
ctgggcaaca ttaagagtta ccctggatta acgagttacc tcgtccgagt ggtgagcacc    540
aactacaacc agcatgctat ggtgttcttc aagaaagttt ctcaaaacag ggagtacttc    600
aagattacca tctacgggag aaccaaggag ctggcttcgg aactaaagga gaacttcatc    660
cgcttctcta atctctgggg cctccctgaa accacatcg tcttccctgt cccaatcgac    720
cagtgtatcg acggcagcgc ttggtcccac ccgcagttcg aaaaataata agcttgacct    780
gtgaagtgaa aaatggcgca cattgtgcga cattttttt gtctgccgtt taccgctact    840
gcgtcacgga tctccacgcg ccctgtagcg gcgcattaag cgcggcgggt gtggtggtta    900
```

```
cgcgcagcgt gaccgctaca cttgccagcg ccctagcgcc cgctcctttc gctttcttcc      960
cttcctttct cgccacgttc gccggctttc cccgtcaagc tctaaatcgg gggctcccctt    1020
tagggttccg atttagtgct ttacggcacc tcgaccccaa aaaacttgat tagggtgatg    1080
gttcacgtag tgggccatcg ccctgataga cggttttttcg ccctttgacg ttggagtcca    1140
cgttctttaa tagtggactc ttgttccaaa ctggaacaac actcaaccct atctcggtct    1200
attcttttga tttataaggg attttgccga tttcggccta ttggttaaaa aatgagctga    1260
tttaacaaaa atttaacgcg aattttaaca aaatattaac gtttacaatt tcaggtggca    1320
cttttcgggg aaatgtgcgc ggaacccccta tttgtttatt tttctaaata cattcaaata    1380
tgtatccgct catgagacaa taaccctgat aaatgcttca ataatattga aaaggaaga    1440
gtatgagtat tcaacatttc cgtgtcgccc ttattccctt ttttgcggca ttttgccttc    1500
ctgttttttgc tcacccagaa acgctggtga agtaaaaga tgctgaagat cagttgggtg    1560
cacgagtggg ttacatcgaa ctggatctca acagcggtaa gatccttgag agttttcgcc    1620
ccgaagaacg ttttccaatg atgagcactt ttaaagttct gctatgtggc gcggtattat    1680
cccgtattga cgccgggcaa gagcaactcg gtcgccgcat acactattct cagaatgact    1740
tggttgagta ctcaccagtc acagaaaagc atcttacgga tggcatgaca gtaagagaat    1800
tatgcagtgc tgccataacc atgagtgata acactgcggc caacttactt ctgacaacga    1860
tcggaggacc gaaggagcta accgcttttt tgcacaacat ggggggatcat gtaactcgcc    1920
ttgatcgttg ggaaccggag ctgaatgaag ccataccaaa cgacgagcgt gacaccacga    1980
tgcctgtagc aatggcaaca acgttgcgca aactattaac tggcgaacta cttactctag    2040
cttcccggca acaattgata gactggatgg aggcggataa agttgcagga ccacttctgc    2100
gctcggccct tccggctggc tggtttattg ctgataaatc tggagccggt gagcgtggct    2160
ctcgcggtat cattgcagca ctggggccag atggtaagcc ctcccgtatc gtagttatct    2220
acacgacggg gagtcaggca actatggatg aacgaaatag acagatcgct gagataggtg    2280
cctcactgat taagcattgg taggaattaa tgatgtctcg tttagataaa agtaaagtga    2340
ttaacagcgc attagagctg cttaatgagg tcggaatcga aggtttaaca acccgtaaac    2400
tcgcccagaa gctaggtgta gagcagccta cattgtattg gcatgtaaaa aataagcggg    2460
ctttgctcga cgccttagcc attgagatgt tagataggca ccatactcac ttttgccctt    2520
tagaagggga aagctggcaa gatttttttac gtaataacgc taaaagttttt agatgtgctt    2580
tactaagtca tcgcgatgga gcaaaagtac atttaggtac acggcctaca gaaaaacagt    2640
atgaaactct cgaaaatcaa ttagcctttt tatgccaaca aggtttttca ctagagaatg    2700
cattatatgc actcagcgca gtggggcatt ttactttagg ttgcgtattg gaagatcaag    2760
agcatcaagt cgctaaagaa gaaagggaaa cacctactac tgatagtatg ccgccattat    2820
acgacaagc tatcgaatta tttgatcacc aaggtgcaga gccagccttc ttattcggcc    2880
ttgaattgat catatgcgga ttagaaaaac aacttaaatg tgaaagtggg tcttaaaagc    2940
agcataaacct ttttccgtga tggtaacttc actagtttaa aaggatctag gtgaagatcc    3000
tttttgataa tctcatgacc aaaatcccctt aacgtgagtt ttcgttccac tgagcgtcag    3060
accccgtaga aaagatcaaa ggatcttctt gagatccttt ttttctgcgc gtaatctgct    3120
gcttgcaaac aaaaaaacca ccgctaccag cggtggtttg tttgccggat caagagctac    3180
caactctttt tccgaaggta actggcttca gcagagcgca gataccaaat actgtccttc    3240
tagtgtagcc gtagttaggc caccacttca agaactctgt agcaccgcct acatacctcg    3300
```

-continued

```
ctctgctaat cctgttacca gtggctgctg ccagtggcga taagtcgtgt cttaccgggt    3360
tggactcaag acgatagtta ccggataagg cgcagcggtc gggctgaacg ggggggttcgt    3420 gcacacagcc cagcttggag cgaacgacct acaccgaact gagataccta cagcgtgagc    3480
tatgagaaag cgccacgctt cccgaaggga gaaaggcgga caggtatccg gtaagcggca    3540
gggtcggaac aggagagcgc acgagggagc ttccaggggg aaacgcctgg tatctttata    3600
gtcctgtcgg gtttcgccac ctctgacttg agcgtcgatt tttgtgatgc tcgtcagggg    3660
ggcggagcct atggaaaaac gccagcaacg cggccttttt acggttcctg gccttttgct    3720
ggccttttgc tcacatgacc cgaca                                          3745
```

<210> SEQ ID NO 12
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGALM2 polypeptide

<400> SEQUENCE: 12

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Leu Leu Arg Asp Asp Gln His Pro
        35                  40                  45

Met Asp Met Tyr Ala Thr Ile Tyr Glu Leu Lys Gly Asp Lys Ser Tyr
    50                  55                  60

Asn Val Thr Ser Val Ile Ser Ser His Lys Lys Cys Leu Tyr Pro Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Trp Ser Tyr Leu Val Arg Val Val Ser
            100                 105                 110

Thr Asp Tyr Asn Gln Tyr Ala Val Val Phe Phe Lys His Ala Asp Thr
        115                 120                 125

Asn Tyr Glu Ser Phe Ser Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 13
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGALM3 polypeptide

<400> SEQUENCE: 13

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30
```

```
Val Val Gly Leu Ala Gly Asn Arg Ile Leu Arg Gln Asp Gln His Pro
            35                  40                  45

Met Leu Met Tyr Ala Thr Ile Tyr Glu Leu Lys Gly Asp Lys Ser Tyr
 50                  55                  60

Asn Val Thr Ser Val Ile Ser Ser His Lys Lys Cys Leu Tyr Pro Ile
 65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Val Ser Tyr Leu Val Arg Val Val Ser
                100                 105                 110

Thr Asp Tyr Asn Gln Tyr Ala Val Val Phe Phe Lys His Ala Asp Thr
                115                 120                 125

Asn Tyr Glu Ser Phe Ser Ile Thr Ile Tyr Gly Arg Thr Lys Glu Leu
130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 14
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGALM4 polypeptide

<400> SEQUENCE: 14

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
                20                  25                  30

Val Val Gly Leu Ala Gly Asn Arg Ile Leu Arg Asp Asp Gln His Pro
            35                  40                  45

Met Pro Met Tyr Ala Thr Ile Tyr Glu Leu Lys Gly Asp Lys Ser Tyr
 50                  55                  60

Asn Val Thr Ser Val Ile Ser Ser His Lys Lys Cys Leu Tyr Pro Ile
 65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Trp Ser Tyr Leu Val Arg Val Val Ser
                100                 105                 110

Thr Asp Tyr Asn Gln Tyr Ala Val Val Phe Phe Lys His Ala Asp Ser
                115                 120                 125

Asn Tyr Glu Ser Phe Ser Ile Thr Ile Tyr Gly Arg Thr Lys Glu Leu
130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 15
<211> LENGTH: 178
```

```
<212> TYPE: PRT
<213> ORGANISM: Artificial Sequence
<220> FEATURE:
<223> OTHER INFORMATION: Description of Artificial Sequence: Synthetic
      hNGALM5 polypeptide

<400> SEQUENCE: 15

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Ser Asp Gln His Pro
        35                  40                  45

Met Arg Met Tyr Ala Thr Ile Tyr Glu Leu Lys Gly Asp Lys Ser Tyr
50                  55                  60

Asn Val Thr Ser Val Ile Ser Ser His Lys Lys Cys Leu Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Trp Ser Tyr Leu Val Arg Val Val Ser
            100                 105                 110

Thr Asp Tyr Asn Gln Tyr Ala Val Val Phe Phe Lys His Ala Asp Thr
        115                 120                 125

Asn Tyr Glu Ser Phe Ser Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 16
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGALM6 polypeptide

<400> SEQUENCE: 16

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Ser Asp Gln His Pro
        35                  40                  45

Met Pro Met Tyr Ala Thr Ile Tyr Glu Leu Lys Gly Asp Lys Ser Tyr
50                  55                  60

Asn Val Thr Ser Val Ile Ser Ser His Lys Lys Cys Leu Tyr Ser Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Glu Ser Tyr Leu Val Arg Val Val Ser
            100                 105                 110

Thr Asp Tyr Asn Gln Tyr Ala Val Val Phe Phe Lys Tyr Ala Ser Asp
        115                 120                 125

Asn Asp Glu Ser Phe Ser Ile Thr Ile Tyr Gly Arg Thr Lys Glu Leu
```

```
                130                 135                 140
Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 17
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGALM7 polypeptide

<400> SEQUENCE: 17

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Leu Ala Gly Asn Arg Ile Leu Arg Leu Asp Gln His Pro
            35                  40                  45

Met Pro Met Tyr Ala Thr Ile Tyr Glu Leu Lys Gly Asp Lys Ser Tyr
        50                  55                  60

Asn Val Thr Ser Val Ile Ser Ser His Lys Lys Cys Leu Tyr Pro Ile
65                  70                  75                  80

Ala Thr Phe Val Pro Gly Ser Gln Pro Gly Glu Phe Thr Leu Gly Asn
                85                  90                  95

Ile Arg Ser Tyr Gly Asp Lys Thr Ser Tyr Leu Val Arg Val Val Ser
            100                 105                 110

Thr Asp Tyr Asn Gln Tyr Ala Val Val Phe Phe Lys His Ala Asp Thr
        115                 120                 125

Asn Tyr Glu Ser Phe Ser Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer (ASKD20)

<400> SEQUENCE: 18
ccactcccta tcagtgat                                                  18

<210> SEQ ID NO 19
<211> LENGTH: 31
<212> TYPE: DNA
<213> ORGANISM: Artificial Sequence
<220> FEATURE:
<223> OTHER INFORMATION: Description of Artificial Sequence: Synthetic
      Primer (NGAL67)

<400> SEQUENCE: 19
```

-continued cttcacaggt caagcttatt atttttcgaa c                                                31

<210> SEQ ID NO 20
<211> LENGTH: 178
<212> TYPE: PRT
<213> ORGANISM: Homo sapiens
<220> FEATURE:
<223> OTHER INFORMATION: wt Lcn2 (hNGAL)

<400> SEQUENCE: 20

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Ser Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 21
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, c, t, g, unknown or other

<400> SEQUENCE: 21
ccannnnnnt gg                                                                     12

<210> SEQ ID NO 22
<211> LENGTH: 20
<212> TYPE: PRT
<213> ORGANISM: Homo sapiens

<400> SEQUENCE: 22

Met Pro Leu Gly Leu Leu Trp Leu Gly Leu Ala Leu Leu Gly Ala Leu
1               5                   10                  15

His Ala Gln Ala
            20

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 23

His His His His His His
1               5

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Met Ala Ser Met Thr Gly Gly Gln Gln Met Gly
1               5                   10

<210> SEQ ID NO 25
<211> LENGTH: 188
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asn Met Tyr Ala Thr Ile Tyr Glu Leu Lys Gly Asp Lys Ser Tyr
    50                  55                  60

Asn Val Thr Ser Val Ile Ser Ser His Lys Lys Cys Leu Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asp Tyr Asn Gln Tyr Ala Val Val Phe Phe Lys Leu Ala Glu Asp
        115                 120                 125

Asn Ala Glu Ser Phe Ala Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
            180                 185

<210> SEQ ID NO 26
<211> LENGTH: 44
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 26
ctggaacaaa agtcscgata gdgtacagac acttcttatg ggag                    44

<210> SEQ ID NO 27
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (44)..(45)
<223> OTHER INFORMATION: a, c, t, g, unknown or other
<220> FEATURE:
<221> NAME/KEY: modified_base
<222> LOCATION: (53)..(54)
<223> OTHER INFORMATION: a, c, t, g, unknown or other

<400> SEQUENCE: 27
cttggttctc ccgtagatgg taatagmgaa cgactccdmg ttsnnayyag csnncttaaa    60
gaacaccaca gcgtac                                                   76

<210> SEQ ID NO 28
<211> LENGTH: 574
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(564)

<400> SEQUENCE: 28 cag gac tcc acc tca gac ctg atc cca gcc cca cct ctg agc aag gtc     48
Gln Asp Ser Thr Ser Asp Leu Ile Pro Ala Pro Pro Leu Ser Lys Val
1               5                   10                  15 cct ctg cag cag aac ttc cag gac aac caa ttc cat ggg aag tgg tat     96
Pro Leu Gln Gln Asn Phe Gln Asp Asn Gln Phe His Gly Lys Trp Tyr
            20                  25                  30 gtg gta ggt ctc gca ggg aac cgg att ctg aga gat gac cag cat ccg    144
Val Val Gly Leu Ala Gly Asn Arg Ile Leu Arg Asp Asp Gln His Pro
        35                  40                  45 atg aat atg tat gcc acc atc tat gag ctg aaa gga gac aag agc tac    192
Met Asn Met Tyr Ala Thr Ile Tyr Glu Leu Lys Gly Asp Lys Ser Tyr
    50                  55                  60 aat gtc acc tcc gtc att agc tcc cat aag aag tgt ctg tac acg atc    240
Asn Val Thr Ser Val Ile Ser Ser His Lys Lys Cys Leu Tyr Thr Ile
65                  70                  75                  80 gcg act ttt gtt cca ggt tcc cag cca ggc gag ttc acg ctg ggc aac    288
Ala Thr Phe Val Pro Gly Ser Gln Pro Gly Glu Phe Thr Leu Gly Asn
                85                  90                  95 atc aag agt tac ggg gat aag acg agt tac ctc gtc cga gtg gtg agc    336
Ile Lys Ser Tyr Gly Asp Lys Thr Ser Tyr Leu Val Arg Val Val Ser
            100                 105                 110 acc gac tac aac cag tac gct gtg gtg ttc ttt aag ctt gct gag gat    384
Thr Asp Tyr Asn Gln Tyr Ala Val Val Phe Phe Lys Leu Ala Glu Asp
        115                 120                 125 aac gcg gag tcg ttc gca att acc atc tac ggg aga acc aag gag ctg    432
Asn Ala Glu Ser Phe Ala Ile Thr Ile Tyr Gly Arg Thr Lys Glu Leu
```

```
                Asn Ala Glu Ser Phe Ala Ile Thr Ile Tyr Gly Arg Thr Lys Glu Leu
                                130                 135                 140 gct tcg gaa cta aag gag aac ttc atc cgc ttc tct aaa tct ctg ggc        480
Ala Ser Glu Leu Lys Glu Asn Phe Ile Arg Phe Ser Lys Ser Leu Gly
145                 150                 155                 160 ctc cct gaa aac cac atc gtc ttc cct gtc cca atc gac cag tgt atc        528
Leu Pro Glu Asn His Ile Val Phe Pro Val Pro Ile Asp Gln Cys Ile
                165                 170                 175 gac ggc agc gct tgg tct cac ccg cag ttc gaa aaa taataagctt             574
Asp Gly Ser Ala Trp Ser His Pro Gln Phe Glu Lys
                180                 185
```

<210> SEQ ID NO 29
<211> LENGTH: 574
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29

```
aagcttatta ttttcgaac tgcgggtgag accaagcgct gccgtcgata cactggtcga        60
ttgggacagg gaagacgatg tggttttcag ggaggcccag agatttagag aagcggatga      120
agttctcctt tagttccgaa gccagctcct tggttctccc gtagatggta attgcgaacg      180
actccgcgtt atcctcagca agcttaaaga acaccacagc gtactggttg tagtcggtgc      240
tcaccactcg gacgaggtaa ctcgtcttat ccccgtaact cttgatgttg cccagcgtga      300
actcgcctgg ctgggaacct ggaacaaaag tcgcgatcgt gtacagacac ttcttatggg      360
agctaatgac ggaggtgaca ttgtagctct tgtctccttt cagctcatag atggtggcat      420
acatattcat cggatgctgg tcatctctca gaatccggtt ccctgcgaga cctaccacat      480
accacttccc atggaattgg ttgtcctgga agttctgctg cagagggacc ttgctcagag      540
gtggggctgg gatcaggtct gaggtggagt cctg                                 574
```

<210> SEQ ID NO 30
<211> LENGTH: 188
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Leu Ala Gly Asn Arg Leu Leu Arg Asp Asp Gln His Pro
            35                  40                  45

Met Asp Met Tyr Ala Thr Ile Tyr Glu Leu Lys Gly Asp Lys Ser Tyr
    50                  55                  60

Asn Val Thr Ser Val Ile Ser Ser His Lys Lys Cys Leu Tyr Pro Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Trp Ser Tyr Leu Val Arg Val Val Ser
                100                 105                 110

Thr Asp Tyr Asn Gln Tyr Ala Val Val Phe Phe Lys His Ala Asp Thr
```

```
                    115                 120                 125
Asn Tyr Glu Ser Phe Ser Ile Thr Ile Tyr Gly Arg Thr Lys Glu Leu
        130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
            180                 185

<210> SEQ ID NO 31
<211> LENGTH: 188
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Gln Asp Gln His Pro
        35                  40                  45

Met Leu Met Tyr Ala Thr Ile Tyr Glu Leu Lys Gly Asp Lys Ser Tyr
    50                  55                  60

Asn Val Thr Ser Val Ile Ser Ser His Lys Lys Cys Leu Tyr Pro Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Val Ser Tyr Leu Val Arg Val Val Ser
            100                 105                 110

Thr Asp Tyr Asn Gln Tyr Ala Val Val Phe Phe Lys His Ala Asp Thr
        115                 120                 125

Asn Tyr Glu Ser Phe Ser Ile Thr Ile Tyr Gly Arg Thr Lys Glu Leu
        130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
            180                 185

<210> SEQ ID NO 32
<211> LENGTH: 188
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
```

```
            35                  40                  45
Met Pro Met Tyr Ala Thr Ile Tyr Glu Leu Lys Gly Asp Lys Ser Tyr
 50                  55                  60

Asn Val Thr Ser Val Ile Ser Ser His Lys Lys Cys Leu Tyr Pro Ile
 65                  70                  75                  80

Ala Thr Phe Val Pro Gly Ser Gln Pro Gly Glu Phe Thr Leu Gly Asn
                 85                  90                  95

Ile Lys Ser Tyr Gly Asp Lys Trp Ser Tyr Leu Val Arg Val Val Ser
                100                 105                 110

Thr Asp Tyr Asn Gln Tyr Ala Val Val Phe Phe Lys His Ala Asp Ser
                115                 120                 125

Asn Tyr Glu Ser Phe Ser Ile Thr Ile Tyr Gly Arg Thr Lys Glu Leu
            130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
                180                 185
```

<210> SEQ ID NO 33
<211> LENGTH: 188
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

```
Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
                 20                  25                  30

Val Val Gly Leu Ala Gly Asn Arg Ile Leu Arg Ser Asp Gln His Pro
             35                  40                  45

Met Arg Met Tyr Ala Thr Ile Tyr Glu Leu Lys Gly Asp Lys Ser Tyr
 50                  55                  60

Asn Val Thr Ser Val Ile Ser Ser His Lys Lys Cys Leu Tyr Thr Ile
 65                  70                  75                  80

Ala Thr Phe Val Pro Gly Ser Gln Pro Gly Glu Phe Thr Leu Gly Asn
                 85                  90                  95

Ile Lys Ser Tyr Gly Asp Lys Trp Ser Tyr Leu Val Arg Val Val Ser
                100                 105                 110

Thr Asp Tyr Asn Gln Tyr Ala Val Val Phe Phe Lys His Ala Asp Thr
                115                 120                 125

Asn Tyr Glu Ser Phe Ser Ile Thr Ile Tyr Gly Arg Thr Lys Glu Leu
            130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
                180                 185
```

<210> SEQ ID NO 34
<211> LENGTH: 188

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Ser Asp Gln His Pro
        35                  40                  45

Met Pro Met Tyr Ala Thr Ile Tyr Glu Leu Lys Gly Asp Lys Ser Tyr
    50                  55                  60

Asn Val Thr Ser Val Ile Ser Ser His Lys Lys Cys Leu Tyr Ser Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Glu Ser Tyr Leu Val Arg Val Val Ser
            100                 105                 110

Thr Asp Tyr Asn Gln Tyr Ala Val Val Phe Phe Lys Tyr Ala Ser Asp
        115                 120                 125

Asn Asp Glu Ser Phe Ser Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
            180                 185

<210> SEQ ID NO 35
<211> LENGTH: 188
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Leu Asp Gln His Pro
        35                  40                  45

Met Pro Met Tyr Ala Thr Ile Tyr Glu Leu Lys Gly Asp Lys Ser Tyr
    50                  55                  60

Asn Val Thr Ser Val Ile Ser Ser His Lys Lys Cys Leu Tyr Pro Ile
65                  70                  75                  80

Ala Thr Phe Val Pro Gly Ser Gln Pro Gly Glu Phe Thr Leu Gly Asn
                85                  90                  95

Ile Arg Ser Tyr Gly Asp Lys Thr Ser Tyr Leu Val Arg Val Val Ser
            100                 105                 110

Thr Asp Tyr Asn Gln Tyr Ala Val Val Phe Phe Lys His Ala Asp Thr
        115                 120                 125

```
Asn Tyr Glu Ser Phe Ser Ile Thr Ile Tyr Gly Arg Thr Lys Glu Leu
    130                 135                 140

Ala Ser Glu Leu Lys Gly Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
                180                 185

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Leu Met Tyr Pro Pro Tyr Tyr
1               5

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      5xHis tag

<400> SEQUENCE: 37

His His His His His
1               5

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ser Ala Trp Ser His Pro Gln Phe Glu Lys
1               5                   10
```